US012612382B2

(12) United States Patent
Holmberg et al.

(10) Patent No.: US 12,612,382 B2
(45) Date of Patent: *Apr. 28, 2026

(54) PROCESS FOR PREPARING 6-SUBSTITUTED-1-(2H)-ISOQUINOLINONES AND INTERMEDIATE COMPOUND

(71) Applicant: Valo Health, Inc., Boston, MA (US)

(72) Inventors: Par Holmberg, Boston, MA (US); Sumit Kumar, Boston, MA (US); Matthew James Wathier, Boston, MA (US); Huimin Zhai, Boston, MA (US); Christophe Benelli, Boston, MA (US); Xavier Bon, Boston, MA (US); Boris Camuzat-Dedenis, Boston, MA (US); Fabien Rodier, Boston, MA (US)

(73) Assignee: VALO HEALTH INC., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/636,763

(22) Filed: Apr. 16, 2024

(65) Prior Publication Data

US 2024/0287030 A1 Aug. 29, 2024

Related U.S. Application Data

(63) Continuation of application No. PCT/US2023/071317, filed on Jul. 31, 2023.

(60) Provisional application No. 63/394,110, filed on Aug. 1, 2022.

(51) Int. Cl.
*C07D 401/12* (2006.01)

(52) U.S. Cl.
CPC .................................. *C07D 401/12* (2013.01)

(58) Field of Classification Search
CPC .................................................... C07D 401/12
See application file for complete search history.

(56) References Cited

U.S. PATENT DOCUMENTS

| | | | | |
|---|---|---|---|---|
| 8,598,201 | B2 | 12/2013 | Nagel et al. | |
| 8,710,078 | B2 | 4/2014 | Nagel et al. | |
| 8,716,481 | B2 | 5/2014 | Rossen et al. | |
| 8,785,642 | B2 | 7/2014 | Gessler et al. | |
| 2012/0316152 | A1* | 12/2012 | Plettenburg | A61P 9/10 514/309 |

FOREIGN PATENT DOCUMENTS

| | | | | |
|---|---|---|---|---|
| JP | 2007238458 A | 9/2007 | | |
| WO | WO-2007012421 A1 * | 2/2007 | | A01N 43/54 |
| WO | WO 2007/065916 A1 | 6/2007 | | |
| WO | WO 2009/080335 A1 | 7/2009 | | |
| WO | WO 2009/156099 | 12/2009 | | |
| WO | WO-2010072352 A1 | 7/2010 | | |
| WO | WO 2013/007502 | 1/2013 | | |
| WO | WO 2013/007518 | 1/2013 | | |
| WO | WO 2013/007519 | 1/2013 | | |
| WO | 2020/123674 A1 | 6/2020 | | |

OTHER PUBLICATIONS

Senger et al. J. Org. Chem. 2012, 77, 21, 9535-9540. (Year: 2012).*
Campeau et al. Journal of the American Chemical Society 2008 130 (11), 3266-3267. (Year: 2008).*
International Search Report and Written Opinion in International Application No. PCT/US2023/071317, dated Sep. 21, 2023 (19 pages).
US Office Action, Nov. 19, 2024, pp. 1-17, issued in U.S. Appl. No. 18/636,832, USPTO, Alexandria, Virginia.
U.S. Non-Final Office Action issued in U.S. Appl. No. 18/636,832 dated Aug. 7, 2024 (12 pages).
Wuts, Peter G.M. et al.; "Protection for the Amino Group", Greene's Protective Groups in Organic Synthesis, 2007, pp. 696-926, Fourth Edition, John Wiley & Sons, Inc. (231 pages).

(Continued)

*Primary Examiner* — Matthew P Coughlin
*Assistant Examiner* — Ashli Ariana Chicks
(74) *Attorney, Agent, or Firm* — COOLEY LLP

(57) ABSTRACT

The invention relates to substituted 6-substituted isoquinoline oxide compounds of formula (V)

(V)

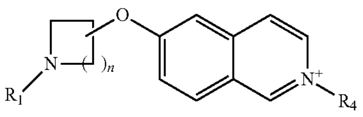

and to a process for making them. The compounds of formula (V) can be used as intermediates for making 6-substituted-1-(2H)-isoquinolinone compounds of formula (I)

(I)

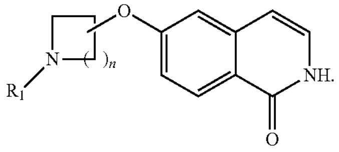

The compounds of formula (I) are inhibitors of the enzyme Rho-kinase, or can be used as intermediates in the preparation of further inhibitors of the Rho-kinase enzyme.

27 Claims, No Drawings

(56) References Cited

OTHER PUBLICATIONS

International Preliminary Report on Patentability (PCT/IB/338 & PCT/IB/373) issued in PCT Application No. US2023/071317 dated Feb. 4, 2025, (Written Opinion (PCT/ISA/237), filed on Jul. 16. 2024) (13 pages).
Communication Pursuant to Rule 164(2)(b) and Article 94(3) EPC issued in EP Application No. 23761702.2 dated Feb. 17, 2025 (11 pages).
Liu, J et al.; "Light-induced [2+2] cycloadditions for the construction of cyclobutene-fused. Pyridinyl sulfonyl fluorides," Organic & Biomolecular Chemistry, 2020, 18, 4019, with Supplemental Information (184 pages).

* cited by examiner

PROCESS FOR PREPARING 6-SUBSTITUTED-1-(2H)-ISOQUINOLINONES AND INTERMEDIATE COMPOUND

FIELD OF THE INVENTION

This application is a continuation of International Application No. PCT/US2023/071317, filed Jul. 31, 2023, which claims the benefit of U.S. Provisional Application No. 63/394,110, filed Aug. 1, 2022. The present invention relates to substituted 6-substituted isoquinoline oxide compounds of formula (V)

(V)

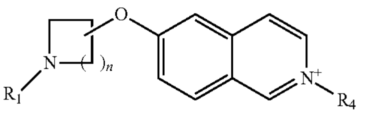

and to a process for making them. The compounds of formula (V) can be used as intermediates for making 6-substituted-1-(2H)-isoquinolinone compounds of formula (I)

(I)

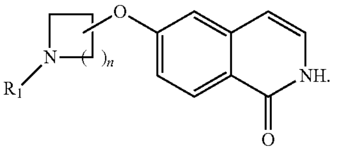

BACKGROUND OF THE INVENTION

The present invention relates to a compound of the formula (V)

(V)

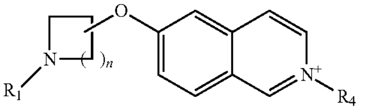

wherein n is 1, 2, 3, or 4 and $R_1$ is H, a $C_1$-$C_6$ alkyl group, or a protecting group. The protecting group prevents the nitrogen atom to which it is attached from reacting with other molecules (e.g., other reagents) during a chemical reaction and can be selected from a variety of groups, including but not limited to those mentioned in P. G. M. Wuts & T. W. Greene, Protective Groups in Organic Synthesis, Fourth Edition, John Wiley and Sons, New York, 2007 ("Greene"), Chapter 7: Protection for the Amino Group. Moreover, reference is made to WO 2009/080335 where suitable groups in connection with the synthesis of compounds of formula (I) have been described. The present invention further relates to a process for preparing a compound of formula (V). The present invention also relates to the use of a compound of formula (V) 6-substituted isoquinoline oxide compounds of formula (V) as intermediates in the preparation of a 6-substituted-1-(2H)-isoquinolinone derivative of formula (I)

(I)

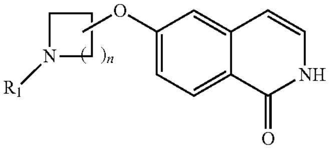

wherein n is 1, 2, 3, or 4 and $R_1$ is H, a $C_1$-$C_6$ alkyl group, or a protecting group as defined above. Compounds of formula (I) may exist in lactam form and/or as a tautomeric lactim form, as shown below:

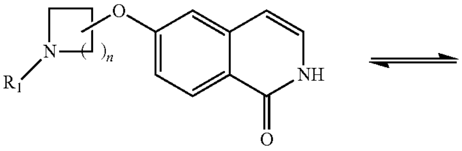

(I)
Lactam Form

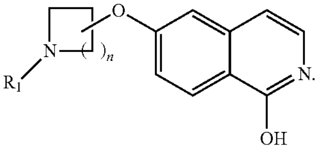

(I)
Lactim Form

The compounds of formula (I) are inhibitors of the enzyme Rho-kinase, which are beneficial for the treatment of inter alia, hypertension, pulmonary hypertension, ocular hypertension, retinopathy, and glaucoma, peripheral circulatory disorder, peripheral occlusive arterial disease (PAOD), coronary heart disease, angina pectoris, heart hypertrophy, heart failure, ischemic diseases, ischemic organ failure (end organ damage), fibroid lung, fibroid liver, liver failure, nephropathy, including hypertension-induced, non-hypertension-induced, and diabetic nephropathies, renal failure, fibroid kidney, renal glomerulosclerosis, organ hypertrophy, asthma, chronic obstructive pulmonary disease (COPD), adult respiratory distress syndrome, thrombotic disorders, stroke, cerebral vasospasm, cerebral ischemia, pain, e.g. neuropathic pain, neuronal degeneration, spinal cord injury, Alzheimer's disease, premature birth, erectile dysfunction, endocrine dysfunctions, arteriosclerosis, prostatic hypertrophy, diabetes and complications of diabetes, metabolic syndrome, blood vessel restenosis, atherosclerosis, inflammation, autoimmune diseases, AIDS, osteopathy such as osteoporosis, infection of digestive tracts with bacteria, sepsis, cancer development and progression, e.g. cancers of the breast, colon, prostate, ovaries, brain and lung and their metastases. The compounds of formula (I) can also be used as intermediates in the preparation of further inhibitors of the Rho-kinase enzyme. Compounds of formula (I) and synthetic routes for the preparation of compounds of formula (I) are described in, e.g., U.S. Pat. Nos. 8,716,481 and 8,785,642.

There are problems associated with current synthetic routes for the preparation of compounds of formula (I). One problem is that the current synthetic routes generate dimethylamine and pyrrolidine as by-products in stoichiometric amounts. Dimethylamine and pyrrolidine exhibit properties similar to those of the target compounds of formula (I) and may therefore prove difficult to purge to acceptable levels in the active pharmaceutical ingredient (API). Another problem is that the current synthetic routes generate intermediates with poor crystalline properties and may therefore pose difficulties in isolation and purification.

Another problem is that the current synthetic routes generate 6-(piperidin-4-yloxy)-1H-isochromen-1-one, which has the following structure:

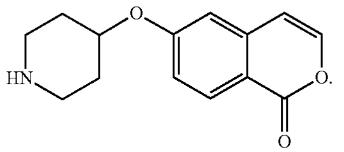 [SMILES: O=c1occc2cc(OC3CCNCC3)ccc12]

6-(Piperidin-4-yloxy)-1H-isochromen-1-one exhibits mutagenic properties. Accordingly, it is the object of the present invention to provide an alternative route for the preparation of compounds of formula (I) that does not generate by-products that may be difficult to remove from the target compounds of formula (I), does not generate intermediates with poor crystalline properties, and does not generate side-products with undesirable properties.

These compounds of formula (I) may be used as Rho-kinase inhibitors or may be used as intermediates in the synthesis of further inhibitors.

BRIEF SUMMARY OF THE INVENTION

The overall process steps to make substituted 6-substituted isoquinoline oxide compounds of formula (V) and to use them as intermediates in the preparation of a compound of formula (I) are shown in Scheme 1 below.

Scheme 1

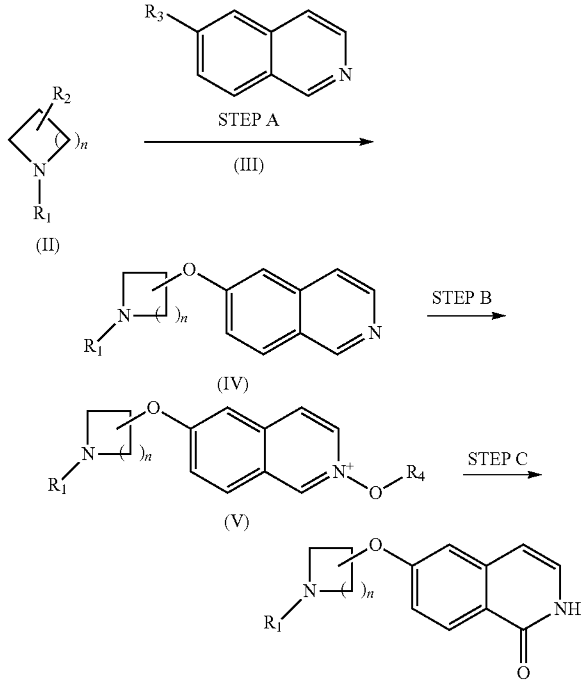

(II) (IV) (V) (I)

Each process step in Scheme 1 can further comprise an optional step of forming a salt of compounds of formula (I), compounds of formula (IV), and compounds of formula (V).

Compounds of formula (I) and salts thereof may exist in lactam form and/or as a tautomeric lactim form, as shown below:

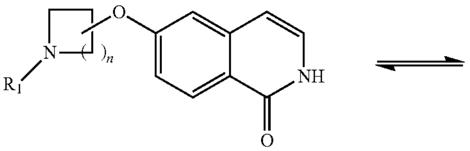

(I)
Lactam Form

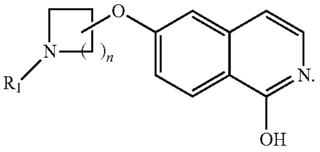

(I)
Lactim Form

DETAILED DESCRIPTION OF THE INVENTION

Process steps to make substituted 6-substituted isoquinoline oxide compounds of formula (V) and to use them as intermediates in the preparation of a compound of formula (I) are described in more detail below.

In one embodiment, the present invention relates to a process for the preparation of a compound of formula (V)

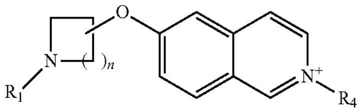

(V)

comprising a step A, reacting a compound of formula (II)

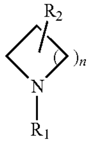

(II)

with a compound of formula (III)

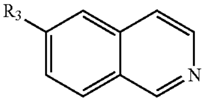

(III)

to produce a compound of formula (IV)

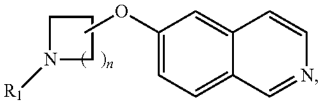

(IV)

wherein $R_1$ is H, a $C_1$-$C_6$ alkyl group, or a protecting group selected from a variety of groups, including but not limited to those mentioned in Greene, Chapter 7: Protection for the Amino Group. Reference is also made to WO 2009/080335 where suitable groups in connection with the synthesis of compounds of formula (I) have been described;

n is 1, 2, 3, or 4;

$R_2$ is —OH or $L_1$, a leaving group that is capable of being substituted by a nucleophile and may be selected from a variety of groups, including but not limited to weak bases;

$R_3$ is —OH or $L_2$, a leaving group that is capable of being substituted by a nucleophile and may be selected from a variety of groups, including but not limited to weak bases;

$R_4$ is selected from the group consisting of —OH; —O—; sulfonates such as p-toluenesulfonate (-TsO) or methanesulfonate (-MsO); perfluoroalkylsulfonates such as trifluoromethanesulfonate (—$CF_3SO_3$); and mixtures thereof.

Step A is shown below.

Step A

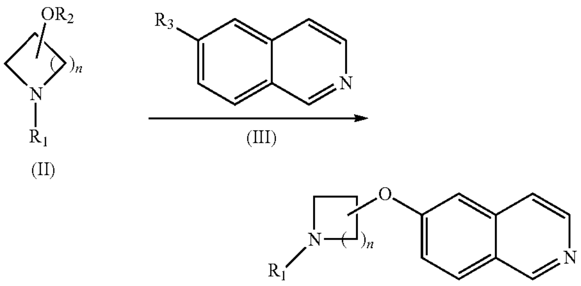

(II) (III) (IV)

Preferably, $R_1$ is a protecting group. The protecting group in $R_1$ is preferably one which is stable under the reaction conditions used in steps A, B, and C. Suitable protecting groups $R_1$ may be selected from N-alkylenearyls, such as a benzyl (Bn) group, a (diphenyl)methylene group, a trityl (triphenylmethyl, Tr) group, or a (4-methoxyphenyl)diphenylmethylene (methoxytrityl, MMT) group; amides, such as a formyl group, an acetyl (Ac) group, or a benzoyl (Bz) group; carbamates, such as a tert-butyloxycarbonyl (BOC) group, a carbobenzyloxy (Cbz) group, a p-methoxybenzylcarbonyl (Moz) group, or a 9-fluorenylmethyloxycarbonyl (Fmoc) group; and N—P and N-sulfonyl protecting groups, such as a dialkyl phosphoramidate group, a methanesulfonyl (mesyl, Ms) group, or a p-toluenesulfonyl (tosyl, Ts) group.

The protecting group in $R_1$ can be introduced by methods known in the art whereby a compound of formula (II), wherein $R_1$ is H, is reacted with a corresponding protecting group-providing reagent to deliver a protected amine. The protecting group may be introduced in a compound of formula (IV), if $R_1$ is H, by reacting the compound of formula (IV) with a corresponding protecting group-providing reagent to deliver a protected amine. The protecting group may be introduced in a compound of formula (V), if $R_1$ is H, by reacting the compound of formula (IV) with a corresponding protecting group-providing reagent to deliver a protected amine. Suitable reagents to be used for introducing the protecting group are known in the art and are commercially available. For example, di-tert-butyl-dicarbonate may be used for introducing a tert-butyloxycarbonyl (BOC) group.

Preferably, the same protecting group $R_1$ is used throughout the synthesis shown in Scheme 1. Accordingly, a protecting group $R_1$ is preferably used in steps A, B, and C.

Most suitable are base stable but acid labile protecting groups, such as a trityl (triphenylmethyl, Tr) group, a (4-methoxyphenyl)diphenylmethylene (methoxytrityl, MMT) group, a tert-butyloxycarbonyl (BOC) group, or a p-toluenesulfonyl (tosyl, Ts) group.

Preferably, $R_1$ is a $C_1$-$C_6$ alkyl group.

The $C_1$-$C_6$ alkyl group in $R_1$ can be introduced by methods known in the art whereby a compound of formula (II), wherein $R_1$ is H, is reacted with a corresponding alkylating reagent to deliver an amine that is alkylated with a $C_1$-$C_6$ alkyl group. In another embodiment, the $C_1$-$C_6$ alkyl group may be introduced in a compound of formula (IV), if $R_1$ is H, by reacting the compound of formula (IV) with a corresponding alkylating reagent to deliver an amine that is alkylated with a $C_1$-$C_6$ alkyl group. In another embodiment, the $C_1$-$C_6$ alkyl group may be introduced in a compound of formula (V), if $R_1$ is H, by reacting the compound of formula (IV) with a corresponding alkylating reagent to deliver an amine that is alkylated with a $C_1$-$C_6$ alkyl group. Suitable reagents to be used for introducing the $C_1$-$C_6$ alkyl group are known in the art and are commercially available. For example, an alkyl halide may be used for introducing a $C_1$-$C_6$alkyl group.

Preferably, the same $C_1$-$C_6$ alkyl group $R_1$ is used throughout the synthesis shown in Scheme 1. Accordingly, the same $C_1$-$C_6$ alkyl group $R_1$ is preferably used in steps A, B, and C.

The leaving group $L_1$ is capable of being substituted by a nucleophile and may be selected from a variety of groups, including but not limited to weak bases. Suitable leaving groups $L_1$ may be selected from halides, such as fluoride (—F), chloride (—Cl), bromide (—Br), or iodide (—I); sulfonates such as p-toluenesulfonate (-TsO) or methanesulfonate (-MsO); perfluoroalkylsulfonates such as trifluoromethanesulfonate (—$CF_3SO_3$); nitrate (—$ONO_2$); and phosphates (—$OPO(OR_2)$, wherein R may be an alkyl group).

The leaving group $L_2$ is capable of being substituted by a nucleophile and may be selected from a variety of groups, including but not limited to weak bases. Suitable leaving groups $L_2$ may be selected from halides, such as fluoride (—F), chloride (—Cl), bromide (—Br), or iodide (—I); sulfonates such as p-toluenesulfonate (-TsO) or methanesulfonate (-MsO); perfluoroalkylsulfonates such as trifluoromethanesulfonate (—$CF_3SO_3$); nitrate (—$ONO_2$); and phosphates (—$OPO(OR_2)$, wherein R may be an alkyl group).

The leaving group $L_1$ can be introduced by methods known in the art whereby a compound of formula (II), wherein $R_2$ is —OH, is reacted with a corresponding leaving group-providing reagent to deliver a leaving group $L_1$.

The leaving group $L_2$ can be introduced by methods known in the art whereby a compound of formula (III), wherein $R_3$ is —OH, is reacted with a corresponding leaving group-providing reagent to deliver a leaving group $L_2$.

Suitable reagents to be used for introducing the leaving group are known in the art and are commercially available. For example, methanesulfonyl chloride (MsCl) may be used for introducing a methanesulfonate (-OMs) leaving group.

Preferably, $R_1$ is H or a protecting group as defined above.

Preferably, $R_1$ is a protecting group as defined above.

Preferably, $R_1$ is a protecting group selected from the group consisting of a trityl (triphenylmethyl, Tr) group, a (4-methoxyphenyl)diphenylmethylene (methoxytrityl, MMT) group, a tert-butyloxycarbonyl (BOC) group, and a p-toluenesulfonyl (tosyl, Ts) group.

Preferably, $R_1$ is a tert-butyloxycarbonyl (BOC) group.

Preferably, $R_1$ is a $C_1$-$C_6$ alkyl group.

Preferably, $R_1$ is methyl, ethyl, n-propyl, isopropyl, n-butyl, sec-butyl, or tert-butyl.

Preferably, $R_2$ is —OH or $L_1$, wherein $L_1$ is selected from the group consisting of chloride (—Cl), bromide (—Br), iodide (—I), p-toluenesulfonate (-TsO), methanesulfonate (-MsO), and trifluoromethanesulfonate (—$CF_3SO_3$).

Preferably, $R_2$ is $L_1$, wherein $L_1$ is selected from the group consisting of chloride (—Cl), bromide (—Br), iodide (—I), p-toluenesulfonate (-TsO), methanesulfonate (-MsO), and trifluoromethanesulfonate (—$CF_3SO_3$).

Preferably, $R_3$ is —OH or $L_2$, wherein $L_2$ is selected from the group consisting of chloride (—Cl), bromide (—Br), iodide (—I), p-toluenesulfonate (-TsO), methanesulfonate (-MsO), and trifluoromethanesulfonate (—$CF_3SO_3$).

Preferably, $R_3$ is —OH.

Preferably, n is 1, 2, or 3.

Preferably, n is 2 or 3.

Preferably, n is 3.

Preferably, step A comprises reacting a compound of formula (II) with a compound of formula (III) in the presence of additional reagents selected from the group consisting of solvents, bases, and mixtures thereof.

Suitable solvents for use in step A may be selected from the group consisting of water, ethers, amides, nitriles, and mixtures thereof.

The solvent used in step A may be an ether selected from the group consisting of diethyl ether, tetrahydrofuran (THF), 2-methyltetrahydrofuran (2-MeTHF), dimethoxyethane (DME), methyl tert-butyl ether (MTBE), 1,4-dioxane, and mixtures thereof.

The solvent used in step A may be an amide selected from the group consisting of dimethylformamide (DMF), dimethylacetamide (DMA), 2-pyrrolidone, and mixtures thereof.

The solvent used in step A may be a nitrile selected from the group consisting of acetonitrile (MeCN), propionitrile, benzonitrile, and mixtures thereof.

Preferably, the solvent is selected from the group consisting of water, diethyl ether, THF, MTBE, DMF, MeCN, and mixtures thereof.

Suitable bases for use in step A may be selected from the group consisting of organic bases, inorganic bases, and mixtures thereof.

The base used in step A may be an organic base selected from the group consisting of amine bases, alkoxide salts, and mixtures thereof.

The base used in step A may be an amine base selected from the group consisting of ammonia, methyl amine, dimethyl amine, trimethyl amine, ethyl amine, diethyl amine, triethyl amine, propyl amine, dipropyl amine, tripropyl amine, isopropyl amine, diisopropyl amine, triisopropyl amine, N,N-diisopropylethylamine, and mixtures thereof.

The base used in step A may be an alkoxide salt selected from the group consisting of lithium methoxide, sodium methoxide, potassium methoxide, lithium ethoxide, sodium ethoxide, potassium ethoxide, lithium tert-butoxide, sodium tert-butoxide, potassium tert-butoxide, and mixtures thereof.

The base used in step A may be an inorganic base selected from the group consisting of hydroxide salts, carbonate salts, bicarbonate salts, and mixtures thereof.

The base used in step A may be a hydroxide salt selected from the group consisting of lithium hydroxide, sodium hydroxide, potassium hydroxide, and mixtures thereof.

The base used in step A may be a carbonate salt selected from the group consisting of lithium carbonate, sodium carbonate, potassium carbonate, cesium carbonate, and mixtures thereof.

The base used in step A may be a bicarbonate salt selected from the group consisting of lithium bicarbonate, sodium bicarbonate, potassium bicarbonate, and mixtures thereof.

Preferably, the base is selected from the group consisting of lithium tert-butoxide, sodium tert-butoxide, potassium tert-butoxide, lithium carbonate, sodium carbonate, potassium carbonate, cesium carbonate, and mixtures thereof.

Preferably, step A is carried out from about 0° C. to about 150° C. Preferably, step A is carried out from about room temperature to about 125° C. Preferably, step A is carried out from about 50° C. to about 110° C. Preferably, step A is carried out from about 55° C. to about 100° C.

Preferably, step A is carried out from about 75° C. to about 105° C. Preferably, step A is carried out at about 100° C. Preferably, step A is carried out at about 90° C. Preferably, step A is carried out at about 65° C. Preferably, step A is carried out at about 55° C. Preferably, step A is carried out from about 50° C. to about 145° C. Preferably, step A is carried out from about 75° C. to about 140° C. Preferably, step A is carried out from about 100° C. to about 135° C. Preferably, step A is carried out at about 130° C.

Preferably, the amount of compound of formula (II) to the amount of compound of formula (III) is in the range of 1 to 5 molar equivalents. Preferably, the range is 1.1 to 4 molar equivalents. Preferably, the range is 1.2 to 3 molar equivalents. Preferably, the range is 1.3 to 2 molar equivalents. Preferably, the range is 1.4 to 1.8 molar equivalents. Preferably, the range is 1.5 to 1.7 molar equivalents. Preferably, the amount of compound of formula (II) to compound of formula (III) is about 1.6 molar equivalents. Preferably, the amount of compound of formula (II) to the amount of compound of formula (III) is in the range of 1 to 2 molar equivalents.

Preferably, the range is 1 to 1.6 molar equivalents. Preferably, the range is 1 to 1.5 molar equivalents. Preferably, the range is 1 to 1.4 molar equivalents. Preferably, the range is 1 to 1.3 molar equivalents. Preferably, the range is 1 to 1.2 molar equivalents. Preferably, the amount of compound of formula (II) to compound of formula (III) is about 1.1 molar equivalents.

Preferably, the amount of compound of formula (II) to the amount of compound of formula (III) is in the range of 1.5 to 3 molar equivalents. Preferably, the range is 1.75 to 2.75 molar equivalents. Preferably, the range is 2 to 2.5 molar equivalents. Preferably, the range is 2.1 to 2.25 molar equivalents. Preferably, the amount of compound of formula (II) to compound of formula (III) is about 2.2 molar equivalents.

Preferably, step A is carried out in the presence of a base and a solvent. Preferably, the base is selected from the group consisting of potassium hydroxide, potassium carbonate, cesium carbonate, potassium tert-butoxide, and mixtures thereof; and the solvent is selected from the group consisting of DMF, water, diethyl ether, MTBE, MeCN, and mixtures thereof. Preferably, the base is selected from the group consisting of potassium hydroxide, potassium carbonate, cesium carbonate, potassium tert-butoxide, and mixtures thereof; and the solvent is selected from the group consisting of DMF, water, MTBE, MeCN, and mixtures thereof. Preferably, the base is selected from the group of potassium hydroxide, potassium carbonate, and cesium carbonate, potassium tert-butoxide, and the solvent is selected from the group consisting of DMF, water, MeCN, and mixtures thereof. Preferably, the base is selected from the group of potassium hydroxide, potassium carbonate, cesium carbonate, and potassium tert-butoxide, and the solvent is DMF or MeCN. Preferably, the base is selected from the group of potassium hydroxide, potassium carbonate, cesium carbonate, and potassium tert-butoxide, and the solvent is a mixture of DMF or MeCN and water. Preferably, the base is potassium hydroxide, and the solvent is DMF. Preferably, the base is potassium hydroxide, and the solvent is a mixture of DMF and water. Preferably, the base is potassium carbonate, and the solvent is DMF. Preferably, the base is potassium carbonate, and the solvent is a mixture of DMF and water. Preferably, the base is cesium carbonate, and the solvent is DMF. Preferably, the base is cesium carbonate, and the solvent is a mixture of DMF and water. Preferably, the base is potassium tert-butoxide, and the solvent is DMF. Preferably, the base is potassium tert-butoxide, and the solvent is a mixture of DMF and water. Preferably, the base is potassium hydroxide, and the solvent is MeCN. Preferably, the base is potassium hydroxide, and the solvent is a mixture of MeCN and water. Preferably, the base is potassium carbonate, and the solvent is MeCN. Preferably, the base is potassium carbonate, and the solvent is a mixture of MeCN and water. Preferably, the base is cesium carbonate, and the solvent is MeCN. Preferably, the base is cesium carbonate, and the solvent is a mixture of MeCN and water. Preferably, the base is potassium tert-butoxide, and the solvent is MeCN. Preferably, the base is potassium tert-butoxide, and the solvent is a mixture of MeCN and water. Preferably, the base is selected from the group of potassium hydroxide, potassium carbonate, and cesium carbonate, potassium tert-butoxide, and the solvent is MTBE. Preferably, the base is potassium hydroxide, and the solvent is MTBE. Preferably, the base is potassium carbonate, and the solvent is MTBE. Preferably, the base is cesium carbonate, and the solvent is MTBE. Preferably, the base is potassium tert-butoxide, and the solvent is MTBE.

Preferably, the amount of base to compound of formula (III) is in the range of 1 to 7 molar equivalents. Preferably, the range is 2 to 6 molar equivalents. Preferably, the range is 3 to 5 molar equivalents. Preferably, the amount of base to compound of formula (III) is about 3 molar equivalents. Preferably, the amount of base to compound of formula (III) is about 4 molar equivalents. Preferably, the amount of base to compound of formula (III) is in the range of 1 to 3 molar equivalents. Preferably, the amount of base to compound of formula (III) is about 1 molar equivalent. Preferably, the amount of base to compound of formula (III) is about 2 molar equivalents. Preferably, the amount of base to compound of formula (III) is about 2.2 molar equivalents. Preferably, the amount of base to compound of formula (III) is in the range of 1 to 1.5 molar equivalents. Preferably, the amount of base to compound of formula (III) is about 1.1 molar equivalents. Preferably, the amount of base to compound of formula (III) is about 1.2 molar equivalents. Preferably, the amount of base to compound of formula (III) is about 1.3 molar equivalents. Preferably, the amount of base to compound of formula (III) is about 1.4 molar equivalents. Preferably, the amount of base to compound of formula (III) is about 1.5 molar equivalents.

Step A can may be conducted using formula (II) or a pharmaceutically acceptable salt thereof and formula (III) or a pharmaceutically acceptable salt thereof.

Examples of Step A are shown in Scheme 2 and Table I below. Scheme 2 provides examples of Step A reactions, and Table I provides reaction conditions used in the reactions shown in Scheme 2:

Scheme 2

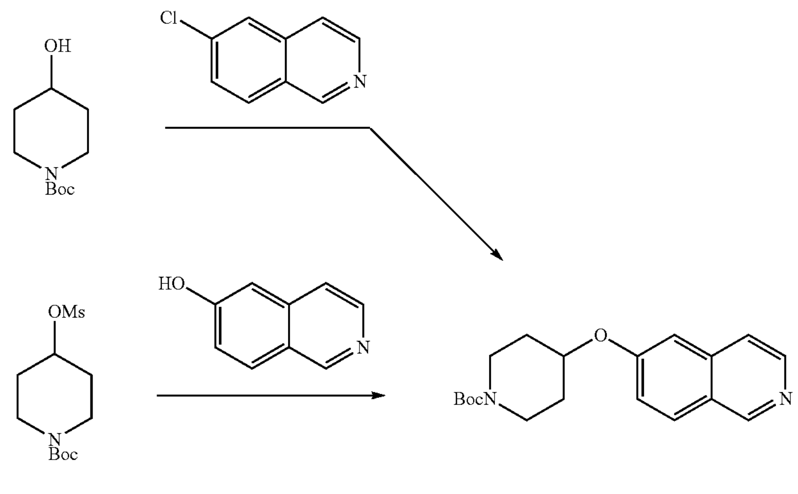

-continued
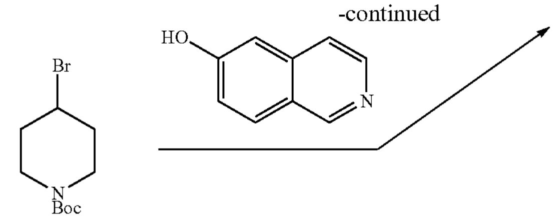

TABLE I

| # | Reactant, Compound of Formula (II) | Reactant, Compound of Formula (III) | Reaction Conditions | Yield % | Purity (area %) |
|---|---|---|---|---|---|
| 1 | 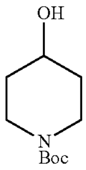 (1.1 eq.) | 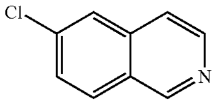 (1.0 eq.) | Reaction scale: 0.8 g<br>Potassium tert-butoxide ($KO_tBu$, 1.3 eq.)<br>MTBE (10 volumes)<br>Reaction suspension was stirred at reflux temperature (55° C.) overnight (16 hours) | N/A (≤2.0% a/a of desired product) | N/A |
| 2 | 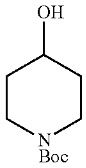 (1.6 eq.) | 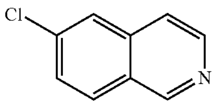 (1.0 eq.) | Reaction scale: 1.0 g<br>Potassium carbonate ($K_2CO_3$, 4 eq.)<br>Dimethylformamide (DMF, 15 volumes)<br>Reaction suspension was stirred at 100° C. for 16 hours | N/A | N/A |
| 3 | 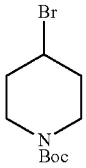 (1.6 eq.) | 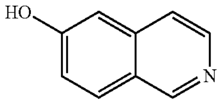 (1.0 eq.) | Reaction scale: 1.0 g<br>$K_2CO_3$ (4 eq.),<br>DMF (15 volumes)<br>Reaction suspension was stirred at 100° C. for 16 hours | N/A (21% a/a of desired product) | N/A |
| 4 | 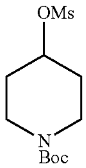 (1.6 eq.) | 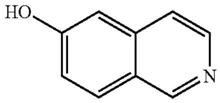 (1.0 eq.) | Reaction scale: 1.0 g<br>$K_2CO_3$ (4 eq.)<br>DMF (15 volumes)<br>Reaction suspension was stirred at 100° C. for 16 hours | 65 (1.47 g) | 99.84 |
| 5 | 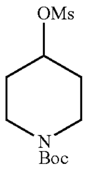 [SMILES: CS(=O)(=O)OC1CCNCC1] (1.6 eq.) | 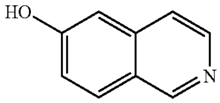 (1.0 eq.) | Reaction scale: 120 g<br>$K_2CO_3$ (4 eq.)<br>DMF (15 volumes)<br>Reaction suspension was stirred at 100° C. for 16 hours | 67 (58.84 g) | 99.92 |
| 6 | 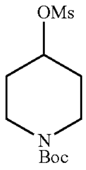 (1.6 eq.) | 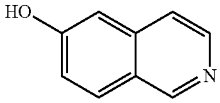 (1.0 eq.) | Reaction scale: 1 g<br>$K_2CO_3$ (3 eq.),<br>DMF (4 volumes),<br>Reaction suspension was stirred at 100° C. for 16 hours | N/A (79.2% a/a of desired product) | N/A |
| 7 | 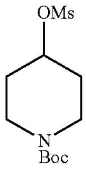 (1.6 eq.) | 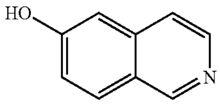 [SMILES: Oc1ccc2cnccc2c1] (1.0 eq.) | Reaction scale: 1 g<br>$K_2CO_3$ (3 eq.),<br>DMF (6 volumes),<br>Reaction suspension was stirred at 100° C. for 16 hours | N/A (68.2% a/a of desired product) | N/A |

TABLE I-continued

| # | Reactant, Compound of Formula (II) | Reactant, Compound of Formula (III) | Reaction Conditions | Yield % | Purity (area %) |
|---|---|---|---|---|---|
| 8 | 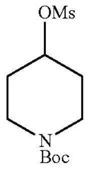 (1.6 eq.) | 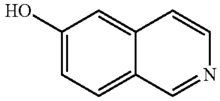 (1.0 eq.) | Reaction scale: 1 g $K_2CO_3$ (3 eq.), DMF (8 volumes), Reaction suspension was stirred at 100° C. for 16 hours | N/A (59.1% a/a of desired product) | N/A |
| 9 | 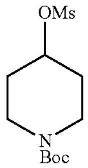 [SMILES: CS(=O)(=O)OC1CCNCC1] (1.6 eq.) | 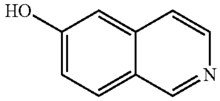 (1.0 eq.) | Reaction scale: 0.5 g $K_2CO_3$ (3 eq.), DMF (10 volumes), Temperature of reaction suspension was gradually raised to 65° C., then was stirred at 65° C. for 20 hours | N/A (66.1% a/a of desired product) | N/A |
| 10 | 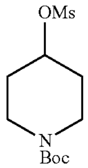 (1.6 eq.) | 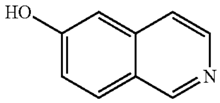 (1.0 eq.) | Reaction scale: 0.5 g $K_2CO_3$ (2 eq.), DMF (9 volumes), $H_2O$ (1 volume), Temperature of reaction suspension was gradually raised to 65° C., then was stirred at 65° C. for 20 hours | N/A (66.3% a/a of desired product) | N/A |
| 11 | 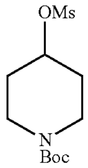 (1.6 eq.) | 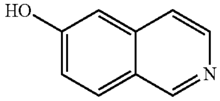 [SMILES: Oc1ccc2cnccc2c1] (1.0 eq.) | Reaction scale: 0.5 g $K_2CO_3$ (2 eq.), DMF (5 volumes), Temperature of reaction suspension was gradually raised to 65° C., then was stirred at 65° C. for 8 hours | N/A (45% a/a of desired product) | N/A |
| 12 | 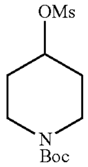 (1.6 eq.) | 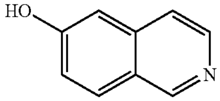 (1.0 eq.) | Reaction scale: 0.5 g $K_2CO_3$ (2 eq.), DMF (4.5 volumes), $H_2O$ (0.5 volumes), Temperature of reaction suspension was gradually raised to 65° C., then was stirred at 65° C. for 20 hours | N/A (44% a/a of desired product) | N/A |
| 13 | 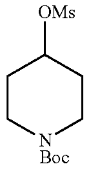 (1.6 eq.) | 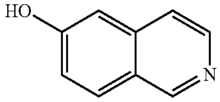 (1.0 eq.) | Reaction scale: 0.5 g KOH aq. 45% (1.1 eq.) DMF (4 volumes), Reaction suspension was stirred at 65° C. overnight | N/A (50% a/a of desired product) | N/A |
| 14 | 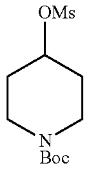 (1.6 eq.) | 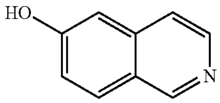 (1.0 eq.) | Reaction scale: 0.5 g $Cs_2CO_3$ (2 eq.), DMF (10 volumes), Reaction suspension was stirred at 65° C. overnight | N/A (95% a/a of desired product) | N/A |

TABLE I-continued

| # | Reactant, Compound of Formula (II) | Reactant, Compound of Formula (III) | Reaction Conditions | Yield % | Purity (area %) |
|---|---|---|---|---|---|
| 15 | 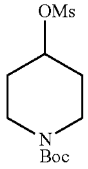 (1.6 eq.) | 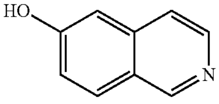 (1.0 eq.) | Reaction scale: 0.2 g $Cs_2CO_3$ (2 eq.), DMF (5 volumes), $H_2O$ (1 volume) Reaction suspension was stirred at 65° C. overnight | N/A (73% a/a of desired product) | N/A |
| 16 | 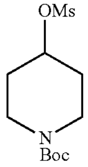 (1.6 eq.) | 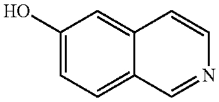 (1.0 eq.) | Reaction scale: 0.2 g $Cs_2CO_3$ (2 eq.), DMF (5 volumes), $H_2O$ (2 volumes) Reaction suspension was stirred at 65° C. overnight | N/A (74% a/a of desired product) | N/A |
| 17 | 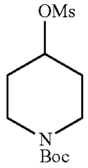 (1.6 eq.) | 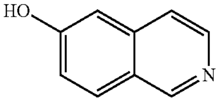 (1.0 eq.) | Reaction scale: 0.2 g $Cs_2CO_3$ (2 eq.), DMF (5 volumes), $H_2O$ (1 volume) Reaction suspension was stirred at 90° C. overnight | 53 | 99.23 |
| 18 | 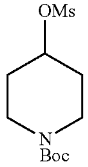 (1.6 eq.) | 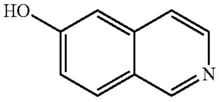 (1.0 eq.) | Reaction scale: 0.2 g $Cs_2CO_3$ (2 eq.), DMF (5 volumes), $H_2O$ (2 volumes) Reaction suspension was stirred at 90° C. overnight | N/A (80% a/a of desired product) | N/A |
| 19 | 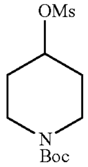 (1.6 eq.) | 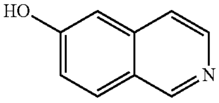 (1.0 eq.) | Reaction scale: 15 g $Cs_2CO_3$ (2 eq.), DMF (5 volumes), $H_2O$ (2 volumes) Reaction suspension was stirred at 90° C. overnight | 72 | 99.8 |
| 20 | 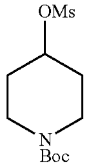 (1.6 eq.) | 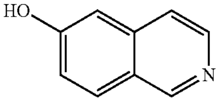 (1.0 eq.) | Reaction scale: 10 g $Cs_2CO_3$ (2 eq.), DMF (5 volumes), $H_2O$ (1 volume) Reaction suspension was stirred at 90° C. overnight | 69 | 98.2 |
| 21 | 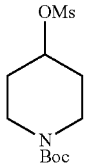 (1.6 eq.) | 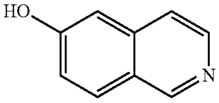 (1.0 eq.) | Reaction scale: 10 g $Cs_2CO_3$ (2 eq.), DMF (5 volumes), $H_2O$ (1 volume) Reaction suspension was stirred at 90° C. overnight | 66 (13.3 g) | 99.6 |

TABLE I-continued

| # | Reactant, Compound of Formula (II) | Reactant, Compound of Formula (III) | Reaction Conditions | Yield % | Purity (area %) |
|---|---|---|---|---|---|
| 22 | 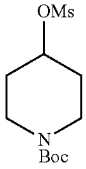 (1.6 eq.) | 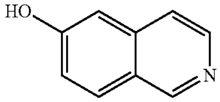 (1.0 eq.) | Reaction scale: 55 g (quantified by NMR to be 49 g) $Cs_2CO_3$ (2 eq.), DMF (5 volumes), $H_2O$ (1 volume) Reaction suspension was stirred at 90° C. overnight | 84 (92.8 g) | 99.4 |
| 23 | 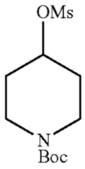 (1.2 eq. + 1.0 eq.) | 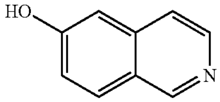 (1.0 eq.) | Reaction scale: 5 g After an initial charge of 1-Boc-4-mesylate piperidine (compound of formula (II), 1.2 eq.), an additional charge (1.0 eq.) was added to the reaction suspension (2.2 eq. total 1-Boc-4-mesylate piperidine) After an initial charge of $Cs_2CO_3$ (1.2 eq.), an additional charge of $Cs_2CO_3$ (1.0 eq.) was added (2.2 eq. $Cs_2CO_3$ total) DMF (5 volumes), $H_2O$ (1 volume), Reaction suspension was stirred at 90° C. overnight | 97 (11.72 g) | 98.09 |
| 24 | 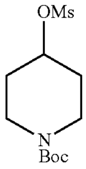 (1.6 eq.) | 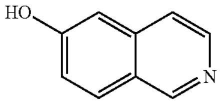 (1.0 eq.) | Reaction scale: 5 g $Cs_2CO_3$ (2.5 eq.), DMF (5 volumes), $H_2O$ (1 volume), Reaction suspension was stirred at 90° C. for 16 hours | 74 (8.25 g) | 98.5 |
| 25 | 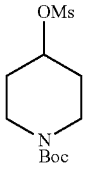 (1.4 eq. + 0.35 eq. + 0.25 eq.) | 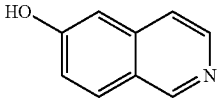 (1.0 eq.) | Reaction scale: 11.5 g $Cs_2CO_3$ (2.5 eq.), DMF (5 volumes), $H_2O$ (1 volume), Reaction suspension was stirred at 90° C. for 16 hours After an initial charge of 1-Boc-4-mesylate piperidine (compound of formula (II), 1.4 eq.), two additional charges were added. After the first additional charge (0.35 eq.), the reaction suspension was stirred overnight. After the second additional charge (0.25 eq.), the reaction suspension was stirred overnight. (2.2 eq. total 1-Boc-4-mesylate piperidine) | 90 (23.3 g) | 98.4 |
| 26 | 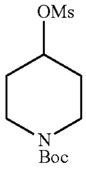 | 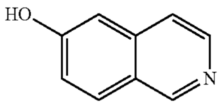 | Amount of compound of formula (II) used: 7.75 g $K_2CO_3$ DMF Reaction suspension was stirred at 100° C. for 19 hours | 66.4 (7.5 g) | N/A |
| 27 | 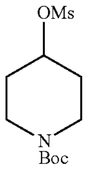 | 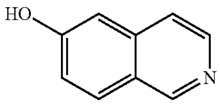 | Amount of compound of formula (II) used: 4.10 g $K_2CO_3$ MeCN Reaction suspension was stirred at 80° C. for 21 hours | 18.2 (0.57 g) | N/A |

TABLE I-continued

| # | Reactant, Compound of Formula (II) | Reactant, Compound of Formula (III) | Reaction Conditions | Yield % | Purity (area %) |
|---|---|---|---|---|---|
| 28 | 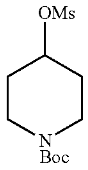 (1.55 eq.) | 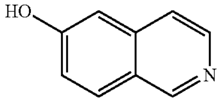 (1.0 eq.) | Reaction scale: 7 g $Cs_2CO_3$ (4 eq.) MeCN (115.50 mL), Reaction suspension was stirred at 80° C. for 21 hours | 76.8 (12.10 g) | 98.5 |
| 29 | 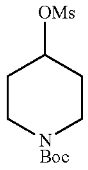 (1.6 eq.) | 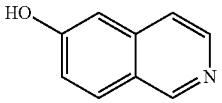 (1.0 eq.) | Reaction scale: 100 g $Cs_2CO_3$ (2.5 eq.), DMF (5 volumes), $H_2O$ (1 volume), Reaction suspension was stirred at 90° C. for 16 hours | 85% (192 g) | 99.7 |
| 30 | 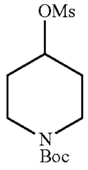 (1.6 eq.) | 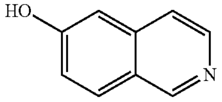 (1.0 eq.) | Reaction scale: 780 g $Cs_2CO_3$ (2.5 eq.), DMF (5 volumes), $H_2O$ (1 volume), Reaction suspension was stirred at 90° C. for 16 hours | 84% (1477 g) | 99.9 |

The process for the preparation of a compound of formula (V) further comprises a step B, reacting a compound of formula (IV)

(IV)

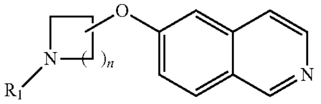

to produce a compound of formula (V)

(V)

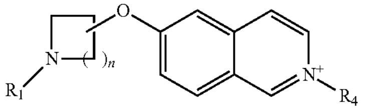

wherein $R_1$ is H, a $C_1$-$C_6$ alkyl group, or a protecting group as defined above, and n is 1, 2, 3, or 4.

Step B is shown below.

Step B

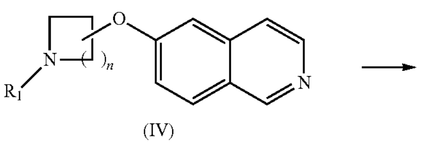

(IV)

-continued

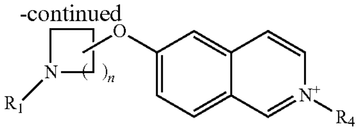

(V)

Preferably, $R_1$ is H or a protecting group as defined above.

Preferably, $R_1$ is a protecting group as defined above.

Preferably, $R_1$ is a protecting group selected from the group consisting of a trityl (triphenylmethyl, Tr) group, a (4-methoxyphenyl)diphenylmethylene (methoxytrityl, MMT) group, a tert-butyloxycarbonyl (BOC) group, and a p-toluenesulfonyl (tosyl, Ts) group.

Preferably, $R_1$ is a tert-butyloxycarbonyl (BOC) group.

Preferably, $R_1$ is a $C_1$-$C_6$ alkyl group.

Preferably, $R_1$ is methyl, ethyl, n-propyl, isopropyl, n-butyl, sec-butyl, or tert-butyl.

Preferably, n is 1, 2, or 3.

Preferably, n is 2 or 3.

Preferably, n is 3.

Preferably, $R_4$ is selected from the group consisting of —OH, —O—, p-toluenesulfonate (-TsO), methanesulfonate (-MsO), trifluoromethanesulfonate (—$CF_3SO_3$), and mixtures thereof.

Preferably, step B comprises reacting a compound of formula (IV) to form a compound of formula (V) in the presence of additional reagents selected from the group consisting of oxidizing agents, catalysts, solvents, bases, and mixtures thereof.

Suitable oxidizing agents for use in step B may be selected from the group consisting of peroxides; oxiranes; oxygen; ozone; oxone (potassium peroxymonosulfate); halogens; metal oxides; permanganate compounds; and perborate salts.

Preferably, the oxidizing agent used in step B is a peroxide selected from the group consisting of hydrogen peroxide, urea hydrogen peroxide, acetone peroxide, acetyl benzoyl peroxide, benzoyl peroxide, tert-butyl hydroperoxide, diacetyl peroxide, ethyl hydroperoxide, methyl ethyl ketone peroxide, peracetic acid, performic acid, peroxybenzoic acid, meta-chloroperoxybenzoic acid (mCPBA), peroxymonosulfuric acid, peroxynitric acid, peroxymonophosphoric acid, sodium percarbonate ($Na_2CO_3 \cdot 1.5H_2O_2$), and mixtures thereof.

Preferably, the oxidizing agent used in step B is an oxirane selected from the group consisting of dimethyldioxirane, difluorodioxirane, methyl(trifluoromethyl)dioxirane, 3,3-bis(trifluoromethyl)dioxirane, and mixtures thereof.

Preferably, the oxidizing agent used in step B is oxone.

Preferably, the oxidizing agent used in step B is a permanganate compound. Preferably, the oxidizing agent used in step B is potassium permanganate.

Preferably, the oxidizing agent used in step B is a perborate salt selected from the group consisting of lithium perborate, sodium perborate, potassium perborate, and mixtures thereof.

The perborate salts may be in the form of a hydrate, such as sodium perborate tetrahydrate.

Preferably, the oxidizing agent used in step B is selected from the group consisting of hydrogen peroxide, urea hydrogen peroxide, acetone peroxide, sodium percarbonate, peracetic acid, performic acid, peroxybenzoic acid, mCPBA, dimethyldioxirane, oxone, peroxymonosulfuric acid, peroxynitric acid, peroxymonophosphoric acid, sodium perborate, and mixtures thereof.

Suitable catalysts for use in step B may be selected from the group consisting of organic, inorganic, and organometallic catalysts.

Preferably, catalysts for use in step B are selected from the group consisting of organometallic catalysts, such as methyltrioxorhenium (VII) (MeReO3, also abbreviated as MTO); organic acids, such as acetic acid, formic acid, trifluoroacetic acid, and mixtures thereof; inorganic acids, such as phosphomolybdic acid (PMA); and mixtures thereof.

Suitable solvents for use in step B may be selected from the group consisting of halogenated alkanes, nitriles, alcohols, organic acids, and mixtures thereof.

Solvents for use in step B may be halogenated alkanes selected from the group consisting of dichloromethane (DCM), chloroform, carbon tetrachloride, 1,2-dichloroethane, and mixtures thereof.

Solvents for use in step B may be nitriles selected from the group consisting of MeCN, propionitrile, benzonitrile, and mixtures thereof.

Solvents for use in step B may be alcohols selected from the group consisting of methanol, ethanol, n-propanol, isopropanol, n-butanol (1-BuOH), sec-butanol, isobutanol, tert-butanol, and mixtures thereof.

Solvents for use in step B may be organic acids selected from the group consisting of acetic acid, formic acid, trifluoroacetic acid, and mixtures thereof.

Suitable bases for use in step B are inorganic bases.

Bases for use in step B may be selected from the group consisting of hydroxide salts, bicarbonate salts, and carbonate salts.

The base used in step B may be a hydroxide salt selected from the group consisting of lithium hydroxide, sodium hydroxide, potassium hydroxide, and mixtures thereof.

The base used in step B may be a bicarbonate salt selected from the group consisting of lithium bicarbonate, sodium bicarbonate, potassium bicarbonate, and mixtures thereof.

The base used in step B may be a carbonate salt selected from the group consisting of lithium carbonate, sodium carbonate, potassium carbonate, cesium carbonate, and mixtures thereof.

Preferably, step B is carried out from about −10° C. to about 50° C. Preferably, step B is carried out from about −5° C. to about 40° C. Preferably, step B is carried out from about 0° C. to about 30° C. Preferably, step B is carried out from about 5° C. to about 30° C. Preferably, step B is carried out from about 0° C. to about 25° C. Preferably, step B is carried out from about 5° C. to about 25° C. Preferably, step B is carried out from about 0° C. to about 20° C. Preferably, step B is carried out from about 5° C. to about 20° C. Preferably, step B is carried out from about 0° C. to about 15° C. Preferably, step B is carried out from about 5° C. to about 15° C. Preferably, step B is carried out from about 0° C. to about 10° C. Preferably, step B is carried out from about 5° C. to about 10° C.

Preferably, step B is carried out from about 25° C. to about 150° C. Preferably, step B is carried out from about 30° C. to about 135° C. Preferably, step B is carried out from about 35° C. to about 120° C. Preferably, step B is carried out from about 40° C. to about 105° C. Preferably, step B is carried out from about 45° C. to about 100° C. Preferably, step B is carried out from about 45° C. to about 95° C. Preferably, step B is carried out from about 45° C. to about 90° C.

Preferably, step B is carried out from about 45° C. to about 80° C. Preferably, step B is carried out from about 45° C. to about 70° C. Preferably, step B is carried out from about 45° C. to about 60° C. Preferably, step B is carried out from about 45° C. to about 55° C. Preferably, step B is carried out from about 55° C. to about 75° C. Preferably, step B is carried out from about 55° C. to about 70° C. Preferably, step B is carried out from about 55° C. to about 65° C. Preferably, step B is carried out from about 65° C. to about 95° C. Preferably, step B is carried out from about 70° C. to about 90° C. Preferably, step B is carried out from about 75° C. to about 85° C.

Preferably, step B is carried out from about 80° C. to about 90° C. Preferably, step B is carried out at about 50° C. Preferably, step B is carried out at about 55° C. Preferably, step B is carried out at about 60° C. Preferably, step B is carried out at about 65° C. Preferably, step B is carried out at about 70° C. Preferably, step B is carried out at about 75° C. Preferably, step B is carried out at about 80° C. Preferably, step B is carried out at about 85° C. Preferably, step B is carried out at about 90° C.

Preferably, step B is carried out in the presence of an oxidizing agent. Preferably, the oxidizing agent used in step B is a peroxide selected from the group consisting of peracetic acid, performic acid, and mixtures thereof.

Preferably, step B is carried out in the presence of an oxidizing agent and a solvent. Preferably, the oxidizing agent used in step B is selected from the group consisting of hydrogen peroxide, urea hydrogen peroxide, sodium percarbonate, peracetic acid, performic acid, sodium perborate, and mixtures thereof; and the solvent is selected from the group consisting of MeCN, ethanol, acetic acid, DCM, chloroform, and mixtures thereof. Preferably, the oxidizing agent is selected from the group consisting of mCPBA, hydrogen peroxide, urea hydrogen peroxide, sodium percarbonate, sodium perborate, and mixtures thereof; and the solvent is selected from the group consisting of MeCN, ethanol, acetic acid, DCM, and mixtures thereof. Preferably, the oxidizing agent is selected from the group consisting of mCPBA, hydrogen peroxide, urea hydrogen peroxide, sodium percarbonate, and sodium perborate; and the solvent is selected from the group consisting of MeCN, ethanol, acetic acid, and DCM. Preferably, the oxidizing agent is sodium perborate and the solvent is acetic acid. Preferably, the oxidizing agent is hydrogen peroxide and the solvent is acetic acid. Preferably, the oxidizing agent is urea hydrogen peroxide and the solvent is acetic acid. Preferably, the oxidizing agent is sodium perborate and the solvent is MeCN. Preferably, the oxidizing agent is hydrogen peroxide and the solvent is MeCN. Preferably, the oxidizing agent is urea hydrogen peroxide and the solvent is MeCN. Preferably, the oxidizing agent mCPBA and the solvent is MeCN. Preferably, the oxidizing agent is sodium perborate and the solvent is ethanol. Preferably, the oxidizing agent is hydrogen peroxide and the solvent is ethanol. Preferably, the oxidizing agent is urea hydrogen peroxide and the solvent is ethanol. Preferably, the oxidizing agent mCPBA and the solvent is ethanol. Preferably, the oxidizing agent is hydrogen peroxide and the solvent is DCM. Preferably, the oxidizing agent is urea hydrogen peroxide and the solvent is DCM. Preferably, the oxidizing agent is mCPBA and the solvent is DCM.

Preferably, step B is carried out in the presence of an oxidizing agent, a catalyst, and a solvent. Preferably, the oxidizing agent used in step B is selected from the group consisting of hydrogen peroxide, urea hydrogen peroxide, sodium percarbonate, peracetic acid, performic acid, sodium perborate, mCPBA, and mixtures thereof; the solvent is selected from the group consisting of MeCN, ethanol, acetic acid, DCM, chloroform, and mixtures thereof; and the catalyst is selected from the group consisting of acetic acid, trifluoroacetic acid, formic acid, MTO, PMA, and mixtures thereof. Preferably, the oxidizing agent used in step B is selected from the group consisting of hydrogen peroxide, urea hydrogen peroxide, sodium percarbonate, peracetic acid, performic acid, sodium perborate, and mixtures thereof; the solvent is selected from the group consisting of MeCN, ethanol, DCM, and mixtures thereof; and the catalyst is selected from the group consisting of acetic acid, formic acid, MTO, PMA, and mixtures thereof. Preferably, the oxidizing agent used in step B is selected from the group consisting of hydrogen peroxide, urea hydrogen peroxide, sodium percarbonate, and mixtures thereof; the solvent is selected from the group consisting of MeCN, ethanol, DCM, and mixtures thereof; and the catalyst is selected from the group consisting of acetic acid, formic acid, MTO, PMA, and mixtures thereof. Preferably, the oxidizing agent used in step B is selected from the group consisting of hydrogen peroxide, urea hydrogen peroxide, sodium percarbonate, and mixtures thereof; the solvent is MeCN or MeCN; and the catalyst is selected from the group consisting of acetic acid, MTO, PMA, and mixtures thereof. Preferably, the oxidizing agent is hydrogen peroxide or urea hydrogen peroxide, the solvent is DCM, and the catalyst is MTO or PMA. Preferably, the oxidizing agent is hydrogen peroxide or urea hydrogen peroxide, the solvent is MeCN, and the catalyst is MTO or PMA. Preferably, the oxidizing agent is hydrogen peroxide; the catalyst is PMA; and the solvent is MeCN. Preferably, the oxidizing agent is urea hydrogen peroxide; the catalyst is PMA; and the solvent is MeCN. Preferably, the oxidizing agent is hydrogen peroxide; the catalyst is MTO; and the solvent is MeCN. Preferably, the oxidizing agent is urea hydrogen peroxide; the catalyst is MTO; and the solvent is MeCN. Preferably, the oxidizing agent is sodium percarbonate; the catalyst is MTO, acetic acid, and mixtures thereof; and the solvent is MeCN. Preferably, the oxidizing agent is hydrogen peroxide or urea hydrogen peroxide, the solvent is ethanol, and the catalyst is MTO or PMA. Preferably, the oxidizing agent is hydrogen peroxide; the catalyst is PMA; and the solvent is ethanol. Preferably, the oxidizing agent is urea hydrogen peroxide; the catalyst is PMA; and the solvent is ethanol. Preferably, the oxidizing agent is hydrogen peroxide; the catalyst is MTO; and the solvent is ethanol. Preferably, the oxidizing agent is urea hydrogen peroxide; the catalyst is MTO; and the solvent is ethanol. Preferably, the oxidizing agent is sodium percarbonate; the catalyst is MTO, acetic acid, and mixtures thereof; and the solvent is ethanol.

Preferably, step B is carried out in the presence of an oxidizing agent, a catalyst, a base, and a solvent. Preferably, the oxidizing agent used in step B is selected from the group consisting of hydrogen peroxide, urea hydrogen peroxide, sodium percarbonate, peracetic acid, performic acid, sodium perborate, mCPBA, and mixtures thereof; the solvent is selected from the group consisting of MeCN, ethanol, acetic acid, DCM, chloroform, and mixtures thereof; the catalyst is selected from the group consisting of acetic acid, formic acid, trifluoroacetic acid, MTO, PMA, and mixtures thereof; and the base is selected from the group consisting of lithium bicarbonate, sodium bicarbonate, potassium bicarbonate, lithium carbonate, sodium carbonate, potassium carbonate, cesium carbonate, and mixtures thereof. Preferably, the oxidizing agent used in step B is selected from the group consisting of hydrogen peroxide, urea hydrogen peroxide, sodium percarbonate, and mixtures thereof; the solvent is selected from the group consisting of MeCN, ethanol, DCM, and mixtures thereof; the catalyst is selected from the group consisting of acetic acid, formic acid, trifluoroacetic acid, MTO, PMA, and mixtures thereof; and the base is selected from the group consisting of lithium bicarbonate, sodium bicarbonate, potassium bicarbonate, lithium carbonate, sodium carbonate, potassium carbonate, cesium carbonate, and mixtures thereof. Preferably, the oxidizing agent used in step B is selected from the group consisting of hydrogen peroxide, urea hydrogen peroxide, sodium percarbonate, and mixtures thereof; the solvent is selected from the group consisting of MeCN, ethanol, DCM, and mixtures thereof; the catalyst is selected from the group consisting of acetic acid, formic acid, trifluoroacetic acid, MTO, PMA, and mixtures thereof; and the base is selected from the group consisting of sodium bicarbonate, sodium carbonate, and mixtures thereof. Preferably, the oxidizing agent used in step B is selected from the group consisting of hydrogen peroxide, urea hydrogen peroxide, sodium percarbonate, and mixtures thereof; the solvent is selected from the group consisting of MeCN, ethanol, DCM, and mixtures thereof; the catalyst is selected from the group consisting of acetic acid, MTO, PMA, and mixtures thereof; and the base is selected from the group consisting of sodium bicarbonate, sodium carbonate, and mixtures thereof. Preferably, the oxidizing agent used in step B is selected from the group consisting of hydrogen peroxide, urea hydrogen peroxide, sodium percarbonate, and mixtures thereof; the solvent is MeCN; the catalyst is selected from the group consisting of acetic acid, MTO, and mixtures thereof; and the base is selected from the group consisting of sodium bicarbonate, sodium carbonate, and mixtures thereof. Preferably, the oxidizing agent used in step B is hydrogen peroxide; the solvent is MeCN; the catalyst is a mixture of acetic acid and MTO; and the base is sodium bicarbonate. Preferably, the oxidizing agent used in step B is hydrogen peroxide; the solvent is MeCN; the catalyst is a mixture of acetic acid and MTO; and the base is sodium carbonate. Preferably, the oxidizing agent used in step B is urea hydrogen peroxide; the solvent is MeCN; the catalyst is a mixture of acetic acid and MTO; and the base is sodium bicarbonate. Preferably, the oxidizing agent used in step B is urea hydrogen peroxide; the solvent is MeCN; the catalyst is a mixture of acetic acid and MTO; and the base is sodium carbonate. Preferably, the oxidizing agent used in step B is hydrogen peroxide; the solvent is MeCN; the catalyst is MTO; and the base is sodium bicarbonate. Preferably, the oxidizing agent used in step B is hydrogen peroxide; the solvent is MeCN; the catalyst is MTO; and the base is sodium carbonate. Preferably, the oxidizing agent used in step B is urea hydrogen peroxide; the solvent is MeCN; the catalyst is MTO; and the base is sodium bicarbonate. Preferably, the oxidizing agent used in step B is urea hydrogen peroxide; the solvent is MeCN; the catalyst is MTO; and the base is sodium carbonate. Preferably, the oxidizing agent used in step B is selected from the group consisting of hydrogen peroxide, urea hydrogen peroxide, sodium percarbonate, and mixtures thereof; the solvent is ethanol; the catalyst is selected from the group consisting of acetic acid, MTO, and mixtures thereof; and the base is selected from the group consisting of sodium bicarbonate, sodium carbonate, and mixtures thereof. Preferably, the oxidizing agent used in step B is hydrogen peroxide; the solvent is ethanol; the catalyst is a mixture of acetic acid and MTO; and the base is sodium bicarbonate. Preferably, the oxidizing agent used in step B is hydrogen peroxide; the solvent is ethanol; the catalyst is a mixture of acetic acid and MTO; and the base is sodium carbonate. Preferably, the oxidizing agent used in step B is urea hydrogen peroxide; the solvent is ethanol; the catalyst is a mixture of acetic acid and MTO; and the base is sodium bicarbonate. Preferably, the oxidizing agent used in step B is urea hydrogen peroxide; the solvent is ethanol; the catalyst is a mixture of acetic acid and MTO; and the base is sodium carbonate. Preferably, the oxidizing agent used in step B is hydrogen peroxide; the solvent is ethanol; the catalyst is MTO; and the base is sodium bicarbonate. Preferably, the oxidizing agent used in step B is hydrogen peroxide; the solvent is ethanol; the catalyst is MTO; and the base is sodium carbonate. Preferably, the oxidizing agent used in step B is urea hydrogen peroxide; the solvent is ethanol; the catalyst is MTO; and the base is sodium bicarbonate. Preferably, the oxidizing agent used in step B is urea hydrogen peroxide; the solvent is ethanol; the catalyst is MTO; and the base is sodium carbonate.

Preferably, the amount of oxidizing agent to compound of formula (IV) is in the range of 1 to 10 molar equivalents. Preferably, the range is 1 to 8 molar equivalents. Preferably, the range is 1.1 to 7.5 molar equivalents. Preferably, the range is 1.2 to 6 molar equivalents. Preferably, the range is 1.25 to 5 molar equivalents. Preferably, the range is 1.3 to 4 molar equivalents. Preferably, the range is 1.4 to 3 molar equivalents. Preferably, the range is 1.5 to 2 molar equivalents. Preferably, the range is 1.6 to 1.9 molar equivalents. Preferably, the amount of oxidizing agent to compound of formula (IV) is about 1.5 molar equivalents. Preferably, the amount of oxidizing agent to compound of formula (IV) is about 1.8 molar equivalents. Preferably, the amount of oxidizing agent to compound of formula (IV) is about 2 molar equivalents. Preferably, the amount of oxidizing agent to compound of formula (IV) is about 2.2 molar equivalents. Preferably, the amount of oxidizing agent to compound of formula (IV) is about 2.5 molar equivalents. Preferably, the amount of oxidizing agent to compound of formula (IV) is about 2.8 molar equivalents. Preferably, the amount of oxidizing agent to compound of formula (IV) is about 3 molar equivalents. Preferably, the amount of oxidizing agent to compound of formula (IV) is about 3.2 molar equivalents. Preferably, the amount of oxidizing agent to compound of formula (IV) is about 4 molar equivalents. Preferably, the amount of oxidizing agent to compound of formula (IV) is about 5 molar equivalents. Preferably, the amount of oxidizing agent to compound of formula (IV) is about 6 molar equivalents. Preferably, the amount of oxidizing agent to compound of formula (IV) is about 7 molar equivalents. Preferably, the amount of oxidizing agent to compound of formula (IV) is about 7.5 molar equivalents.

Preferably, the amount of catalyst to compound of formula (IV) is in the range of 0.001 to 1 molar equivalents. Preferably, the range is 0.05 to 0.5 molar equivalents. Preferably, the range is 0.01 to 0.5 molar equivalents. Preferably, the amount of catalyst to compound of formula (IV) is about 0.005 molar equivalents. Preferably, the amount of catalyst to compound of formula (IV) is about 0.01 molar equivalents. Preferably, the amount of catalyst to compound of formula (IV) is about 0.02 molar equivalents. Preferably, the amount of catalyst to compound of formula (IV) is about 0.03 molar equivalents. Preferably, the amount of catalyst to compound of formula (IV) is about 0.1 molar equivalents. Preferably, the amount of catalyst to compound of formula (IV) is about 0.2 molar equivalents. Preferably, the amount of catalyst to compound of formula (IV) is about 0.3 molar equivalents.

Preferably, the amount of base to compound of formula (IV) is in the range of 1 to 10 molar equivalents. Preferably, the range is 1 to 7 molar equivalents. Preferably, the range is 1.1 to 6 molar equivalents. Preferably, the range is 1.2 to 5 molar equivalents. Preferably, the range is 1.3 to 4 molar equivalents. Preferably, the range is 1.4 to 3 molar equivalents. Preferably, the range is 1.5 to 2 molar equivalents. Preferably, the amount of base to compound of formula (IV) is about 1.5 molar equivalents. Preferably, the amount of base to compound of formula (IV) is about 2 molar equivalents.

Without wishing to be bound by theory, it is believed that step B is reversible in the presence of water. Thus, without wishing to be bound by theory, it is believed that the reaction of step B is optimized by minimizing the amount of water present in step B.

Step B may be conducted using formula (IV) or a pharmaceutically acceptable salt thereof.

Examples of Step B are shown in Scheme 3 and Table II below. Scheme 3 provides an example of a Step B reaction, and Table II provides reaction conditions used in the reaction shown in Scheme 3.

Scheme 3

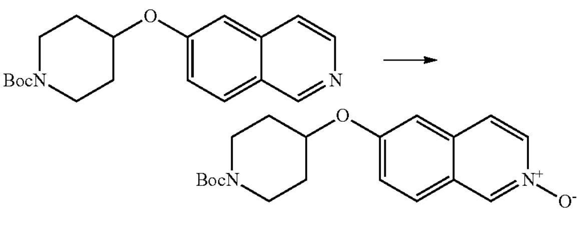

Although the product of Scheme 3, which is a compound of formula (V), is shown in a zwitterionic N-oxide form, i.e., wherein $R_4$ is —$O^-$, it may also be in a form wherein the nitrogen atom of the N-oxide is bound to —OH (i.e., wherein $R_4$ is —OH) or to methanesulfonate (-MsO) (i.e., wherein $R_4$ is -MsO). These forms are shown below:

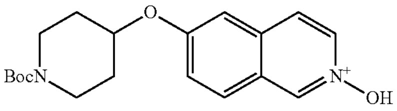

-continued

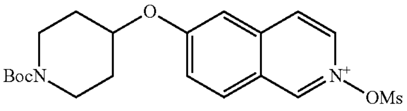

TABLE II

| # | Reactant, Compound of Formula (IV) | Reaction Conditions | Yield % | Purity (area %) |
|---|---|---|---|---|
| 1 | 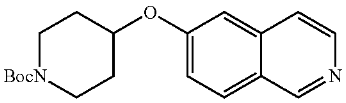 (1 eq.) | Reaction scale: 55 g DCM (15 volumes) mCPBA (1.8 eq.) mCPBA was added at 5-10° C., then the reaction mixture was stirred as the temperature warmed to room temperature for a total of 3 hours | 54.9% (57.8 g) | 98.39 |
| 2 | 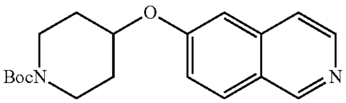 (1 eq.) | Reaction scale: 0.328 g DCM (5 volumes) After an initial charge of hydrogen peroxide ($H_2O_2$, 2 eq.) was added, a second charge of $H_2O_2$ (0.8 eq. $H_2O_2$) was added (for 3 eq. total $H_2O_2$) Methyltrioxorhenium (VII) ($MeReO_3$, MTO) (0.02 eq.) Reaction mixture was stirred overnight after the first charge of $H_2O_2$ was added, and then stirred again overnight after the second charge of H2O2 was added | N/A | 92 |
| 3 | 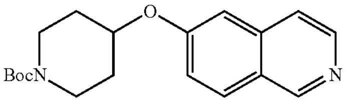 (1 eq.) | Reaction scale: 0.328 g MeCN (6 volumes) $H_2O_2$ (2 eq.) Phosphomolybdic acid (PMA, 0.02 eq.) Reaction mixture was stirred at 50° C. overnight | N/A | 91.4 |
| 4 | 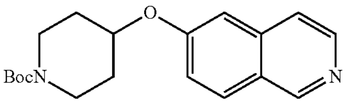 (1 eq.) | Reaction scale: 0.328 g Acetic acid (AcOH, 6 volumes) Sodium perborate tetrahydrate ($NaBO_3$•4 $H_2O$) (2.2 eq.) Reaction mixture was stirred at 50° C. overnight | N/A | 72.8 |
| 5 | 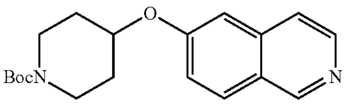 (1 eq.) | Reaction scale: 0.328 g MeCN (6 volumes) $Na_2CO_3$•1.5 $H_2O_2$ (2 eq.) MTO (0.02 eq.) AcOH (0.3 eq.) Reaction mixture was stirred at 50° C. overnight | N/A | 1.5 |

TABLE II-continued

| # | Reactant, Compound of Formula (IV) | Reaction Conditions | Yield % | Purity (area %) |
|---|---|---|---|---|
| 6 | 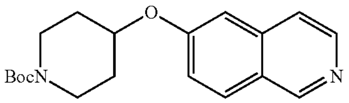 (1 eq.) | Reaction scale: 0.328 g MeCN (6 volumes), PMA (0.02 eq., then a second charge of 0.01 eq.), $H_2O_2$ (4 eq. initially, then a second charge of 1 eq., and a third charge of 1 eq., for 6 eq. total $H_2O_2$) Reaction mixture was stirred at 50° C. overnight, then a second charge of $H_2O_2$ (1.0 eq.) was added and the reaction mixture continued to be stirred at 50° C. overnight. A third charge of $H_2O_2$ (1.0 eq.) and a second charge of PMA (0.01 eq.) were added and the reaction mixture continued to be stirred at 50° C. overnight. | N/A | 88.1 |
| 7 | 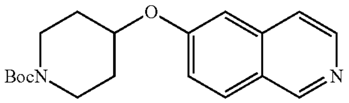 (1 eq.) | Reaction scale: 0.328 g AcOH (6 volumes) $H_2O_2$ (2.0 eq.) Reaction mixture was stirred at 72° C. overnight | N/A | 14.3 |
| 8 | 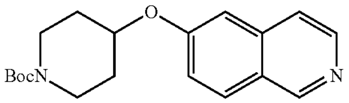 (1 eq.) | Reaction scale: 0.328 g MeCN (6 volumes) Urea hydrogen peroxide (urea $H_2O_2$, 2.2 eq.) PMA (0.02 eq.) Reaction mixture was stirred at 50° C. overnight | N/A | 96.9 |
| 9 | 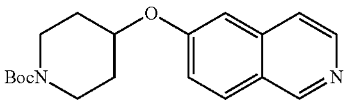 (1 eq.) | Reaction scale: 0.1 g Peracetic acid (AcOOH), 32% (1.8 eq.) DCM AcOOH was added at 5-10° C., then the reaction mixture was stirred as the temperature warmed to room temperature for a total of 3 hours | N/A | 84 |
| 10 | 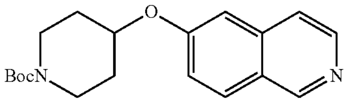 (1 eq.) | Reaction scale: 0.15 g MeCN (6 volumes) Urea $H_2O_2$ (2 eq.) PMA (0.02 eq.) Reaction mixture was stirred at 50° C. for 24 hours | N/A | 92 |
| 11 | 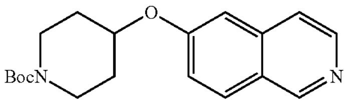 (1 eq.) | Reaction scale: 0.15 g MeCN (6 volumes) Urea $H_2O_2$ (2 eq.) PMA (0.02 eq.) Reaction mixture was stirred at 60° C. for 24 hours | N/A | 88 |
| 12 | 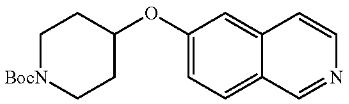 (1 eq.) | Reaction scale: 0.15 g MeCN (6 volumes) Urea $H_2O_2$ (1.5 eq.) PMA (0.02 eq.) Reaction mixture was stirred at 50° C. for 24 hours | N/A | 91 |
| 13 | 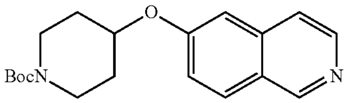 (1 eq.) | Reaction scale: 0.15 g MeCN (6 volumes) Urea $H_2O_2$ (1.5 eq.) PMA (0.02 eq.) Reaction mixture was stirred at 60° C. for 24 hours | N/A | 91 |

TABLE II-continued

| # | Reactant, Compound of Formula (IV) | Reaction Conditions | Yield % | Purity (area %) |
|---|---|---|---|---|
| 14 | 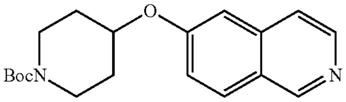<br>(1 eq.) | Reaction scale: 0.15 g<br>MeCN (10 volumes)<br>Urea $H_2O_2$ (1.5 eq.)<br>PMA (0.02 eq.)<br>Reaction mixture was stirred at 60° C. for 24 hours | 60 (uncorrected) | 98.3 |
| 15 | 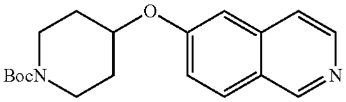<br>(1 eq.) | Reaction scale: 0.3 g<br>MeCN (15 volumes)<br>Urea $H_2O_2$ (1.5 eq.)<br>PMA (0.02 eq.)<br>Reaction mixture was stirred at 60° C. for 24 hours | 49 (uncorrected) | 98.7 |
| 16 | 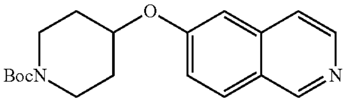<br>(1 eq.) | Reaction scale: 0.5 g<br>MeCN (10 volumes)<br>urea $H_2O_2$ (1.5 eq.)<br>PMA (0.01 eq.)<br>Reaction mixture was stirred at 60° C. for 29 hours | 63 | 97.6 |
| 17 | 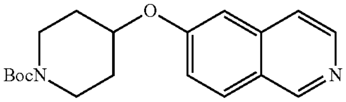<br>(1 eq.) | Reaction scale: 0.5 g<br>MeCN (10 volumes)<br>Urea $H_2O_2$ (two charges of 1.5 eq. each)<br>PMA (0.005 eq.)<br>Reaction mixture was stirred at 60° C. for 18 hours | 69 | 94 |
| 18 | 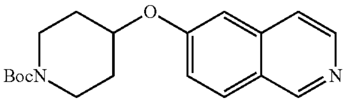<br>(1 eq.) | Reaction scale: 10 g<br>MeCN (10 volumes)<br>Urea $H_2O_2$ (two charges, 1.5 eq. each)<br>PMA (0.015 eq.)<br>Reaction mixture was stirred at 60° C. for 24 hours after first charge of urea $H_2O_2$ (1.5 eq. each) was added, then reaction mixture was stirred at 60° C. for an additional 24 hours after second charge of urea $H_2O_2$ (1.5 eq. each) was added | N/A | 86.4 |
| 19 | 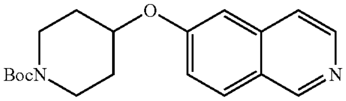<br>(1 eq.) | Reaction scale: 20 g<br>MeCN (6 volumes)<br>Urea $H_2O_2$ (2.2 eq.)<br>PMA (0.02 eq.)<br>Reaction mixture was stirred at 60° C. for 24 hours | 84 (uncorrected) (17.7 g) | 97.1 |
| 20 | 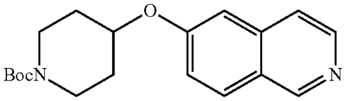<br>(1 eq.) | Reaction scale: 10 g<br>MeCN (6 volumes initially, then 4 additional volumes, for 10 volumes total)<br>Urea $H_2O_2$ (2.2 eq. initially, then additional charge of 1.0 eq., for 3.2 eq. total urea $H_2O_2$)<br>PMA (0.02 eq.)<br>Reaction mixture was stirred at 50° C. for 24 hours | 66 (7 g) | 95.6 |
| 21 | 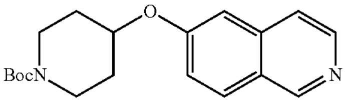<br>(1 eq.) | Reaction scale: 90 g<br>MeCN (6 volumes initially, then 4 additional volumes, for 10 volumes total)<br>Urea $H_2O_2$ (2.2 eq.)<br>PMA (0.02 eq.)<br>Reaction mixture was stirred at 50° C. for 24 hours | 56.3% (58.6 g) | 98.18 |

TABLE II-continued

| # | Reactant, Compound of Formula (IV) | Reaction Conditions | Yield % | Purity (area %) |
|---|---|---|---|---|
| 22 | 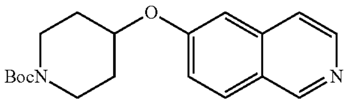 (1 eq.) | Reaction scale: 0.25 g<br>Ethanol (6 volumes)<br>Urea $H_2O_2$ (2.2 eq.)<br>PMA (0.02 eq.)<br>Reaction mixture was stirred at 50° C. for 16 hours | N/A | 91.8 |
| 23 | 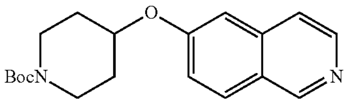 (1 eq.) | Reaction scale: 0.25 g<br>Ethanol (10 volumes)<br>Urea $H_2O_2$ (2.2 eq.)<br>PMA (0.02 eq.)<br>Reaction mixture was stirred at 50° C. for 16 hours | N/A | 85.7 |
| 24 | 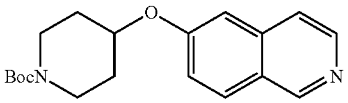 (1 eq.) | Reaction scale: 0.25 g<br>Propionitrile (10 volumes)<br>Urea $H_2O_2$ (2.2 eq.)<br>PMA (0.02 eq.)<br>Reaction mixture was stirred at 50° C. for 16 hours | N/A | 71.8 |
| 25 | 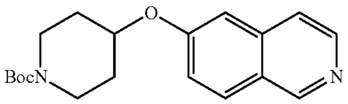 (1 eq.) | Reaction scale: 0.25 g<br>DCM (6 volumes)<br>35% $H_2O_2$ (2.2 eq.)<br>PMA (0.02 eq.)<br>Reaction mixture was stirred at 50° C. for 16 hours | N/A | 90.0 |
| 26 | 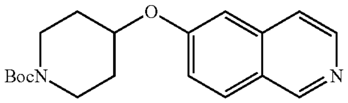 (1 eq.) | Reaction scale: 0.25 g<br>DCM (6 volumes)<br>35% $H_2O_2$ (1.5 eq.)<br>PMA (0.02 eq.)<br>Reaction mixture was stirred at 50° C. for 16 hours | N/A | 90.6 |
| 27 | 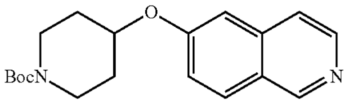 (1 eq.) | Reaction scale: 0.25 g<br>DCM (5 volumes)<br>Urea $H_2O_2$ (1.5 eq.)<br>PMA (0.02 eq.)<br>Reaction mixture was stirred at 50° C. for 16 hours | N/A | 31.4 |
| 28 | 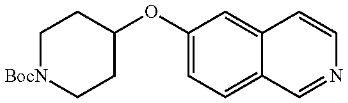 (1 eq.) | Reaction scale: 2.5 g<br>DCM (6 volumes)<br>Urea $H_2O_2$ (2.2 eq.)<br>PMA (0.02 eq.)<br>Reaction mixture was stirred at 50° C. for 16 hours | N/A | 83.1 |
| 29 | 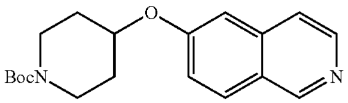 (1 eq.) | Reaction scale: 2.5 g<br>Ethanol (4 volumes)<br>Urea $H_2O_2$ (2.2 eq.)<br>PMA (0.02 eq.)<br>Reaction mixture was stirred at 50° C. for 16 hours | N/A | 91.8 |
| 30 | 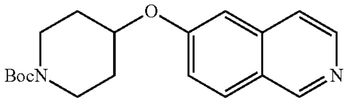 (1 eq.) | Reaction scale: 2.5 g<br>DCM (4 volumes) +<br>Ethanol (1 volumes)<br>Urea $H_2O_2$ (2.2 eq.)<br>PMA (0.02 eq.)<br>Reaction mixture was stirred at 50° C. for 16 hours | N/A | 58.2 |
| 31 | 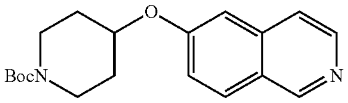 (1 eq.) | Reaction scale: 2.5 g<br>1-BuOH (10 volumes)<br>Urea $H_2O_2$ (2.2 eq.)<br>PMA (0.02 eq.)<br>Reaction mixture was stirred at 50° C. for 16 hours | N/A | 91.6 |

TABLE II-continued

| # | Reactant, Compound of Formula (IV) | Reaction Conditions | Yield % | Purity (area %) |
|---|---|---|---|---|
| 32 | 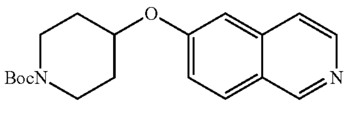 (1 eq.) | Reaction scale: 0.25 g<br>Ethanol (5 volumes)<br>Urea $H_2O_2$ (3 eq.)<br>PMA (0.02 eq.)<br>Reaction mixture was stirred at 50° C. for 16 hours | N/A | 91.1 |
| 33 | 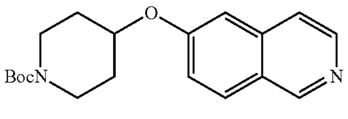 (1 eq.) | Reaction scale: 0.25 g<br>Ethanol (5 volumes)<br>Urea $H_2O_2$ (1.5 eq.)<br>PMA (0.02 eq.)<br>Reaction mixture was stirred at 50° C. for 16 hours | N/A | 90.7 |
| 34 | 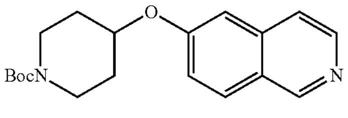 (1 eq.) | Reaction scale: 0.25 g<br>Ethanol (5 volumes)<br>Urea $H_2O_2$ (2 eq.)<br>PMA (0.03 eq.)<br>Reaction mixture was stirred at 50° C. for 16 hours | N/A | 92.0 |
| 35 | 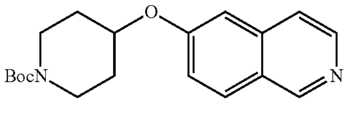 (1 eq.) | Reaction scale: 0.25 g<br>Ethanol (5 volumes)<br>35% $H_2O_2$ (1.5 eq.)<br>PMA (0.02 eq.)<br>Reaction mixture was stirred at 50° C. for 16 hours | N/A | 78.3 |
| 36 | 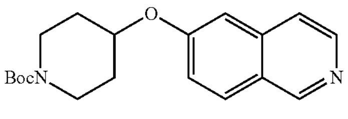 (1 eq.) | Reaction scale: 0.25 g<br>Ethanol (5 volumes)<br>35% $H_2O_2$ (3 eq.)<br>PMA (0.02 eq.)<br>Reaction mixture was stirred at 50° C. for 16 hours | N/A | 75.3 |
| 37 | 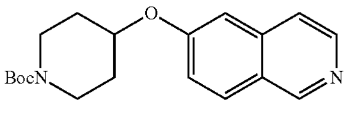 (1 eq.) | Reaction scale: 100 g<br>Ethanol (5 volumes)<br>Urea $H_2O_2$ (2 eq.)<br>PMA (0.02 eq.)<br>Reaction mixture was stirred at 50° C. for 16 hours | 82 (83.7 g) | 98.8 |
| 37 | 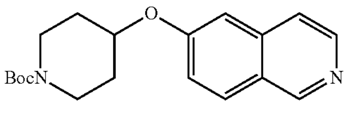 (1 eq.) | Reaction scale: 1420 g<br>Ethanol (5 volumes)<br>Urea $H_2O_2$ (2 eq.)<br>PMA (0.02 eq.)<br>Reaction mixture was stirred at 50° C. for 16 hours | 86 (1287 g) | 98.5 |

In one embodiment, the present invention relates to a process for using a compound of formula (V) to prepare a compound of formula (I) comprising a step C, reacting a compound of formula (V)

(V)

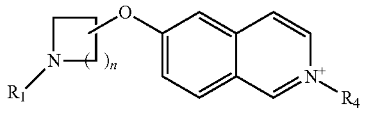

to produce a compound of formula (I)

(I)

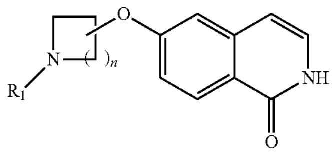

wherein $R_1$ is H, a $C_1$-$C_6$ alkyl group, or a protecting group as defined above, and n is 1, 2, 3, or 4.

Step C is shown below.

Step C

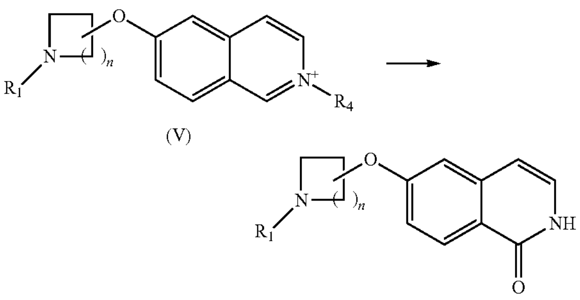

(V)

(I)

Preferably, $R_1$ is H or a protecting group as defined above.

Preferably, $R_1$ is a protecting group as defined above.

Preferably, $R_1$ is a protecting group selected from the group consisting of a trityl (triphenylmethyl, Tr) group, a (4-methoxyphenyl)diphenylmethylene (methoxytrityl, MMT) group, a tert-butyloxycarbonyl (BOC) group, and a p-toluenesulfonyl (tosyl, Ts) group.

Preferably, $R_1$ is a tert-butyloxycarbonyl (BOC) group.

Preferably, $R_1$ is a $C_1$-$C_6$ alkyl group.

Preferably, $R_1$ is methyl, ethyl, n-propyl, isopropyl, n-butyl, sec-butyl, or tert-butyl.

Preferably, n is 1, 2, or 3.

Preferably, n is 2 or 3.

Preferably, n is 3.

Preferably, step C comprises reacting a compound of formula (V) to form a compound of formula (I) in the presence of additional reagents selected from the group consisting of electrophilic reagents, solvents, bases, buffers, and mixtures thereof.

Suitable electrophilic reagents for use in step C may be selected from the group consisting of acyl halides, acid anhydrides, sulfonyl halide reagents, and mixtures thereof.

Preferably, the electrophilic reagents used in step C are acyl halides selected from the group consisting of acyl chloride, acyl bromide, acyl iodide, and mixtures thereof.

Preferably, the electrophilic reagents used in step C are acid anhydrides selected from the group consisting of acetic anhydride, formic anhydride, acetic formic anhydride, trifluoroacetic anhydride, trimethylacetic anhydride, hexanoic anhydride, benzoic anhydride, and mixtures thereof.

Preferably, the electrophilic reagents used in step C are sulfonyl halide reagents selected from the group consisting of benzensulfonyl chloride, benzensulfonyl bromide, benzensulfonyl iodide, methanesulfonyl chloride (mesyl chloride, MsCl), methanesulfonyl bromide, methanesulfonyl iodide, p-toluenesulfonyl chloride (tosyl chloride, TsCl), p-toluenesulfonyl bromide, p-toluenesulfonyl iodide, and mixtures thereof.

Suitable solvents for use in step C may be selected from the group consisting of water, amides, ethers, ketones, halogenated alkanes, nitriles, and mixtures thereof.

The solvent used in step C may be an amide selected from the group consisting of DMF, DMA, 2-pyrrolidone, and mixtures thereof.

The solvent used in step C may be an ether selected from the group consisting of diethyl ether, THF, 2-MeTHF, DME, MTBE, 1,4-dioxane, and mixtures thereof.

The solvent used in step C may be a ketone selected from the group consisting of acetone, methyl ethyl ketone, cyclohexanone, and mixtures thereof.

The solvent used in step C may be a halogenated alkane selected from the group consisting of DCM, chloroform, carbon tetrachloride, 1,2-dichloroethane, and mixtures thereof.

The solvent used in step C may be a nitrile selected from the group consisting of MeCN, propionitrile, benzonitrile, and mixtures thereof.

The solvent used in step C may be a mixture of water with one or more organic solvents selected from the group consisting of ethers, ketones, halogenated alkanes, and nitriles.

Suitable bases for use in step C may be selected from the group consisting of organic bases, inorganic bases, and mixtures thereof.

The base used in step C may be an organic base selected from the group consisting of amine bases, alkoxide salts, and mixtures thereof.

The base used in step C may be an amine base selected from the group consisting of ammonia, methyl amine, dimethyl amine, trimethyl amine, ethyl amine, diethyl amine, triethyl amine, propyl amine, dipropyl amine, tripropyl amine, isopropyl amine, diisopropyl amine, triisopropyl amine, N,N-diisopropylethylamine, and mixtures thereof.

The base used in step C may be an alkoxide salt selected from the group consisting of lithium methoxide, sodium methoxide, potassium methoxide, lithium ethoxide, sodium ethoxide, potassium ethoxide, lithium tert-butoxide, sodium tert-butoxide, potassium tert-butoxide, and mixtures thereof.

The base used in step C may be an inorganic base selected from the group consisting of hydroxide salts, carbonate salts, bicarbonate salts, phosphate salts, hydrogen phosphate salts, dihydrogen phosphate salts, and mixtures thereof.

The base used in step C may be a hydroxide salt selected from the group consisting of lithium hydroxide, sodium hydroxide, potassium hydroxide, and mixtures thereof.

The base used in step C may be a carbonate salt selected from the group consisting of lithium carbonate, sodium carbonate, potassium carbonate, cesium carbonate, and mixtures thereof.

The base used in step C may be a bicarbonate salt selected from the group consisting of lithium bicarbonate, sodium bicarbonate, potassium bicarbonate, and mixtures thereof.

The base used in step C may be a phosphate salt selected from the group consisting of lithium phosphate, sodium phosphate, potassium phosphate, and mixtures thereof.

The base used in step C may be a hydrogen phosphate salt selected from the group consisting of dilithium hydrogen phosphate, disodium hydrogen phosphate, dipotassium hydrogen phosphate, and mixtures thereof.

The base used in step C may be a dihydrogen phosphate salt selected from the group consisting of lithium dihydrogen phosphate, sodium dihydrogen phosphate, potassium dihydrogen phosphate, and mixtures thereof.

Suitable buffers for use in step C are buffers that maintain the pH of the reaction mixture of step C in a pH range between pH 4 and pH 10. Without wishing to be bound by theory, it is believed that at pH ranges lower than pH 4, impurities are formed in step C. Further, without wishing to be bound by theory, it is believed that at pH ranges higher than pH 10, the rate of hydrolysis of the electrophilic reagent is greater than the rate of step C. Examples of suitable buffers include acetate buffers, such as sodium acetate-acetic acid buffer (about pH 5.2). Additional examples of suitable buffers include the $H_3PO_4$— $Na_2HPO_4$ buffer (about pH 4), the $Na_2HPO_4$— $NaH_2PO_4$ buffer (between about pH 5.8 and about pH 10.0), the imidazole-HCl buffer (between about pH 6.2 and about pH 7.8), the $H_3PO_4$-triethylamine (TEA)

buffer (about pH 7), the citric acid-triethylamine (TEA) buffer (about pH 7), the citric acid-tris(hydroxymethyl) aminomethane (TRIS) buffer (about pH 8), and the 3-(N-morpholino)-propanesulfonic acid (MOPS)-triethylamine (TEA) buffer (about pH 7).

Preferably, step C is carried out in the presence of an electrophilic reagent and a solvent. Preferably, the electrophilic reagent is selected from the group consisting of methanesulfonyl chloride (mesyl chloride, MsCl), p-toluenesulfonyl chloride (tosyl chloride, TsCl), acyl chloride, acyl bromide, acetic anhydride, trifluoroacetic anhydride, trimethylacetic anhydride, and mixtures thereof; and the solvent is selected from the group consisting of water, DMF, diethyl ether, THF, 2-MeTHF, DME, MTBE, 1,4-dioxane, acetone, methyl ethyl ketone, cyclohexanone, DCM, chloroform, MeCN, and mixtures thereof. Preferably, the electrophilic reagent is selected from the group consisting of methanesulfonyl chloride (mesyl chloride, MsCl), p-toluenesulfonyl chloride (tosyl chloride, TsCl), acyl chloride, acyl bromide, acetic anhydride, and mixtures thereof; and the solvent is selected from the group consisting of water, DMF, THF, 2-MeTHF, acetone, methyl ethyl ketone, DCM, chloroform, MeCN, and mixtures thereof. Preferably, the electrophilic reagent is selected from the group consisting of methanesulfonyl chloride (mesyl chloride, MsCl), p-toluenesulfonyl chloride (tosyl chloride, TsCl), acyl chloride, acyl bromide, acetic anhydride, and mixtures thereof; and the solvent is selected from the group consisting of water, DMF, THF, 2-MeTHF, acetone, DCM, MeCN, and mixtures thereof. Preferably, the electrophilic reagent is selected from the group consisting of methanesulfonyl chloride (mesyl chloride, MsCl), p-toluenesulfonyl chloride (tosyl chloride, TsCl), acyl chloride, and mixtures thereof; and the solvent is selected from the group consisting of water, THF, 2-MeTHF, acetone, DCM, MeCN, and mixtures thereof. Preferably, the electrophilic reagent is selected from the group consisting of methanesulfonyl chloride (mesyl chloride, MsCl), p-toluenesulfonyl chloride (tosyl chloride, TsCl), acyl chloride, and mixtures thereof; and the solvent is a mixture of water and at least one organic solvent selected from the group consisting of THF, 2-MeTHF, acetone, DCM, and MeCN. Preferably, the electrophilic reagent is methanesulfonyl chloride (mesyl chloride, MsCl); and the solvent is a mixture of water and at least one organic solvent selected from the group consisting of THF, 2-MeTHF, acetone, DCM, and MeCN. Preferably, the electrophilic reagent is methanesulfonyl chloride (mesyl chloride, MsCl); and the solvent is a mixture of water and THF. Preferably, the electrophilic reagent is methanesulfonyl chloride (mesyl chloride, MsCl); and the solvent is a mixture of water and 2-MeTHF. Preferably, the electrophilic reagent is methanesulfonyl chloride (mesyl chloride, MsCl); and the solvent is a mixture of water and acetone. Preferably, the electrophilic reagent is methanesulfonyl chloride (mesyl chloride, MsCl); and the solvent is a mixture of water and DCM. Preferably, the electrophilic reagent is methanesulfonyl chloride (mesyl chloride, MsCl); and the solvent is a mixture of water and MeCN.

Preferably, step C is carried out in the presence of an electrophilic reagent, a solvent, and a base. Preferably, the electrophilic reagent is selected from the group consisting of methanesulfonyl chloride (mesyl chloride, MsCl), p-toluenesulfonyl chloride (tosyl chloride, TsCl), acyl chloride, acyl bromide, acetic anhydride, trifluoroacetic anhydride, trimethylacetic anhydride, and mixtures thereof; the solvent is selected from the group consisting of water, DMF, diethyl ether, THF, 2-MeTHF, DME, MTBE, 1,4-dioxane, acetone, methyl ethyl ketone, cyclohexanone, DCM, chloroform, MeCN, and mixtures thereof; and the base is selected from the group consisting of ammonia, methyl amine, dimethyl amine, trimethyl amine, ethyl amine, diethyl amine, triethyl amine, propyl amine, dipropyl amine, tripropyl amine, isopropyl amine, diisopropyl amine, triisopropyl amine, N,N-diisopropylethylamine, lithium carbonate, sodium carbonate, potassium carbonate, cesium carbonate, lithium bicarbonate, sodium bicarbonate, potassium bicarbonate, lithium phosphate, sodium phosphate, potassium phosphate, dilithium hydrogen phosphate, disodium hydrogen phosphate, dipotassium hydrogen phosphate, lithium dihydrogen phosphate, sodium dihydrogen phosphate, potassium dihydrogen phosphate, and mixtures thereof. Preferably, the electrophilic reagent is selected from the group consisting of methanesulfonyl chloride (mesyl chloride, MsCl), p-toluenesulfonyl chloride (tosyl chloride, TsCl), acyl chloride, acyl bromide, acetic anhydride, and mixtures thereof; the solvent is selected from the group consisting of water, DMF, THF, 2-MeTHF, acetone, methyl ethyl ketone, DCM, chloroform, MeCN, and mixtures thereof; and the base is selected from the group consisting of trimethyl amine, triethyl amine, tripropyl amine, triisopropyl amine, N,N-diisopropylethylamine, sodium carbonate, potassium carbonate, cesium carbonate, sodium bicarbonate, potassium bicarbonate, sodium phosphate, potassium phosphate, disodium hydrogen phosphate, dipotassium hydrogen phosphate, sodium dihydrogen phosphate, potassium dihydrogen phosphate, and mixtures thereof. Preferably, the electrophilic reagent is selected from the group consisting of methanesulfonyl chloride (mesyl chloride, MsCl), p-toluenesulfonyl chloride (tosyl chloride, TsCl), acyl chloride, acyl bromide, acetic anhydride, and mixtures thereof; the solvent is selected from the group consisting of water, DMF, THF, 2-MeTHF, acetone, DCM, MeCN, and mixtures thereof; and the base is selected from the group consisting of triethyl amine, triisopropyl amine, N,N-diisopropylethylamine, sodium carbonate, potassium carbonate, sodium bicarbonate, potassium bicarbonate, sodium phosphate, potassium phosphate, disodium hydrogen phosphate, dipotassium hydrogen phosphate, sodium dihydrogen phosphate, potassium dihydrogen phosphate, and mixtures thereof. Preferably, the electrophilic reagent is selected from the group consisting of methanesulfonyl chloride (mesyl chloride, MsCl), p-toluenesulfonyl chloride (tosyl chloride, TsCl), acyl chloride, and mixtures thereof; the solvent is selected from the group consisting of water, THF, 2-MeTHF, acetone, DCM, MeCN, and mixtures thereof; and the base is selected from the group consisting of triethyl amine, triisopropyl amine, N,N-diisopropylethylamine, sodium carbonate, potassium carbonate, sodium bicarbonate, potassium bicarbonate, sodium phosphate, potassium phosphate, disodium hydrogen phosphate, dipotassium hydrogen phosphate, sodium dihydrogen phosphate, potassium dihydrogen phosphate, and mixtures thereof. Preferably, the electrophilic reagent is selected from the group consisting of methanesulfonyl chloride (mesyl chloride, MsCl), p-toluenesulfonyl chloride (tosyl chloride, TsCl), acyl chloride, and mixtures thereof; the solvent is a mixture of water and at least one organic solvent selected from the group consisting of THF, 2-MeTHF, acetone, DCM, and MeCN; and the base is selected from the group consisting of triethyl amine, triisopropyl amine, N,N-diisopropylethylamine, sodium carbonate, potassium carbonate, sodium bicarbonate, potassium bicarbonate, sodium phosphate, potassium phosphate, disodium hydrogen phosphate, dipotassium hydrogen phosphate, sodium dihydrogen phosphate, potassium dihydrogen phosphate, and mixtures thereof. Preferably, the electrophilic reagent is methanesulfonyl chloride (mesyl chloride, MsCl); the solvent is a mixture of water and at least one organic solvent selected from the group consisting of THF, 2-MeTHF, acetone, DCM, and MeCN; and the base is selected from the group consisting of triethyl amine, triisopropyl amine, N,N-diisopropylethylamine, sodium carbonate, potassium carbonate, sodium bicarbonate, potassium bicarbonate, sodium phosphate, potassium phosphate, disodium hydrogen phosphate, dipotassium hydrogen phosphate, sodium dihydrogen phosphate, potassium dihydrogen phosphate, and mixtures thereof. Preferably, the electrophilic reagent is methanesulfonyl chloride (mesyl chloride, MsCl); the solvent is a mixture of water and THF; and the base is selected from the group consisting of triethyl amine, N,N-diisopropylethylamine, sodium carbonate, potassium carbonate, sodium bicarbonate, potassium bicarbonate, potassium phosphate, dipotassium hydrogen phosphate, potassium dihydrogen phosphate, and mixtures thereof. Preferably, the electrophilic reagent is methanesulfonyl chloride (mesyl chloride, MsCl); the solvent is a mixture of water and 2-MeTHF; and the base is selected from the group consisting of triethyl amine, N,N-diisopropylethylamine, sodium carbonate, potassium carbonate, sodium bicarbonate, potassium bicarbonate, potassium phosphate, dipotassium hydrogen phosphate, potassium dihydrogen phosphate, and mixtures thereof. Preferably, the electrophilic reagent is methanesulfonyl chloride (mesyl chloride, MsCl); the solvent is a mixture of water and acetone; and the base is selected from the group consisting of triethyl amine, N,N-diisopropylethylamine, sodium carbonate, potassium carbonate, sodium bicarbonate, potassium bicarbonate, potassium phosphate, dipotassium hydrogen phosphate, potassium dihydrogen phosphate, and mixtures thereof. Preferably, the electrophilic reagent is methanesulfonyl chloride (mesyl chloride, MsCl); the solvent is a mixture of water and DCM; and the base is selected from the group consisting of triethyl amine, N,N-diisopropylethylamine, sodium carbonate, potassium carbonate, sodium bicarbonate, potassium bicarbonate, potassium phosphate, dipotassium hydrogen phosphate, potassium dihydrogen phosphate, and mixtures thereof. Preferably, the electrophilic reagent is methanesulfonyl chloride (mesyl chloride, MsCl); the solvent is a mixture of water and MeCN; and the base is selected from the group consisting of triethyl amine, N,N-diisopropylethylamine, sodium carbonate, potassium carbonate, sodium bicarbonate, potassium bicarbonate, potassium phosphate, dipotassium hydrogen phosphate, potassium dihydrogen phosphate, and mixtures thereof.

Preferably, step C is carried out in the presence of an electrophilic reagent, a solvent, and a buffer. Preferably, the electrophilic reagent is selected from the group consisting of methanesulfonyl chloride (mesyl chloride, MsCl), p-toluenesulfonyl chloride (tosyl chloride, TsCl), acyl chloride, acyl bromide, acetic anhydride, trifluoroacetic anhydride, trimethylacetic anhydride, and mixtures thereof; the solvent is selected from the group consisting of water, DMF, diethyl ether, THF, 2-MeTHF, DME, MTBE, 1,4-dioxane, acetone, methyl ethyl ketone, cyclohexanone, DCM, chloroform, MeCN, and mixtures thereof; and the buffer is a buffer that maintains the pH of the reaction mixture of step C in a pH range between pH 4 and pH 10.

Preferably, the electrophilic reagent is selected from the group consisting of methanesulfonyl chloride (mesyl chloride, MsCl), p-toluenesulfonyl chloride (tosyl chloride, TsCl), acyl chloride, acyl bromide, acetic anhydride, trifluoroacetic anhydride, trimethylacetic anhydride, and mixtures thereof; the solvent is selected from the group consisting of water, DMF, diethyl ether, THF, 2-MeTHF, DME, MTBE, 1,4-dioxane, acetone, methyl ethyl ketone, cyclohexanone, DCM, chloroform, MeCN, and mixtures thereof; and the buffer is selected from the group consisting of sodium acetate-acetic acid buffer, $H_3PO_4$— $Na_2HPO_4$ buffer, $Na_2HPO_4$—$NaH_2PO_4$ buffer, imidazole-HCl buffer, $H_3PO_4$-triethylamine (TEA) buffer, citric acid-triethylamine (TEA) buffer, citric acid-tris(hydroxymethyl)aminomethane (TRIS) buffer, and 3-(N-morpholino)-propanesulfonic acid (MOPS)-triethylamine (TEA) buffer. Preferably, the electrophilic reagent is selected from the group consisting of methanesulfonyl chloride (mesyl chloride, MsCl), p-toluenesulfonyl chloride (tosyl chloride, TsCl), acyl chloride, acyl bromide, acetic anhydride, and mixtures thereof; the solvent is selected from the group consisting of water, DMF, THF, 2-MeTHF, acetone, methyl ethyl ketone, DCM, chloroform, MeCN, and mixtures thereof; and the buffer is selected from the group consisting of sodium acetate-acetic acid buffer, $H_3PO_4$— $Na_2HPO_4$ buffer, $Na_2HPO_4$—$NaH_2PO_4$ buffer, imidazole-HCl buffer, $H_3PO_4$-triethylamine (TEA) buffer, citric acid-triethylamine (TEA) buffer, citric acid-tris(hydroxymethyl)aminomethane (TRIS) buffer, and 3-(N-morpholino)-propanesulfonic acid (MOPS)-triethylamine (TEA) buffer. Preferably, the electrophilic reagent is selected from the group consisting of methanesulfonyl chloride (mesyl chloride, MsCl), p-toluenesulfonyl chloride (tosyl chloride, TsCl), acyl chloride, acyl bromide, acetic anhydride, and mixtures thereof; the solvent is selected from the group consisting of water, DMF, THF, 2-MeTHF, acetone, DCM, MeCN, and mixtures thereof; and the buffer is selected from the group consisting of sodium acetate-acetic acid buffer, $H_3PO_4$— $Na_2HPO_4$ buffer, $Na_2HPO_4$— $NaH_2PO_4$ buffer, imidazole-HCl buffer, $H_3PO_4$-triethylamine (TEA) buffer, citric acid-triethylamine (TEA) buffer, citric acid-tris(hydroxymethyl)aminomethane (TRIS) buffer, and 3-(N-morpholino)-propanesulfonic acid (MOPS)-triethylamine (TEA) buffer. Preferably, the electrophilic reagent is selected from the group consisting of methanesulfonyl chloride (mesyl chloride, MsCl), p-toluenesulfonyl chloride (tosyl chloride, TsCl), acyl chloride, and mixtures thereof; the solvent is selected from the group consisting of water, THF, 2-MeTHF, acetone, DCM, MeCN, and mixtures thereof; and the buffer is selected from the group consisting of sodium acetate-acetic acid buffer, $H_3PO_4$—$Na_2HPO_4$ buffer, $Na_2HPO_4$— $NaH_2PO_4$ buffer, imidazole-HCl buffer, $H_3PO_4$-triethylamine (TEA) buffer, citric acid-triethylamine (TEA) buffer, citric acid-tris(hydroxymethyl)aminomethane (TRIS) buffer, and 3-(N-morpholino)-propanesulfonic acid (MOPS)-triethylamine (TEA) buffer. Preferably, the electrophilic reagent is selected from the group consisting of methanesulfonyl chloride (mesyl chloride, MsCl), p-toluenesulfonyl chloride (tosyl chloride, TsCl), acyl chloride, and mixtures thereof; the solvent is a mixture of water and at least one organic solvent selected from the group consisting of THF, 2-MeTHF, acetone, DCM, and MeCN; and the buffer is selected from the group consisting of sodium acetate-acetic acid buffer, $H_3PO_4$— $Na_2HPO_4$ buffer, $Na_2HPO_4$— $NaH_2PO_4$ buffer, imidazole-HCl buffer, $H_3PO_4$-triethylamine (TEA) buffer, citric acid-triethylamine (TEA) buffer, citric acid-tris(hydroxymethyl) aminomethane (TRIS) buffer, and 3-(N-morpholino)-propanesulfonic acid (MOPS)-triethylamine (TEA) buffer. Preferably, the electrophilic reagent is methanesulfonyl chloride (mesyl chloride, MsCl); the solvent is a mixture of water and at least one organic solvent selected from the group consisting of THF, 2-MeTHF, acetone, DCM, and MeCN; and the buffer is selected from the group consisting of sodium acetate-acetic acid buffer, $H_3PO_4$—$Na_2HPO_4$ buffer, $Na_2HPO_4$— $NaH_2PO_4$ buffer, imidazole-HCl buffer, $H_3PO_4$-triethylamine (TEA) buffer, citric acid-triethylamine (TEA) buffer, citric acid-tris(hydroxymethyl)aminomethane (TRIS) buffer, and 3-(N-morpholino)-propanesulfonic acid (MOPS)-triethylamine (TEA) buffer. Preferably, the electrophilic reagent is methanesulfonyl chloride (mesyl chloride, MsCl); the solvent is a mixture of water and THF; and the buffer is selected from the group consisting of sodium acetate-acetic acid buffer, $H_3PO_4$— $Na_2HPO_4$ buffer, $Na_2HPO_4$— $NaH_2PO_4$ buffer, imidazole-HCl buffer, $H_3PO_4$-triethylamine (TEA) buffer, citric acid-triethylamine (TEA) buffer, citric acid-tris(hydroxymethyl)aminomethane (TRIS) buffer, and 3-(N-morpholino)-propanesulfonic acid (MOPS)-triethylamine (TEA) buffer. Preferably, the electrophilic reagent is methanesulfonyl chloride (mesyl chloride, MsCl); the solvent is a mixture of water and 2-MeTHF; and the buffer is selected from the group consisting of sodium acetate-acetic acid buffer, $H_3PO_4$— $Na_2HPO_4$ buffer, $Na_2HPO_4$—$NaH_2PO_4$ buffer, imidazole-HCl buffer, $H_3PO_4$-triethylamine (TEA) buffer, citric acid-triethylamine (TEA) buffer, citric acid-tris(hydroxymethyl)aminomethane (TRIS) buffer, and 3-(N-morpholino)-propanesulfonic acid (MOPS)-triethylamine (TEA) buffer. Preferably, the electrophilic reagent is methanesulfonyl chloride (mesyl chloride, MsCl); the solvent is a mixture of water and acetone; and the buffer is selected from the group consisting of sodium acetate-acetic acid buffer, $H_3PO_4$— $Na_2HPO_4$ buffer, $Na_2HPO_4$— $NaH_2PO_4$ buffer, imidazole-HCl buffer, $H_3PO_4$-triethylamine (TEA) buffer, citric acid-triethylamine (TEA) buffer, citric acid-tris(hydroxymethyl) aminomethane (TRIS) buffer, and 3-(N-morpholino)-propanesulfonic acid (MOPS)-triethylamine (TEA) buffer. Preferably, the electrophilic reagent is methanesulfonyl chloride (mesyl chloride, MsCl); the solvent is a mixture of water and DCM; and the buffer is selected from the group consisting of sodium acetate-acetic acid buffer, $H_3PO_4$— $Na_2HPO_4$ buffer, $Na_2HPO_4$— $NaH_2PO_4$ buffer, imidazole-HCl buffer, $H_3PO_4$-triethylamine (TEA) buffer, citric acid-triethylamine (TEA) buffer, citric acid-tris(hydroxymethyl)aminomethane (TRIS) buffer, and 3-(N-morpholino)-propanesulfonic acid (MOPS)-triethylamine (TEA) buffer. Preferably, the electrophilic reagent is methanesulfonyl chloride (mesyl chloride, MsCl); the solvent is a mixture of water and MeCN; and the buffer is selected from the group consisting of sodium acetate-acetic acid buffer, $H_3PO_4$— $Na_2HPO_4$ buffer, $Na_2HPO_4$— $NaH_2PO_4$ buffer, imidazole-HCl buffer, $H_3PO_4$-triethylamine (TEA) buffer, citric acid-triethylamine (TEA) buffer, citric acid-tris(hydroxymethyl)aminomethane (TRIS) buffer, and 3-(N-morpholino)-propanesulfonic acid (MOPS)-triethylamine (TEA) buffer.

Preferably, the amount of electrophilic reagent to compound of formula (V) is in the range of 0.05 to 10 molar equivalents. Preferably, the range is 0.1 to 7 molar equivalents. Preferably, the range is 0.2 to 6 molar equivalents. Preferably, the range is 0.25 to 5 molar equivalents. Preferably, the range is 0.3 to 4 molar equivalents. Preferably, the range is 0.4 to 3 molar equivalents. Preferably, the range is 0.5 to 2.5 molar equivalents. Preferably, the range is 0.6 to 2.25 molar equivalents. Preferably, the range is 0.7 to 2 molar equivalents. Preferably, the range is 0.75 to 1.75 molar equivalents. Preferably, the amount of electrophilic reagent to compound of formula (V) is about 1.5 molar equivalents. Preferably, the amount of electrophilic reagent to compound of formula (V) is about 1.6 molar equivalents. Preferably, the amount of electrophilic reagent to compound of formula (V) is about 1.7 molar equivalents. Preferably, the amount of electrophilic reagent to compound of formula (V) is about 1.8 molar equivalents. Preferably, the amount of electrophilic reagent to compound of formula (V) is about 1.9 molar equivalents. Preferably, the amount of electrophilic reagent to compound of formula (V) is about 2 molar equivalents. Preferably, the amount of electrophilic reagent to compound of formula (V) is about 2.1 molar equivalents. Preferably, the amount of electrophilic reagent to compound of formula (V) is about 2.2 molar equivalents. Preferably, the amount of electrophilic reagent to compound of formula (V) is about 2.3 molar equivalents. Preferably, the amount of electrophilic reagent to compound of formula (V) is about 2.4 molar equivalents. Preferably, the amount of electrophilic reagent to compound of formula (V) is about 2.5 molar equivalents. Preferably, the amount of electrophilic reagent to compound of formula (V) is about 3 molar equivalents. Preferably, the amount of electrophilic reagent to compound of formula (V) is about 3.5 molar equivalents. Preferably, the amount of electrophilic reagent to compound of formula (V) is about 4 molar equivalents. Preferably, the amount of electrophilic reagent to compound of formula (V) is about 4.5 molar equivalents. Preferably, the amount of electrophilic reagent to compound of formula (V) is about 5 molar equivalents. Preferably, the amount of electrophilic reagent to compound of formula (V) is about 0.25 molar equivalents. Preferably, the amount of electrophilic reagent to compound of formula (V) is about 0.5 molar equivalents. Preferably, the amount of electrophilic reagent to compound of formula (V) is about 0.75 molar equivalents. Preferably, the amount of electrophilic reagent to compound of formula (V) is about 1 molar equivalent.

Preferably, the amount of base to compound of formula (V) is in the range of 0.1 to 10 molar equivalents. Preferably, the range is 0.5 to 9 molar equivalents. Preferably, the range is 0.75 to 8 molar equivalents. Preferably, the range is 1 to 7 molar equivalents. Preferably, the range is 1.5 to 6 molar equivalents. Preferably, the amount of base to compound of formula (V) is about 0.25 molar equivalents. Preferably, the amount of base to compound of formula (V) is about 0.5 molar equivalents. Preferably, the amount of base to compound of formula (V) is about 0.75 molar equivalents. Preferably, the amount of base to compound of formula (V) is about 1 molar equivalent. Preferably, the amount of base to compound of formula (V) is about 1.5 molar equivalent. Preferably, the amount of base to compound of formula (V) is about 2 molar equivalents. Preferably, the amount of base to compound of formula (V) is about 2.5 molar equivalents. Preferably, the amount of base to compound of formula (V) is about 3 molar equivalents. Preferably, the amount of base to compound of formula (V) is about 4 molar equivalents. Preferably, the amount of base to compound of formula (V) is about 5 molar equivalents. Preferably, the amount of base to compound of formula (V) is about 6 molar equivalents. Preferably, the amount of base to compound of formula (V) is about 7 molar equivalents. Preferably, the amount of base to compound of formula (V) is about 7.5 molar equivalents. Preferably, the amount of base to compound of formula (V) is about 8 molar equivalents. Preferably, the amount of base to compound of formula (V) is about 9 molar equivalents.

Preferably, the amount of buffer used in step C is sufficient to maintain the pH in a pH range between pH 4 and pH 10 for the duration of step C.

Preferably, the amount of buffer to compound of formula (V) is in the range of 1 to 10 molar equivalents. Preferably, the range is 1.5 to 9 molar equivalents. Preferably, the range is 2 to 8 molar equivalents. Preferably, the range is 2.5 to 7 molar equivalents. Preferably, the amount of buffer to compound of formula (V) is about 2 molar equivalents. Preferably, the amount of buffer to compound of formula (V) is about 3 molar equivalents. Preferably, the amount of buffer to compound of formula (V) is about 4 molar equivalents. Preferably, the amount of buffer to compound of formula (V) is about 5 molar equivalents. Preferably, the amount of buffer to compound of formula (V) is about 6 molar equivalents. Preferably, the amount of buffer to compound of formula (V) is about 7 molar equivalents. Preferably, the amount of buffer to compound of formula (V) is about 7.5 molar equivalents. Preferably, the amount of buffer to compound of formula (V) is about 8 molar equivalents.

Preferably, the ratio of volumes of water to volumes of organic solvent in step C is in the range of 1:10 to 10:1. Preferably, the ratio of volumes of water to volumes of organic solvent in step C is in the range of 1:9 to 9:1. Preferably, the ratio of volumes of water to volumes of organic solvent in step C is in the range of 1:8 to 8:1. Preferably, the ratio of volumes of water to volumes of organic solvent in step C is in the range of 1:7 to 7:1. Preferably, the ratio of volumes of water to volumes of organic solvent in step C is in the range of 1:6 to 6:1. Preferably, the ratio of volumes of water to volumes of organic solvent in step C is in the range of 1:5 to 5:1. Preferably, the ratio of volumes of water to volumes of organic solvent in step C is in the range of 1:4 to 4:1. Preferably, the ratio of volumes of water to volumes of organic solvent in step C is in the range of 1:3 to 3:1. Preferably, the ratio of volumes of water to volumes of organic solvent in step C is in the range of 1:2 to 2:1. Preferably, the ratio of volumes of water to volumes of organic solvent in step C is 1:1. Preferably, the ratio of volumes of water to volumes of organic solvent in step C is 2:1. Preferably, the ratio of volumes of water to volumes of organic solvent in step C is 1:2. Preferably, the ratio of volumes of water to volumes of organic solvent in step C is 2:3. Preferably, the ratio of volumes of water to volumes of organic solvent in step C is 3:2. Preferably, the ratio of volumes of water to volumes of organic solvent in step C is 4:3. Preferably, the ratio of volumes of water to volumes of organic solvent in step C is 3:4. Preferably, the ratio of volumes of water to volumes of organic solvent in step C is 5:3. Preferably, the ratio of volumes of water to volumes of organic solvent in step C is 3:5.

Step C may be conducted using formula (V) or a pharmaceutically acceptable salt thereof.

Preferably, step C is carried out from about −10° C. to about 100° C. Preferably, step C is carried out from about −5° C. to about 80° C. Preferably, step C is carried out from about 0° C. to about 65° C. Preferably, step C is carried out from about 5° C. to about 50° C. Preferably, step C is carried out from about 10° C. to about 35° C. Preferably, step C is carried out from about 15° C. to about 30° C. Preferably, step C is carried out from about 20° C. to about 25° C. Preferably, step C is carried out at about 20° C. Preferably, step C is carried out at about 21° C. Preferably, step C is carried out at about 22° C. Preferably, step C is carried out at about 23° C. Preferably, step C is carried out at about 24° C. Preferably, step C is carried out at about 25° C. Preferably, step C is carried out from about −10° C. to about 20° C. Preferably, step C is carried out from about −5° C. to about 15° C. Preferably, step C is carried out from about −5° C. to about 5° C. Preferably, step C is carried out at about 0° C. Preferably, step C is carried out from about 0° C. to about 15° C. Preferably, step C is carried out from about 5° C. to about 10° C.

Examples of Step C are shown in Scheme 4 and Table III below. Scheme 4 provides an example of a Step C reaction, and Table III provides reaction conditions used in the reaction shown in Scheme 4.

Scheme 4

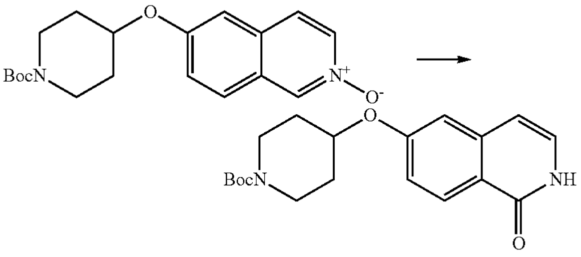

Although the reactant of Scheme 4, which is a compound of formula (V), is shown in a zwitterionic N-oxide form, i.e., wherein $R_4$ is —O—, it may also be in a form wherein the nitrogen atom of the N-oxide is bound to —OH (i.e., wherein $R_4$ is —OH) or to sulfonates such as methanesulfonate (-MsO) (i.e., wherein $R_4$ is -MsO). These forms are shown below:

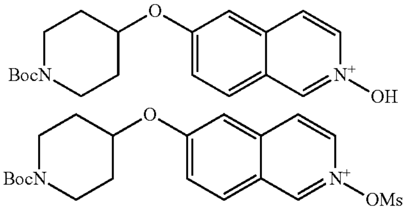

Further, although the product of Scheme 4, which is a compound of formula (I), is shown in a lactam form, it may also be in a lactim form or in an equilibrium of both forms, as shown below:

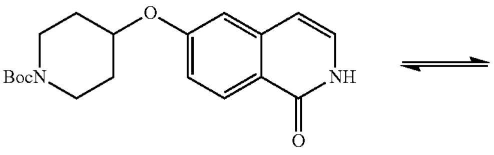

Lactam Form

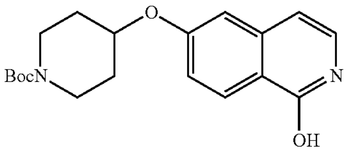

Lactim Form

TABLE III

| # | Reactant, Compound of Formula (V) | Reaction Conditions | Yield % | Purity (area %) |
|---|---|---|---|---|
| 1 | 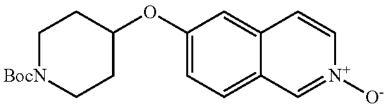 (1 eq.) | Reaction scale: 28 g<br>THF/water ($H_2O$)<br>(10 volumes/10 volumes)<br>Methanesulfonyl chloride<br>(MsCl, 1.8 eq.)<br>Reaction mixture was stirred at room temperature for 3 hours | 60.9 (17.17 g) | 84.1 |
| 2 | 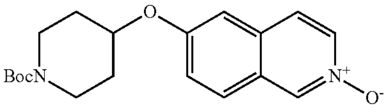 (1 eq.) | Reaction scale: 0.1 g<br>THF/$H_2O$ (3 volumes/<br>3 volumes)<br>MsCl (2.0 eq.)<br>Reaction mixture was stirred at room temperature for 18 hours | N/A | 72.2 |
| 3 | 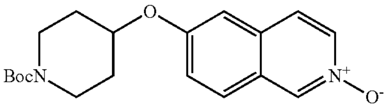 (1 eq.) | Reaction scale: 0.1 g<br>THF/$H_2O$ (4 volumes/<br>4 volumes)<br>MsCl (2.0 eq.)<br>Reaction mixture was stirred at room temperature for 18 hours | N/A | 72.8 |
| 4 | 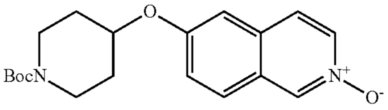 (1 eq.) | Reaction scale: 0.1 g<br>THF/$H_2O$ (6 volumes/<br>6 volumes)<br>MsCl (2.0 eq.)<br>Reaction mixture was stirred at room temperature for 18 hours | N/A | 73.7 |
| 5 | 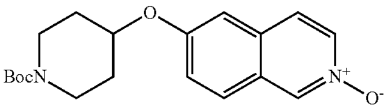 (1 eq.) | Reaction scale: 0.1 g<br>THF/$H_2O$ (10 volumes/<br>10 volumes)<br>MsCl (2.0 eq.)<br>Reaction mixture was stirred at room temperature for 18 hours | N/A | 47.8 |
| 6 | 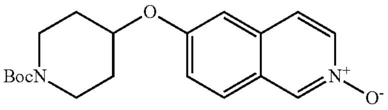 (1 eq.) | Reaction scale: 0.1 g<br>THF/$H_2O$ (4 volumes/<br>4 volumes)<br>$NaHCO_3$ (3.0 eq.)<br>MsCl (2.0 eq.)<br>Reaction mixture was stirred at room temperature for 2 hours | N/A | 81.5 |
| 7 | 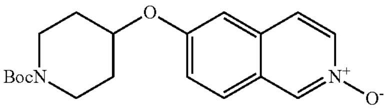 (1 eq.) | Reaction scale: 1 g<br>THF/$H_2O$ (4 volumes/<br>4 volumes)<br>$NaHCO_3$ (3.0 eq.)<br>MsCl (2.0 eq.)<br>Reaction mixture was stirred at 0° C. for 2 hours | N/A | 99.5 |
| 8 | 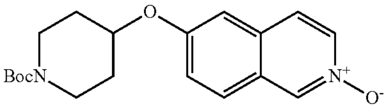 (1 eq.) | Reaction scale: 1 g<br>THF/$H_2O$ (4 volumes/<br>4 volumes)<br>$NaHCO_3$ (3 eq.)<br>MsCl (2.0 eq.)<br>Reaction mixture was stirred at 0° C. for 2 hours | N/A | 90.9 |
| 9 | 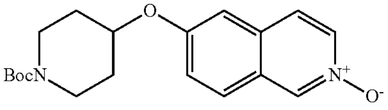 (1 eq.) | Reaction scale: 0.25 g<br>THF/$H_2O$ (3 volumes/<br>3 volumes)<br>$NaHCO_3$ (3.0 eq.)<br>MsCl (2.0 eq.)<br>Reaction mixture was stirred at 0° C. for 2 hours | N/A | 61.0 |

TABLE III-continued

| # | Reactant, Compound of Formula (V) | Reaction Conditions | Yield % | Purity (area %) |
|---|---|---|---|---|
| 10 | 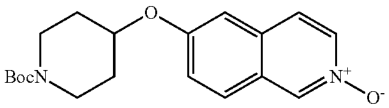 (1 eq.) | Reaction scale: 0.25 g THF/$H_2O$ (3 volumes/ 3 volumes) $NaHCO_3$ (3.0 eq.) MsCl (2.0 eq.) Reaction mixture was stirred at 0° C. for 2 hours and was purged with nitrogen ($N_2$) gas | N/A | 46.7 |
| 11 | 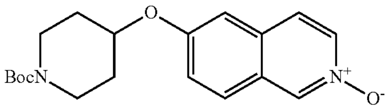 (1 eq.) | Reaction scale: 0.25 g DCM/$H_2O$ (3 volumes/ 3 volumes) $NaHCO_3$ (3.0 eq.) MsCl (2.0 eq.) Reaction mixture was stirred at 0° C. for 2 hours and was purged with nitrogen ($N_2$) gas | N/A | 40.7 |
| 12 | 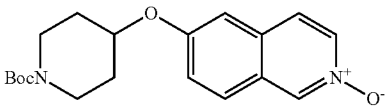 (1 eq.) | Reaction scale: 0.25 g THF/$H_2O$ (4 volumes/ 8 volumes) $NaHCO_3$ (3.0 eq.) MsCl (2.0 eq.) Reaction mixture was stirred at 0° C. for 2 hours and was purged with nitrogen ($N_2$) gas | N/A | 80.3 |
| 13 | 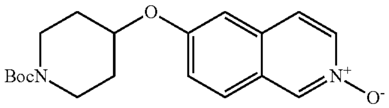 (1 eq.) | Reaction scale: 0.25 g THF/$H_2O$ (4 volumes/ 8 volumes) $NaHCO_3$ (3.0 eq.) MsCl (2.0 eq.) Reaction mixture was stirred at 0° C. for 2 hours and was purged with nitrogen ($N_2$) gas | N/A | N/A |
| 14 | 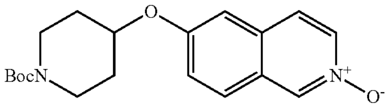 (1 eq.) | Reaction scale: 0.5 g 2-MeTHF/H2O (3 volumes/3 volumes) $K_2CO_3$ (3.0 eq.) MsCl (2.0 eq.) Reaction mixture was stirred at 0° C. for 2 hours | N/A | 57 |
| 15 | 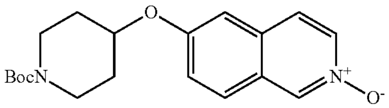 (1 eq.) | Reaction scale: 0.5 g 2-MeTHF/$H_2O$ (3 volumes/3 volumes) $K_3PO_4$ (3.0 eq.) MsCl (2.0 eq.) Reaction mixture was stirred at 0° C. for 2 hours | N/A | 59 |
| 16 | 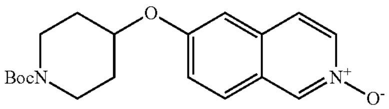 (1 eq.) | Reaction scale: 0.5 g 2-MeTHF/$H_2O$ (3 volumes/3 volumes) $K_2HPO_4$ (3.0 eq.) MsCl (2.0 eq.) Reaction mixture was stirred at 0° C. for 2 hours | N/A | 57 |
| 17 | 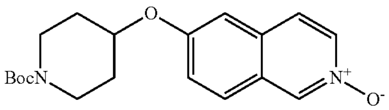 (1 eq.) | Reaction scale: 0.5 g THF/$H_2O$ (3 volumes/3 volumes) $K_2CO_3$ (3.0 eq.) MsCl (2.0 eq.) Reaction mixture was stirred at 0° C. for 2 hours | N/A | 77 |

TABLE III-continued

| # | Reactant, Compound of Formula (V) | Reaction Conditions | Yield % | Purity (area %) |
|---|---|---|---|---|
| 18 | 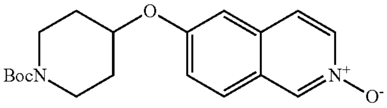<br>(1 eq.) | Reaction scale: 0.5 g<br>THF/$H_2O$<br>(3 volumes/3 volumes)<br>$K_2HPO_4$ (3.0 eq.)<br>MsCl (2.0 eq.)<br>Reaction mixture was stirred at 0° C. for 2 hours | N/A | 84 |
| 19 | 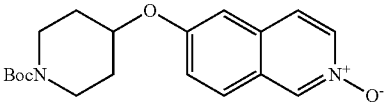<br>(1 eq.) | Reaction scale: 0.5 g<br>THF/$H_2O$<br>(3 volumes/3 volumes)<br>$K_3PO_4$ (3.0 eq.)<br>MsCl (2.0 eq.)<br>Reaction mixture was stirred at 0° C. for 2 hours | N/A | 60 |
| 20 | 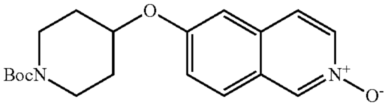<br>(1 eq.) | THF/$H_2O$<br>(4 volumes/4 volumes)<br>$NaHCO_3$ (3.0 eq.)<br>MsCl (2.0 eq.)<br>Reaction mixture was stirred at 22° C. for 2 hours | N/A | 90 |
| 21 | 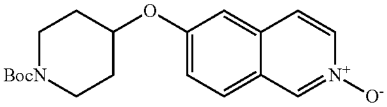<br>(1 eq.) | THF/$H_2O$<br>(30 volumes/10 volumes)<br>$NaHCO_3$ (3.0 eq.)<br>MsCl (2.0 eq.)<br>Reaction mixture was stirred at 22° C. for 2 hours | N/A (0.31 g) | 89.11 |
| 22 | 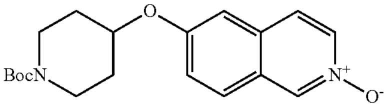<br>(1 eq.) | THF/$H_2O$<br>(4 volumes/4 volumes)<br>Triethylamine (TEA, 3.0 eq.)<br>MsCl (2.0 eq.)<br>Reaction mixture was stirred at 0° C. for 2 hours | N/A | 72.5 |
| 23 | 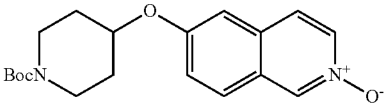<br>(1 eq.) | Reaction scale: 1 g<br>THF/$H_2O$<br>(10 volumes/10 volumes)<br>$NaHCO_3$ (3.0 eq.)<br>MsCl (2.0 eq.)<br>Reaction mixture was stirred at 0° C. for 2 hours | 40 (0.4 g) | 98.87 |
| 24 | 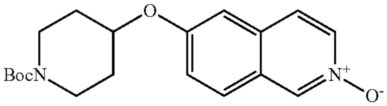<br>(1 eq.) | Reaction scale: 1 g<br>2-MeTHF/$H_2O$<br>(10 volumes/10 volumes)<br>$NaHCO_3$ (3.0 eq.)<br>MsCl (2.0 eq.)<br>Reaction mixture was stirred at 0° C. for 2 hours | 22 (0.22 g) | 99.04 |
| 25 | 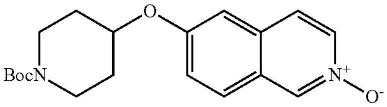<br>(1 eq.) | Reaction scale: 1 g<br>MeCN/$H_2O$<br>(10 volumes/10 volumes)<br>$NaHCO_3$ (3.0 eq.)<br>MsCl (2.0 eq.)<br>Reaction mixture was stirred at 0° C. for 2 hours | 52 (0.52 g) | 98.45 |
| 26 | 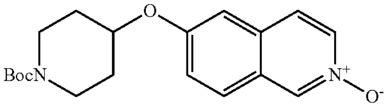<br>(1 eq.) | Reaction scale: 1 g<br>MeCN/$H_2O$<br>(10 volumes/10 volumes)<br>$NaHCO_3$ (3.0 eq.)<br>TEA (3 eq.)<br>MsCl (2.2 eq.)<br>Reaction mixture was stirred at 0° C. for 2 hours | 59 (0.92 g crude, 0.59 g by NMR assay) | 86.74 |

TABLE III-continued

| # | Reactant, Compound of Formula (V) | Reaction Conditions | Yield % | Purity (area %) |
|---|---|---|---|---|
| 27 | 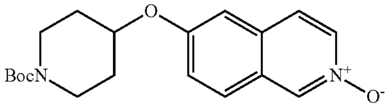 (1 eq.) | Reaction scale: 1 g<br>MeCN/$H_2O$<br>(10 volumes/10 volumes)<br>TEA (4 eq.)<br>MsCl (3 eq.)<br>Reaction mixture was stirred at 0° C. for 2 hours | 52 (0.52 g) | 99.12 |
| 28 | 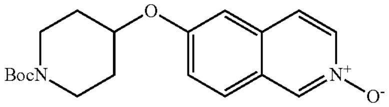 (1 eq.) | Reaction scale: 1 g<br>MeCN/$H_2O$<br>(10 volumes/10 volumes)<br>N,N-Diisopropylethylamine (DIPEA, 4 eq.)<br>MsCl (3 eq.)<br>Reaction mixture was stirred at 0° C. for 2 hours | 26 (0.26 g) | 99.38 |
| 29 | 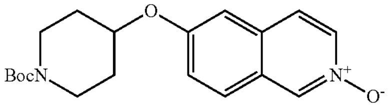 (1 eq.) | Reaction scale: 1 g<br>Acetone/$H_2O$<br>(10 volumes/10 volumes)<br>TEA (4 eq.)<br>MsCl (3 eq.)<br>Reaction mixture was stirred at 0° C. for 2 hours | 49 (0.49 g) | 98.84 |
| 30 | 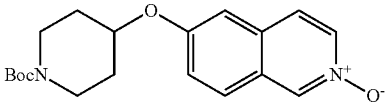 (1 eq.) | Reaction scale: 1 g<br>MeCN/$H_2O$<br>(5 volumes/10 volumes)<br>TEA (4 eq.)<br>MsCl (3 eq.)<br>Reaction mixture was stirred at 0° C. for 2 hours | 62 (0.62 g) | 98.73 |
| 31 | 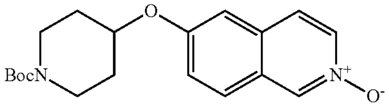 (1 eq.) | Reaction scale: 1 g<br>MeCN/$H_2O$<br>(2 volumes/10 volumes)<br>TEA (4 eq.)<br>MsCl (3 eq.)<br>Reaction mixture was stirred at 0° C. for 2 hours | N/A | 69.6 |
| 32 | 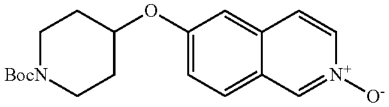 (1 eq.) | Reaction scale: 1 g<br>MeCN/$H_2O$<br>(10 volumes/5 volumes)<br>TEA (6 eq.)<br>MsCl (3 eq.)<br>Reaction mixture was stirred at 0° C. for 2 hours | 37 (0.37 g) | 97.79 |
| 33 | 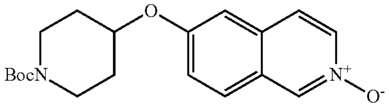 (1 eq.) | Reaction scale: 1 g<br>MeCN/$H_2O$<br>(10 volumes/2 volumes)<br>TEA (6 eq.)<br>MsCl (3 eq.)<br>Reaction mixture was stirred at 0° C. for 2 hours | N/A | 69 |
| 34 | 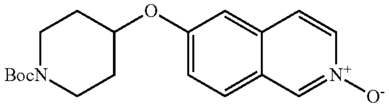 (1 eq.) | Reaction scale: 1 g<br>MeCN/$H_2O$<br>(8 volumes/8 volumes)<br>TEA (5 eq. initially, and an additional 1 eq., for 6 eq. total TEA)<br>MsCl (3 eq.)<br>Reaction mixture was stirred at 0° C. for 2 hours after addition of initial charge of TEA (5 eq.), then was stirred for an additional 1 hour at room temperature after addition of second charge of TEA (1 eq.) | 30 (0.30 g) | 93 |

TABLE III-continued

| # | Reactant, Compound of Formula (V) | Reaction Conditions | Yield % | Purity (area %) |
|---|---|---|---|---|
| 35 | 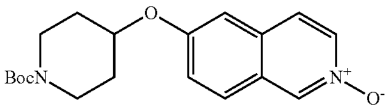 (1 eq.) | Reaction scale: 1 g<br>MeCN/$H_2O$<br>(5 volumes/5 volumes)<br>TEA (5 eq. initially, and an additional 1 eq., for 6 eq. total TEA)<br>MsCl (3 eq.)<br>Reaction mixture was stirred at 0° C. for 2 hours after addition of initial charge of TEA (5 eq.), then was stirred for an additional 1 hour at room temperature after addition of second charge of TEA (1 eq.) | N/A | 63.5 |
| 36 | 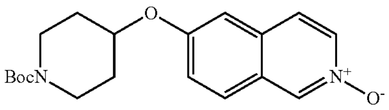 (1 eq.) | Reaction scale: 1 g<br>MeCN/$H_2O$<br>(4 volumes/10 volumes)<br>TEA (9 eq.)<br>MsCl (3 eq.)<br>Reaction mixture was stirred at 0° C. for 2 hours | N/A | 2.4 |
| 37 | 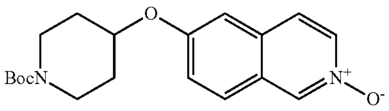 (1 eq.) | Reaction scale: 1 g<br>MeCN/$H_2O$<br>(9 volumes/2 volumes)<br>TEA (9 eq.)<br>MsCl (3 eq.)<br>Reaction mixture was stirred at 0° C. for 2 hours | N/A | 3.1 |
| 38 | 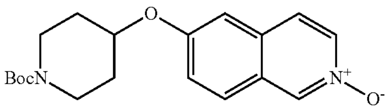 (1 eq.) | Reaction scale: 1 g<br>MeCN (25 volumes)<br>TEA (5 eq.)<br>MsCl (3 eq.)<br>Reaction mixture was stirred at 0° C. for 2 hours | N/A | 16.8 |
| 39 | 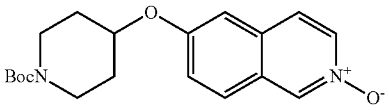 (1 eq.) | Reaction scale: 5 g<br>MeCN/$H_2O$<br>(10 volumes/10 volumes)<br>TEA (4.5 eq. initially, then second charge 1.5 eq., then third charge 0.75 eq., then fourth charge 0.75 eq., for 7.5 eq. total TEA)<br>MsCl (2 eq. initially, then second charge 1 eq., then third charge 0.5 eq., then fourth charge 0.5 eq., for 4 eq. total MsCl)<br>Reaction mixture was stirred at 0° C. for 2 hours after addition of initial charge of TEA (4.5 eq.) and MsCl (2 eq.), then was stirred for an additional 2 hours after addition of second charge of TEA (1.5 eq.) and second charge of MsCl (1 eq.), then was stirred for an additional 2 hours after addition of third charge of TEA (0.75 eq.) and third charge of MsCl (0.5 eq.), then was stirred for an additional 2 hours addition of fourth charge of TEA (0.75 eq.) and fourth charge of MsCl (0.5 eq.) | 39 (1.95 g) | 99.37 |

TABLE III-continued

| # | Reactant, Compound of Formula (V) | Reaction Conditions | Yield % | Purity (area %) |
|---|---|---|---|---|
| 40 | 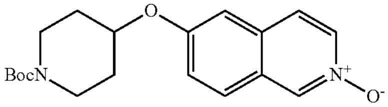 (1 eq.) | Reaction scale: 1 g<br>$MeCN/H_2O$<br>(10 volumes/10 volumes)<br>$NaH_2PO_4$ buffer<br>pH 4<br>MsCl (1 eq. initially, then a second charge of 1 eq., for 2 eq. total MsCl)<br>Reaction mixture was stirred at 0° C. for 2 hours | 55 (0.55 g) | 80.29 |
| 41 | 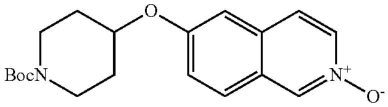 (1 eq.) | Reaction scale: 1 g<br>$MeCN/H_2O$<br>(10 volumes/10 volumes)<br>$NaH_2PO_4$ buffer<br>pH 6<br>MsCl (1 eq. initially, then a second charge of 1 eq., for 2 eq. total MsCl)<br>Reaction mixture was stirred at 0° C. for 2 hours | 45 (0.45 g) | 90.17 |
| 42 | 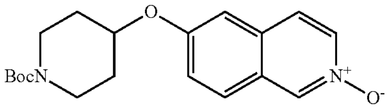 (1 eq.) | Reaction scale: 1 g<br>$MeCN/H_2O$<br>(10 volumes/10 volumes)<br>$NaH_2PO_4$ buffer<br>pH 8<br>MsCl (1 eq. initially, then a second charge of 1 eq., for 2 eq. total MsCl)<br>Reaction mixture was stirred at 0° C. for 2 hours | 65 (0.65 g, crude) | 88.89 |
| 43 | 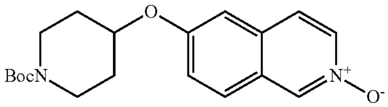 (1 eq.) | Reaction scale: 0.5 g<br>$MeCN/H_2O$<br>(5 volumes/15 volumes)<br>$H_3PO_4$/TEA buffer<br>pH 7<br>MsCl (2 eq.)<br>Reaction mixture was stirred at 0° C. for 2 hours | N/A | 81.5 |
| 44 | 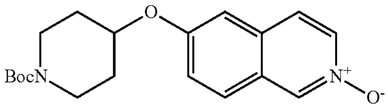 (1 eq.) | Reaction scale: 0.5 g<br>$MeCN/H_2O$<br>(5 volumes/15 volumes)<br>Citric acid/TEA buffer<br>pH 7<br>MsCl (2 eq. initially, then a second charge of 1 eq., for 3 eq. total MsCl)<br>Reaction mixture was stirred at 0° C. for 2 hours | N/A | 59 |
| 45 | 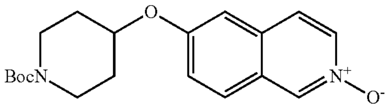 (1 eq.) | Reaction scale: 0.5 g<br>$MeCN/H_2O$<br>(5 volumes/20 volumes)<br>Citric acid buffer<br>pH 8<br>MsCl (2 eq. initially, then a second charge of 1 eq., for 3 eq. total MsCl)<br>Reaction mixture was stirred at 0° C. for 2 hours | N/A | 74.4 |
| 46 | 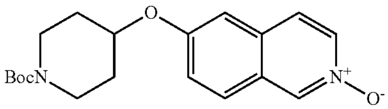 (1 eq.) | Reaction scale: 0.5 g<br>Isopropanol (iPrOH)/buffer<br>(5 volumes/10 volumes)<br>$H_3PO_4$/TEA buffer<br>pH 7<br>MsCl (2 eq.)<br>Reaction mixture was stirred at 0° C. for 2 hours | N/A | 72.5 |

TABLE III-continued

| # | Reactant, Compound of Formula (V) | Reaction Conditions | Yield % | Purity (area %) |
|---|---|---|---|---|
| 47 | 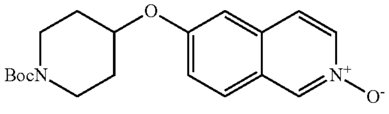 (1 eq.) | Reaction scale: 0.5 g iPrOH/buffer (5 volumes/10 volumes) MOPS/TEA buffer pH 7 MsCl (2 eq.) Reaction mixture was stirred at 0° C. for 2 hours | N/A | 80.5 |
| 48 | 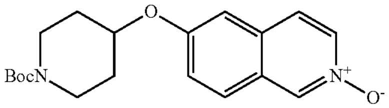 (1 eq.) | Reaction scale: 0.5 g THF/water (10 volumes/10 volumes) $NaHCO_3$ (4 eq.) MsCl (2 eq.) Reaction mixture was stirred at 0° C. for 2 hours | N/A (0.25 g) | 79.4 |
| 49 | 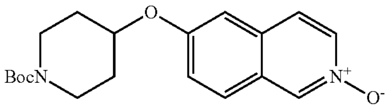 (1 eq.) | Reaction scale: 5 g THF/water (10 volumes/10 volumes) $NaHCO_3$ (4 eq.) MsCl (2 eq.) Reaction mixture was stirred at 0° C. for 2 hours | 58 (2.91 g) | 97.16 |
| 50 | 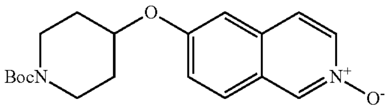 (1 eq.) | Reaction scale: 20 g THF/water (10 volumes/10 volumes) $NaHCO_3$ (4 eq.) MsCl (2 eq. initially, then a second charge of 0.1 eq., for 2.1 eq. total MsC1) Reaction mixture was stirred at 0° C. for 2 hours | N/A | N/A |
| 51 | 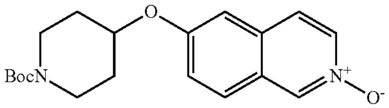 (1 eq.) | Reaction scale: 70 g THF/water (10 volumes/10 volumes) $NaHCO_3$ (5 eq.) MsCl (2 eq.) Reaction mixture was stirred at 0° C. for 2 hours | 69 (48.3 g) | 97.8 |
| 52 | 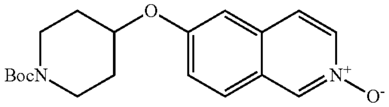 (1 eq.) | Reaction scale: 1200 g THF/water (10 volumes/10 volumes) $NaHCO_3$ (5 eq.) MsCl (2 eq.) Reaction mixture was stirred at 0° C. for 2 hours | 69 (823 g) | 98.2 |

Preferably, step C is followed by an optional deprotection step D, comprising removing the protecting group in a compound of formula (I), wherein $R_1$ is a protecting group as defined above, by reacting the compound of formula (I) with at least one deprotection reagent to produce a compound of formula (I), wherein $R_1$ is H.

Preferably, step D comprises reacting a compound of formula (I), wherein $R_1$ is a protecting group as defined above, to form a compound of formula (I) wherein $R_1$ is H in the presence of a deprotection reagent and a solvent.

Suitable deprotection reagents for use in step D may be selected from the group consisting of acyl halides, acid anhydrides, organic acids, inorganic acids, and mixtures thereof.

The deprotection reagent for use in step D may be an acyl halide selected from the group consisting of acyl chloride, acyl bromide, acyl iodide, and mixtures thereof.

The deprotection reagent for use in step D may be an acid anhydride selected from the group consisting of acetic anhydride, formic anhydride, acetic formic anhydride, trifluoroacetic anhydride, trimethylacetic anhydride, hexanoic anhydride, benzoic anhydride, and mixtures thereof.

The deprotection reagent for use in step D may be an organic acid selected from the group consisting of formic acid, acetic acid, trifluoroacetic acid, and mixtures thereof.

The deprotection reagent for use in step D may be an inorganic acid selected from the group consisting of hydrochloric acid, hydrobromic acid, hydroiodic acid, and mixtures thereof.

Suitable solvents for use in step D may be selected from the group consisting of alcohols, ethers, nitriles, halogenated alkanes, and mixtures thereof.

The solvent for use in step D may be an alcohol selected from the group consisting of methanol, ethanol, n-propanol, isopropanol, n-butanol, sec-butanol, isobutanol, tert-butanol, and mixtures thereof.

The solvent for use in step D may be an ether selected from the group consisting of diethyl ether, THF, 2-MeTHF, DME, MTBE, 1,4-dioxane, and mixtures thereof.

The solvent for use in step D may be a nitrile selected from the group consisting of MeCN, propionitrile, benzonitrile, and mixtures thereof.

The solvent for use in step D may be a halogenated alkane selected from the group consisting of DCM, chloroform, carbon tetrachloride, 1,2-dichloroethane, and mixtures thereof.

Preferably, the deprotection reagent is selected from the group consisting of acyl chloride, acyl bromide, acetic anhydride, formic anhydride, acetic formic anhydride, hydrochloric acid, hydrobromic acid, hydroiodic acid, acetic acid, formic acid, trifluoroacetic acid, and mixtures thereof.

Preferably, the solvent is selected from the group consisting of methanol, ethanol, isopropanol, diethyl ether, THF, 2-MeTHF, MeCN, DCM, chloroform, and mixtures thereof.

Preferably, the deprotection reagent is acyl chloride and the solvent is isopropanol.

Preferably, the deprotection reagent is hydrochloric acid and the solvent is THF. Preferably, the deprotection reagent is trifluoroacetic acid and the solvent is DCM.

Preferably, the amount of deprotection reagent to compound of formula (I), wherein $R_1$ is a protecting group as defined above, is in the range of 1 to 20 molar equivalents. Preferably, the range is 2 to 17.5 molar equivalents. Preferably, the range is 3 to 15 molar equivalents.

Preferably, the range is 4 to 12.5 molar equivalents. Preferably, the amount of deprotection reagent to compound of formula (I), wherein $R_1$ is a protecting group as defined above, is about 5 molar equivalents. Preferably, the amount of deprotection reagent to compound of formula (I), wherein $R_1$ is a protecting group as defined above, is about 7.5 molar equivalents. Preferably, the amount of deprotection reagent to compound of formula (I), wherein $R_1$ is a protecting group as defined above, is about 8 molar equivalents. Preferably, the amount of deprotection reagent to compound of formula (I), wherein $R_1$ is a protecting group as defined above, is about 9 molar equivalents. Preferably, the amount of deprotection reagent to compound of formula (I), wherein $R_1$ is a protecting group as defined above, is about 10 molar equivalents. Preferably, the amount of deprotection reagent to compound of formula (I), wherein $R_1$ is a protecting group as defined above, is about 12.5 molar equivalents. Preferably, the amount of deprotection reagent to compound of formula (I), wherein $R_1$ is a protecting group as defined above, is in the range of 1 to 10 molar equivalents. Preferably, the range is 1.5 to 7.5 molar equivalents. Preferably, the range is 2 to 5 molar equivalents. Preferably, the amount of deprotection reagent to compound of formula (I), wherein $R_1$ is a protecting group as defined above, is about 2 molar equivalents.

Preferably, the amount of deprotection reagent to compound of formula (I), wherein $R_1$ is a protecting group as defined above, is about 2.5 molar equivalents. Preferably, the amount of deprotection reagent to compound of formula (I), wherein $R_1$ is a protecting group as defined above, is about 3 molar equivalents. Preferably, the amount of deprotection reagent to compound of formula (I), wherein $R_1$ is a protecting group as defined above, is about 4 molar equivalents.

Step D may be conducted using a compound of formula (I) or a pharmaceutically acceptable salt thereof. Step D may result in a compound of formula (I), wherein $R_1$ is H, or in a pharmaceutically acceptable salt thereof.

Preferably, step D is carried out from about −10° C. to about 70° C. Preferably, step D is carried out from about −5° C. to about 60° C. Preferably, step D is carried out from about 0° C. to about 50° C. Preferably, step D is carried out from about 5° C. to about 40° C. Preferably, step D is carried out from about 10° C. to about 35° C. Preferably, step D is carried out from about 15° C. to about 30° C. Preferably, step D is carried out at room temperature.

Examples of Step D are shown in Scheme 5 and Table IV below. Scheme 5 provides an example of a Step D reaction, and Table IV provides reaction conditions used in the reaction shown in Scheme 5.

Scheme 5

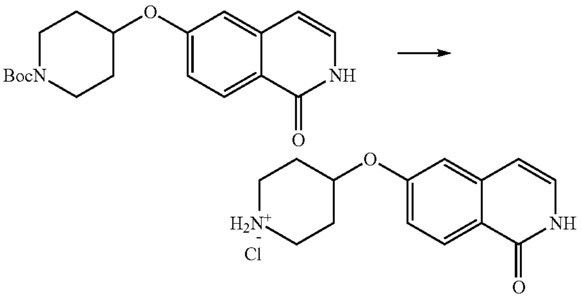

Although the reactant of Scheme 5, which is a compound of formula (I) wherein $R_1$ is a tert-butyloxycarbonyl (BOC) group, is shown in a lactam form, it may also be in a lactim form or in an equilibrium of both forms, as shown below:

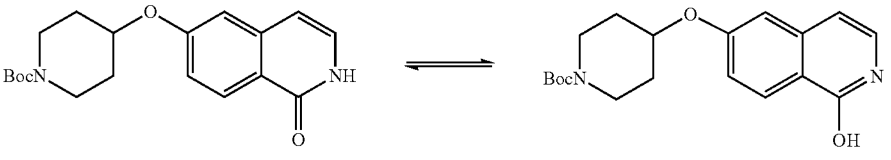

Further, although the product of Scheme 5, which is a compound of formula (I) wherein $R_1$ is H, is shown in a lactam form, it may also be in a lactim form or in an equilibrium of both forms, as shown below:

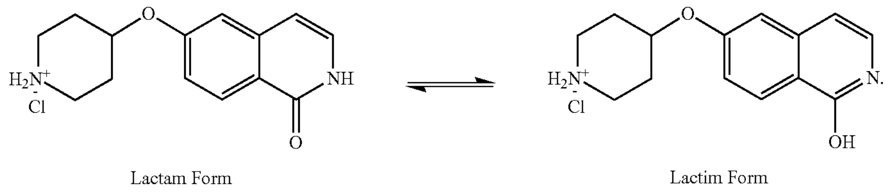 [SMILES: Cl ; O=c1[nH]ccc2cc(OC3CC[NH2+]CC3)ccc12 ; Cl ; Oc1nccc2cc(OC3CC[NH2+]CC3)ccc12]

Further, although the product of Scheme 5, which is a compound of formula (I) wherein $R_1$ is H, is shown as a monohydrochloride salt, it may also be a dihydrochloride salt. In addition, the dihydrochloride salt may be in a lactam form, in a lactim form, or in an equilibrium of both forms, as shown below:

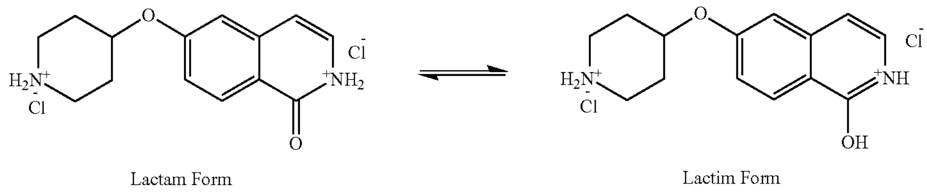 [SMILES: Cl ; O=C1[NH2+]C=Cc2cc(OC3CC[NH2+]CC3)ccc21 ; Cl ; Cl ; Oc1[nH+]ccc2cc(OC3CC[NH2+]CC3)ccc12 ; Cl]

TABLE IV

| # | Reactant, Compound of Formula (I) | Reaction Conditions | Yield % | Purity (area %) |
|---|---|---|---|---|
| 1 | 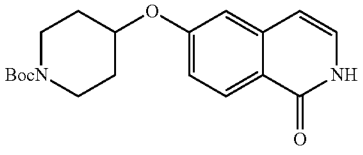 (1 eq.) | Reaction scale: 0.2 g<br>12M HCl (10.0 eq.)<br>Butanol (BuOH, 8 volumes)<br>HCl was added at 5-10° C., then the reaction mixture was stirred as the temperature warmed to room temperature for a total of 16 hours | 26.5 (0.0432 g) | 99.7 |
| 2 | 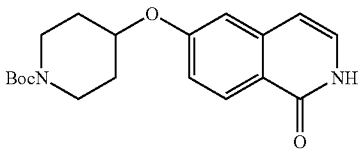 (1 eq.) | Reaction scale: 0.2 g<br>Acyl chloride (AcCl, 10.0 eq.)<br>Butanol (BuOH, 8 volumes)<br>AcCl was added at 5-10° C., then the reaction mixture was stirred as the temperature warmed to room temperature for a total of 16 hours | 76.8 (0.1012 g) | 99.5 |
| 3 | 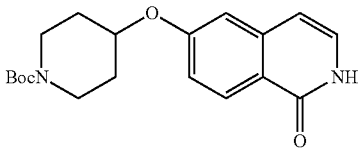 (1 eq.) | Reaction scale: 0.2 g<br>2M HCl (10.0 eq.)<br>Tetrahydrofuran (THF, 8 volumes)<br>HCl was added at 5-10° C., then the reaction mixture was stirred as the temperature warmed to room temperature for a total of 16 hours | N/A | 84.7 |

TABLE IV-continued

| # | Reactant, Compound of Formula (I) | Reaction Conditions | Yield % | Purity (area %) |
|---|---|---|---|---|
| 4 | 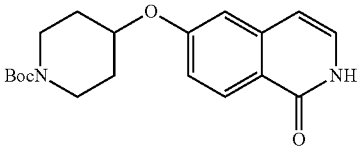 (1 eq.) | Reaction scale: 0.2 g<br>Trifluoroacetic acid<br>(TFA, 10.9 eq., 2.5 volumes)<br>DCM (10 volumes)<br>Reaction mixtures was stirred at room temperature for 2 hours | 129 (0.268 g) | 97.2 |
| 5 | 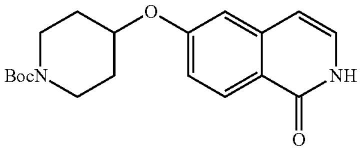 (1 eq.) | Reaction scale: 8 g<br>AcCl (7.5 eq.)<br>Isopropanol (iPrOH)<br>(10 volumes)<br>Reaction mixtures was stirred at room temperature for 16 hours | 99.3 (6.47 g) | 99.55 |
| 6 | 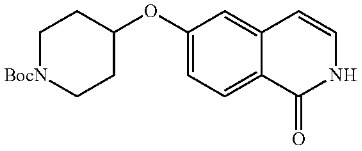 (1 eq.) | Reaction scale: 5.5 g<br>AcCl (7.5 eq.)<br>iPrOH (10 volumes)<br>Reaction mixture was stirred at room temperature for 16 hours | 93 (4.2 g) | 98.4 |
| 7 | 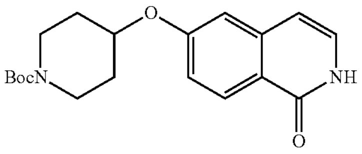 (1 eq.) | Reaction scale: 2 g<br>AcCl (7.5 eq. initially, then second charge of 5 eq., for 12.5 eq. total AcCl),<br>iPrOH (10 volumes)<br>Reaction mixture was stirred at room temperature for 16 hours after initial charge of AcCl, then for another 3 hours at room temperature after second charge of AcCl | 88 (1.43 g) | 99.53 |
| 8 | 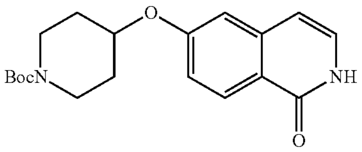 (1 eq.) | Reaction scale: 3 g<br>AcCl (7.5 eq. initially, then second charge of 2.5 eq., for 10 eq. total AcCl)<br>iPrOH (10 volumes)<br>Reaction mixture was stirred at room temperature for 16 hours after initial charge of AcCl, then for another 16 hours at room temperature after second charge of AcCl | 103 (2.5 g) | 99.77 |
| 9 | 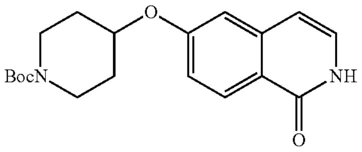 (1 eq.) | Reaction scale: 2.5 g<br>AcCl (10 eq.)<br>iPrOH (5 volumes)<br>Reaction mixture was stirred at room temperature for 16 hours | 84 (1.71 g) | 94.3 |
| 10 | 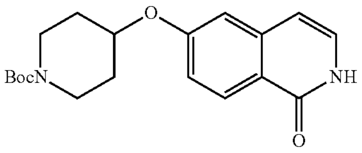 (1 eq.) | Reaction scale: 21.5 g<br>AcCl (7.5 eq.)<br>iPrOH (10 volumes)<br>Reaction mixture was stirred at 30° C. for 16 hours | 93 (18.7 g) | 99.0 |
| 11 | | Reaction scale: 45 g | 98 (39.7 g) | 98.7 |

Preferably, step A is optionally followed by a deprotection step E, comprising removing the protecting group in a compound of formula (IV), wherein $R_1$ is a protecting group as defined above, by reacting the compound of formula (IV) with at least one deprotection reagent to produce a compound of formula (IV), wherein $R_1$ is H.

Preferably, step E comprises reacting a compound of formula (IV), wherein $R_1$ is a protecting group as defined above, to form a compound of formula (IV) wherein $R_1$ is H in the presence of a deprotection reagent and a solvent.

Suitable deprotection reagents for use in step E may be selected from the group consisting of acyl halides, acid anhydrides, organic acids, inorganic acids, and mixtures thereof.

The deprotection reagent for use in step E may be an acyl halide selected from the group consisting of acyl chloride, acyl bromide, acyl iodide, and mixtures thereof.

The deprotection reagent for use in step E may be an acid anhydride selected from the group consisting of acetic anhydride, formic anhydride, acetic formic anhydride, trifluoroacetic anhydride, trimethylacetic anhydride, hexanoic anhydride, benzoic anhydride, and mixtures thereof.

The deprotection reagent for use in step E may be an organic acid selected from the group consisting of formic acid, acetic acid, trifluoroacetic acid, and mixtures thereof.

The deprotection reagent for use in step E may be an inorganic acid selected from the group consisting of hydrochloric acid, hydrobromic acid, hydroiodic acid, and mixtures thereof.

Suitable solvents for use in step E may be selected from the group consisting of alcohols, ethers, nitriles, halogenated alkanes, and mixtures thereof.

The solvent for use in step E may be an alcohol selected from the group consisting of methanol, ethanol, n-propanol, isopropanol, n-butanol, sec-butanol, isobutanol, tert-butanol, and mixtures thereof.

The solvent for use in step E may be an ether selected from the group consisting of diethyl ether, THF, 2-MeTHF, DME, MTBE, 1,4-dioxane, and mixtures thereof.

The solvent for use in step E may be a nitrile selected from the group consisting of MeCN, propionitrile, benzonitrile, and mixtures thereof.

The solvent for use in step E may be a halogenated alkane selected from the group consisting of DCM, chloroform, carbon tetrachloride, 1,2-dichloroethane, and mixtures thereof.

Preferably, the deprotection reagent is selected from the group consisting of acyl chloride, acyl bromide, acetic anhydride, formic anhydride, acetic formic anhydride, hydrochloric acid, hydrobromic acid, hydroiodic acid, acetic acid, formic acid, trifluoroacetic acid, and mixtures thereof.

Preferably, the solvent is selected from the group consisting of methanol, ethanol, isopropanol, diethyl ether, THF, 2-MeTHF, MeCN, DCM, chloroform, and mixtures thereof.

Preferably, the deprotection reagent is acyl chloride and the solvent is isopropanol. Preferably, the deprotection reagent is hydrochloric acid and the solvent is THF. Preferably, the deprotection reagent is trifluoroacetic acid and the solvent is DCM.

According to a preferred embodiment of the invention the amount of deprotection reagent to compound of formula (IV), wherein $R_1$ is a protecting group as defined above, is in the range of 1 to 20 molar equivalents. Preferably, the range is 2 to 17.5 molar equivalents. Preferably, the range is 3 to 15 molar equivalents. Preferably, the range is 4 to 12.5 molar equivalents.

Preferably, the amount of deprotection reagent to compound of formula (IV), wherein $R_1$ is a protecting group as defined above, is about 5 molar equivalents. Preferably, the amount of deprotection reagent to compound of formula (IV), wherein $R_1$ is a protecting group as defined above, is about 7.5 molar equivalents. Preferably, the amount of deprotection reagent to compound of formula (IV), wherein $R_1$ is a protecting group as defined above, is about 8 molar equivalents. Preferably, the amount of deprotection reagent to compound of formula (IV), wherein $R_1$ is a protecting group as defined above, is about 9 molar equivalents. Preferably, the amount of deprotection reagent to compound of formula (IV), wherein $R_1$ is a protecting group as defined above, is about 10 molar equivalents. Preferably, the amount of deprotection reagent to compound of formula (IV), wherein $R_1$ is a protecting group as defined above, is about 12.5 molar equivalents. Preferably, the amount of deprotection reagent to compound of formula (IV), wherein $R_1$ is a protecting group as defined above, is in the range of 1 to 10 molar equivalents.

Preferably, the range is 1.5 to 7.5 molar equivalents. Preferably, the range is 2 to 5 molar equivalents. Preferably, the amount of deprotection reagent to compound of formula (IV), wherein $R_1$ is a protecting group as defined above, is about 2 molar equivalents. Preferably, the amount of deprotection reagent to compound of formula (IV), wherein $R_1$ is a protecting group as defined above, is about 2.5 molar equivalents. Preferably, the amount of deprotection reagent to compound of formula (IV), wherein $R_1$ is a protecting group as defined above, is about 3 molar equivalents. Preferably, the amount of deprotection reagent to compound of formula (IV), wherein $R_1$ is a protecting group as defined above, is about 4 molar equivalents.

Step E may be conducted using a compound of formula (IV) or a pharmaceutically acceptable salt thereof. Step E may result in a compound of formula (IV), wherein $R_1$ is H, or in a pharmaceutically acceptable salt thereof.

Preferably, step E is carried out from about −10° C. to about 70° C. Preferably, step E is carried out from about −5° C. to about 60° C. Preferably, step E is carried out from about 0° C. to about 50° C. Preferably, step E is carried out from about 5° C. to about 40° C. Preferably, step E is carried out from about 10° C. to about 35° C. Preferably, step E is carried out from about 15° C. to about 30° C. Preferably, step E is carried out at room temperature.

Preferably, step B is optionally followed by a deprotection step F, comprising removing the protecting group in a compound of formula (V), wherein $R_1$ is a protecting group as defined above, by reacting the compound of formula (V) with at least one deprotection reagent to produce a compound of formula (V), wherein $R_1$ is H.

Preferably, step F comprises reacting a compound of formula (V), wherein $R_1$ is a protecting group as defined above, to form a compound of formula (V) wherein $R_1$ is H in the presence of a deprotection reagent and a solvent.

Suitable deprotection reagents for use in step F may be selected from the group consisting of acyl halides, acid anhydrides, organic acids, inorganic acids, and mixtures thereof.

The deprotection reagent for use in step F may be an acyl halide selected from the group consisting of acyl chloride, acyl bromide, acyl iodide, and mixtures thereof.

The deprotection reagent for use in step F may be an acid anhydride selected from the group consisting of acetic anhydride, formic anhydride, acetic formic anhydride, trifluoroacetic anhydride, trimethylacetic anhydride, hexanoic anhydride, benzoic anhydride, and mixtures thereof.

The deprotection reagent for use in step F may be an organic acid selected from the group consisting of formic acid, acetic acid, trifluoroacetic acid, and mixtures thereof.

The deprotection reagent for use in step F may be an inorganic acid selected from the group consisting of hydrochloric acid, hydrobromic acid, hydroiodic acid, and mixtures thereof.

Suitable solvents for use in step F may be selected from the group consisting of alcohols, ethers, nitriles, halogenated alkanes, and mixtures thereof.

The solvent for use in step F may be an alcohol selected from the group consisting of methanol, ethanol, n-propanol, isopropanol, n-butanol, sec-butanol, isobutanol, tert-butanol, and mixtures thereof.

The solvent for use in step F may be an ether selected from the group consisting of diethyl ether, THF, 2-MeTHF, DME, MTBE, 1,4-dioxane, and mixtures thereof.

The solvent for use in step F may be a nitrile selected from the group consisting of MeCN, propionitrile, benzonitrile, and mixtures thereof.

The solvent for use in step F may be a halogenated alkane selected from the group consisting of DCM, chloroform, carbon tetrachloride, 1,2-dichloroethane, and mixtures thereof.

Preferably, the deprotection reagent is selected from the group consisting of acyl chloride, acyl bromide, acetic anhydride, formic anhydride, acetic formic anhydride, hydrochloric acid, hydrobromic acid, hydroiodic acid, acetic acid, formic acid, trifluoroacetic acid, and mixtures thereof.

The solvent is selected from the group consisting of methanol, ethanol, isopropanol, diethyl ether, THF, 2-MeTHF, MeCN, DCM, chloroform, and mixtures thereof.

Preferably, the deprotection reagent is acyl chloride and the solvent is isopropanol. Preferably, the deprotection reagent is hydrochloric acid and the solvent is THF. Preferably, the deprotection reagent is trifluoroacetic acid and the solvent is DCM.

According to a preferred embodiment of the invention the amount of deprotection reagent to compound of formula (V), wherein $R_1$ is a protecting group as defined above, is in the range of 1 to 20 molar equivalents, preferably 2 to 17.5 molar equivalents, more preferably 3 to 15 molar equivalents, further preferably 4 to 12.5 molar equivalents, for example about 5, about 7.5, about 8, about 9, about 10, or about 12.5 molar equivalents. Further preferably, the amount of deprotection reagent to compound of formula (V), wherein $R_1$ is a protecting group as defined above, is in the range of 1 to 10, 1.5 to 7.5, or 2 to 5 molar equivalents. The amount of deprotection reagent to compound of formula (V), wherein $R_1$ is a protecting group as defined above, may be about 2, about 2.5, about 3, or about 4 molar equivalents.

Step F may be conducted using a compound of formula (V) or a pharmaceutically acceptable salt thereof. Step F may result in a compound of formula (V), wherein $R_1$ is H, or in a pharmaceutically acceptable salt thereof.

Preferably, step F is carried out from about −10° C. to about 70° C. Preferably, step F is carried out from about −5° C. to about 60° C. Preferably, step F is carried out from about 0° C. to about 50° C. Preferably, step F is carried out from about 5° C. to about 40° C. Preferably, step F is carried out from about 10° C. to about 35° C. Preferably, step F is carried out from about 15° C. to about 30° C. Preferably, step F is carried out at room temperature.

Compounds of formula of formula (I), formula (II), formula (III), formula (IV), and formula (V) may exist as pharmaceutically acceptable salts.

Pharmaceutically acceptable salts of compounds of formula (I), formula (II), formula (III), formula (IV), and formula (V) may be prepared from inorganic acids such as hydrochloric acid, hydrobromic acid, hydroiodic acid, phosphoric acid, metaphosphoric acid, nitric acid, and sulfuric acid, and of organic acids such as, for example, formic acid, acetic acid, trifluoroacetic acid, benzenesulfonic acid, benzoic acid, citric acid, ethanesulfonic acid, fumaric acid, gluconic acid, glycolic acid, lactic acid, maleic acid, malic acid, methanesulfonic acid, succinic acid, p-toluenesulfonic acid, and tartaric acid by methods known in the art. In the pharmaceutically acceptable salts of compounds of formula (I), formula (II), formula (III), formula (IV), and formula (V), the ratio of inorganic acid or organic acid to a compound of formula (I), formula (II), formula (III), formula (IV), or formula (V) is between 1 and 5 molar equivalents of inorganic acid or organic acid to 1 molar equivalent of a compound of formula (I), formula (II), formula (III), formula (IV), or formula (V). Preferably, the ratio of inorganic acid or organic acid to a compound of formula (I), formula (II), formula (III), formula (IV), or formula (V) is 1 molar equivalent of inorganic acid or organic acid to 1 molar equivalent of a compound of formula (I), formula (II), formula (III), formula (IV), or formula (V). Preferably, the ratio of inorganic acid or organic acid to a compound of formula (I), formula (II), formula (III), formula (IV), or formula (V) is 2 molar equivalents of inorganic acid or organic acid to 1 molar equivalent of a compound of formula (I), formula (II), formula (III), formula (IV), or formula (V).

Pharmaceutically acceptable salts of compounds of formula (I), formula (II), formula (III), formula (IV), and formula (V) may exist as hydrates. The stoichiometry of water molecules to molecules of the salts of the pharmaceutically acceptable salts of compounds of formula (I), formula (II), formula (III), formula (IV), and formula (V) depends on how tightly bound water is to the respective salt and on humidity.

Preferably, hydrates of compounds of formula (I), formula (II), formula (III), formula (IV), formula (V), or pharmaceutically acceptable salts thereof may be formed by dissolving or suspending the compounds of formula (I), formula (II), formula (III), formula (IV), formula (V), or pharmaceutically acceptable salts thereof in water or in a mixture of water and an organic solvent in an optional step G.

Preferably, hydrates of compounds of formula (I), formula (II), formula (III), formula (IV), formula (V), or pharmaceutically acceptable salts thereof are formed in step G by dissolving or suspending the compounds of formula (I), formula (II), formula (III), formula (IV), formula (V), or pharmaceutically acceptable salts thereof in water.

Preferably, hydrates of compounds of formula (I), formula (II), formula (III), formula (IV), formula (V), or pharmaceutically acceptable salts thereof are formed in step G by dissolving or suspending the compounds of formula (I), formula (II), formula (III), formula (IV), formula (V), or pharmaceutically acceptable salts thereof in a mixture of water and an organic solvent.

Suitable organic solvents for use in step G are nitriles, such as MeCN or propionitrile; ketones, such as acetone; ethers, such as THF; and alcohols, such as methanol, ethanol, n-propanol, and isopropanol.

Preferably, hydrates of compounds of formula (I), formula (II), formula (III), formula (IV), formula (V), or pharmaceutically acceptable salts thereof are formed in step G by dissolving or suspending the compounds of formula (I), formula (II), formula (III), formula (IV), formula (V), or pharmaceutically acceptable salts thereof in a mixture of water and MeCN, acetone, THF, methanol, ethanol, n-propanol, or isopropanol.

Preferably, the ratio of volumes of water to volumes of organic solvent in step G is in the range of 1:10 to 10:1. Preferably, the ratio of volumes of water to volumes of organic solvent in step G is in the range of 1:9 to 9:1. Preferably, the ratio of volumes of water to volumes of organic solvent in step G is in the range of 1:8 to 8:1. Preferably, the ratio of volumes of water to volumes of organic solvent in step G is in the range of 1:7 to 7:1. Preferably, the ratio of volumes of water to volumes of organic solvent in step G is in the range of 1:6 to 6:1.

Preferably, the ratio of volumes of water to volumes of organic solvent in step G is in the range of 1:5 to 5:1. Preferably, the ratio of volumes of water to volumes of organic solvent in step G is in the range of 1:4 to 4:1. Preferably, the ratio of volumes of water to volumes of organic solvent in step G is in the range of 1:3 to 3:1. Preferably, the ratio of volumes of water to volumes of organic solvent in step G is in the range of 1:2 to 2:1. Preferably, the ratio of volumes of water to volumes of organic solvent in step G is 1:1. Preferably, the ratio of volumes of water to volumes of organic solvent in step G is 2:1. Preferably, the ratio of volumes of water to volumes of organic solvent in step G is 1:2. Preferably, the ratio of volumes of water to volumes of organic solvent in step G is 2:3. Preferably, the ratio of volumes of water to volumes of organic solvent in step G is 3:2. Preferably, the ratio of volumes of water to volumes of organic solvent in step G is 4:3. Preferably, the ratio of volumes of water to volumes of organic solvent in step G is 3:4. Preferably, the ratio of volumes of water to volumes of organic solvent in step G is 5:3. Preferably, the ratio of volumes of water to volumes of organic solvent in step G is 3:5.

Preferably, step G is carried out from about −10° C. to about 100° C. Preferably, step G is carried out from about −5° C. to about 90° C. Preferably, step G is carried out from about 0° C. to about 80° C. Preferably, step G is carried out from about 5° C. to about 75° C. Preferably, step G is carried out from about 10° C. to about 70° C. Preferably, step G is carried out from about 15° C. to about 65° C. Preferably, step G is carried out from about 20° C. to about 60° C. Preferably, step G is carried out from about 25° C. to about 55° C. Preferably, step G is carried out at about 65° C. Preferably, step G is carried out at about 60° C. Preferably, step G is carried out at about 55° C. Preferably, step G is carried out at about 50° C. Preferably, step G is carried out at about 45° C. Preferably, step G is carried out at about 40° C. Preferably, step G is carried out at about 35° C. Preferably, step G is carried out at about 30° C. Preferably, step G is carried out at about 25° C. Preferably, step G is carried out at about 20° C.

Examples of Step G are shown in Scheme 6 and Table V below. Scheme 6 provides an example of a Step G reaction, and Table V provides reaction conditions used in the reaction shown in Scheme 6.

Scheme 6

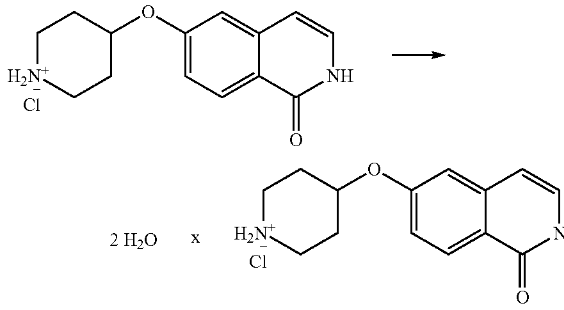

Although the reactant of Scheme 6 is shown in a lactam form, it may also be in a lactim form or in an equilibrium of both forms, as shown below:

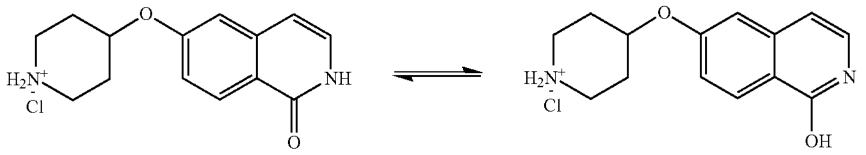

Lactam Form Lactim Form

Further, although the product of Scheme 6 is shown in a lactam form, it may also be in a lactim form or in an equilibrium of both forms, as shown below:

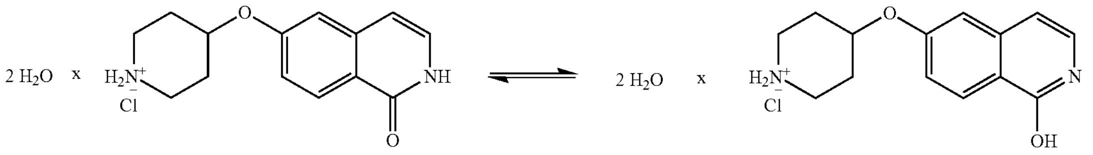

Lactam Form Lactim Form

TABLE V

| # | Reactant, Salt of Compound of Formula (I) | Reaction Conditions | Yield % | Purity (area %) |
|---|---|---|---|---|
| 1 | 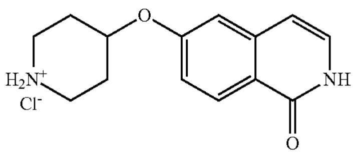 (1 eq.) | Reaction scale: 5 g Reactant dissolved in water (2 volumes) at 65° C., then cooled to 50° C. and added acetone (3 volumes) over 30 minutes, then cooled to 20° C. | 70 (3.5 g) | 99.9 |
| 2 | 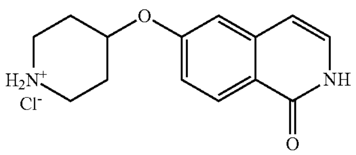 (1 eq.) | Reaction scale: 4 g Reactant dissolved in water (2 volumes) at 65° C., then cooled to 50° C. and added acetone (4 volumes) over 30 minutes, then cooled to 5° C. | N/A (2.2 g, uncorrected) | 99.9 |

All reaction steps are conducted until they are complete, as determined by standard laboratory techniques. For example, a step may be determined to be complete when at least one reagent is no longer detected in the reaction mixture. Alternatively, a step may be determined to be complete when no changes in concentrations of reagents, reaction products, or both are detected in the reaction mixture. Detection of reagents, products, or both can be conducted using standard laboratory techniques and instruments. For example, reagents, products, or both are monitored using thin layer chromatography, gas chromatography, or liquid chromatography.

Product obtained from each reaction step can be isolated and further purified by standard synthetic techniques. For example, isolation may be done by evaporation of the reaction mixture followed by a regular aqueous work-up and a subsequent chromatographic purification or crystallization of the product. Alternatively, the product contained in the reaction mixture may also be precipitated directly from the reaction mixture by adding a suitable anti-solvent such as water and/or alcohols.

The amount of solvent used in any step is determined by standard laboratory techniques. For example, a solvent may be used in an amount wherein all reagents in a step are dissolved in the solvent. Alternatively, a solvent may be used in an amount to control the reaction rate of a step.

Definitions

The term "alcohol" refers to compounds of formula R'—OH. R' may be a substituted or unsubstituted alkyl group, such as a substituted or unsubstituted $C_1$-$C_{10}$ alkyl group; a substituted or unsubstituted cyclic alkyl group, such as a substituted or unsubstituted $C_3$-$C_{10}$ cyclic alkyl group; a substituted or unsubstituted aryl group, such as a substituted or unsubstituted phenyl group. Examples of alcohols include methanol, ethanol, n-propanol, isopropanol, n-butanol, sec-butanol, isobutanol, and tert-butanol.

The term "alkane" refers to straight or branched hydrocarbons having 1 to 20 carbon atoms, and "substituted alkane" refers to straight or branched hydrocarbons having 1 to 20 carbon atoms further bearing one or more substituents.

The term "alkyl" refers to straight or branched chain alkyl radicals having 1 to 20 carbon atoms, and "substituted alkyl" refers to alkyl radicals further bearing one or more substituents.

The term "amide" refers to compounds of formula R'—C(O)—NR"R"'. R' may be H; a substituted or unsubstituted alkyl group, such as a substituted or unsubstituted $C_1$-$C_{10}$ alkyl group; or a substituted or unsubstituted aryl group; such as a substituted or unsubstituted phenyl group. R" may be H; a substituted or unsubstituted alkyl group, such as a substituted or unsubstituted $C_1$-$C_{10}$ alkyl group; or a substituted or unsubstituted aryl group, such as a substituted or unsubstituted phenyl group. R"' may be H; a substituted or unsubstituted alkyl group, such as a substituted or unsubstituted $C_1$-$C_{10}$ alkyl group; or a substituted or unsubstituted aryl group, such as a substituted or unsubstituted phenyl group. Two or more of R', R", and R"' may be the same, or all of R', R", and R"' may be different. Two of R', R", and R"' together may be a substituted or unsubstituted cyclic alkyl group, such as a substituted or unsubstituted $C_3$-$C_{10}$ cyclic alkyl group. Examples of amides include dimethylformamide, dimethylacetamide, and 2-pyrrolidone.

The term "aryl" refers to aromatic groups having 6 to 24 carbon atoms, and "substituted aryl" refers to aryl groups further bearing one or more substituents.

The term "buffer" refers to a solution that can resist changes of pH upon addition of an acid or a base.

The term "aqueous solution" refers to a solution comprising water and a solute selected from the group consisting of a salt, an acid, a base, a buffer, a water-soluble or water-miscible organic solvent, and mixtures thereof.

The term "catalyst" refers to a reagent capable of enhancing the rate of a chemical reaction and is selected from the group consisting of organic, inorganic, or organometallic compounds. Examples of catalysts include methyltrioxorhenium(VII), phosphomolybdic acid, hydrofluoric acid, hydrochloric acid, hydrobromic acid, hydroiodic acid, acetic acid, trifluoroacetic acid, triethylamine, pyridine, 4-dimethylaminopyridine, N,N'-dicyclohexylcarbodiimide, and 4-pyrrolidinylpyridine.

The term "cycloalkyl" refers to cyclic ring-containing moieties containing 3 to 20 carbon atoms, and "substituted cycloalkyl" refers to cycloalkyl moieties further bearing one or more substituents.

The terms "electrophile" and "electrophilic reagent" refer to a Lewis acid. Examples of electrophilic reagents include alkyl halides, acyl halides, acid anhydrides, and sulfonyl halide reagents.

The term "ester" refers to compounds of formula R'—C(O)—O—R". R' may be a substituted or unsubstituted alkyl group, such as a substituted or unsubstituted $C_1$-$C_{10}$ alkyl group or; or a substituted or unsubstituted aryl group, such as a substituted or unsubstituted phenyl group. R" may be a substituted or unsubstituted alkyl group, such as a substituted or unsubstituted $C_1$-$C_{10}$ alkyl group or; or a substituted or unsubstituted aryl group, such as a substituted or unsubstituted phenyl group. R' and R" may be the same. R' and R" may be different. R' and R" together may form a substituted or unsubstituted cyclic alkyl group, such as a substituted or unsubstituted $C_3$-$C_{10}$ cyclic alkyl group. Examples of esters include methyl acetate, ethyl acetate, and mixtures thereof.

The term "ether" refers to compounds of formula R'—O—R". R' may be a substituted or unsubstituted alkyl group, such as a substituted or unsubstituted $C_1$-$C_{10}$ alkyl group or; or a substituted or unsubstituted aryl group, such as a substituted or unsubstituted phenyl group. R" may be a substituted or unsubstituted alkyl group, such as a substituted or unsubstituted $C_1$-$C_{10}$ alkyl group or; or a substituted or unsubstituted aryl group, such as a substituted or unsubstituted phenyl group. R' and R" may be the same. R' and R" may be different. R' and R" together may form a substituted or unsubstituted cyclic alkyl group, such as a substituted or unsubstituted $C_3$-$C_{10}$ cyclic alkyl group. Examples of ethers include THF, 2-MeTHF, MTBE, 1,4-dioxane, DME, and mixtures thereof.

Halogen means fluoro (F), chloro (Cl), bromo (Br) or iodo (I).

The term "halogenated alkane" refers to alkanes comprising one or more carbon atoms and one or more halogen atoms. Halogenated alkanes may comprise between 1 and 10 carbon atoms and between 1 and 10 halogen atoms. Examples of halogenated alkanes include DCM, chloroform, carbon tetrachloride, and 1,2-dichloroethane.

The term "ketone" refers to compounds of formula R'—C(O)—R". R' may be a substituted or unsubstituted alkyl group, such as a substituted or unsubstituted $C_1$-$C_{10}$ alkyl group or; or a substituted or unsubstituted aryl group, such as a substituted or unsubstituted phenyl group. R" may be a substituted or unsubstituted alkyl group, such as a substituted or unsubstituted $C_1$-$C_{10}$ alkyl group or; or a substituted or unsubstituted aryl group, such as a substituted or unsubstituted phenyl group. R' and R" may be the same. R' and R" may be different. R' and R" together may form a substituted or unsubstituted cyclic alkyl group, such as a substituted or unsubstituted $C_3$-$C_{10}$ cyclic alkyl group. Examples of ketones include acetone, methyl ethyl ketone, cyclohexanone, and mixtures thereof.

The term "nitrile" refers to compounds of formula R'—CN. R' may be a substituted or unsubstituted alkyl group, such as a substituted or unsubstituted $C_1$-$C_{10}$ alkyl group; a substituted or unsubstituted cyclic alkyl group, such as a substituted or unsubstituted $C_3$-$C_{10}$ cyclic alkyl group; a substituted or unsubstituted aryl group, such as a substituted or unsubstituted phenyl group. Examples of nitriles include MeCN, propionitrile, benzonitrile, and mixtures thereof.

The terms "nucleophile" and "nucleophilic reagent" refer to a Lewis base. Examples of nucleophilic reagents include ammonia, azide, amines, enols, organolithium reagents, alkyl-magnesium halides, allyl-magnesium halides, vinyl-magnesium halides, aryl-magnesium halides, and mixtures thereof.

The term "oxidizing agent" refers to compounds that gain electrons and are reduced in a chemical reaction. Examples of oxidizing agents include peroxides, such as hydrogen peroxide, urea hydrogen peroxide, acetyl benzoyl peroxide, benzoyl peroxide, tert-butyl hydroperoxide, diacetyl peroxide, ethyl hydroperoxide, methyl ethyl ketone peroxide, sodium percarbonate, and peroxy acids; oxygen; ozone; halogens; metal oxides; permanganate compounds, such as potassium permanganate; and perborate salts, such as lithium perborate, sodium perborate, and potassium perborate. Examples of peroxy acids include peracetic acid, performic acid, peroxybenzoic acid, mCPBA, peroxymonosulfuric acid, peroxynitric acid, and peroxymonophosphoric acid. Perborate salts may be in the form of a hydrate, such as sodium perborate tetrahydrate The term "pharmaceutically acceptable" refers to a non-toxic material that does not interfere with the effectiveness of the active ingredient(s).

The term "reducing agents" refers to compounds that lose electrons and are oxidized in a chemical reaction. Examples of reducing agents include hydrogen, lithium aluminum hydride, sodium borohydride, thiosulfate salts, hydrazine, and diisobutylaluminum hydride.

The term "room temperature" refers to a temperature range between 19° C. and 26° C.

Substituted aryl groups, substituted alkyl groups, and substituted cycloalkyl groups are substituted with one or more substituents selected from the group consisting of $C_1$-$C_6$ alkyl, —$OR_a$, —$SR_b$, —$NR_cR_d$, —F, —Cl, —Br, —I, —CN, —$NO_2$, phenyl, pyridyl, —CHO, —$COOR_e$, and —$CO(NR_fR_g)$; wherein each of $R_a$, Rb, $R_c$, $R_d$, $R_e$, $R_f$, and $R_g$ are independently selected from H or $C_1$-$C_6$ alkyl.

As used herein, "water" refers to both to tap water, distilled water, or deionized water.

As used herein, the terms formula (I), formula (II), formula (III), formula (IV), and formula (V) may be hereinafter referred to as a "compound(s) of the invention," "the invention," and respectively "compound(s) of formula (I)," "compound(s) of formula (II)," "compound(s) of formula (III)," "compound(s) of formula (IV)," and "compound(s) of formula (V)." Such terms are also defined to include all forms of the compound(s) of formula (I), compound(s) of formula (II), compound(s) of formula (III), compound(s) of formula (IV), and compound(s) of formula (V), including pharmaceutically acceptable salts, hydrates, solvates, isomers, crystalline and non-crystalline forms, isomorphs, polymorphs, and metabolites thereof. For example, the compounds of the invention, or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Examples

Example 1 - Synthesis of Compound of Formula (IV)

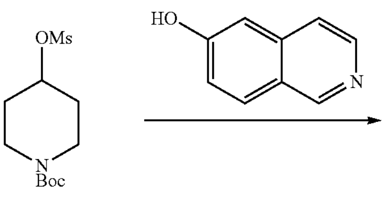

-continued

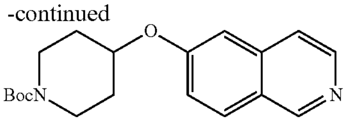

In a round-bottom flask was added isoquinolin-6-ol, a compound of formula (III) (40.0 g, 1.0 eq.), tert-butyl 4-((methylsulfonyl)oxy)piperidine-1-carboxylate, a compound of formula (II) (1.6 eq.), and potassium carbonate (4.0 eq.) in DMF (15 volumes) under nitrogen at room temperature. The reaction mixture was heated to 100° C. in 1 hour and the reaction mixture maintained at 100° C. for 16 hours. The reaction was then cooled to room temperature in 1 hour and water (30 volumes) was added. The reaction mixture was extracted with methyl tert-butyl ether MTBE (3×10 volumes), the combined MTBE layers were washed with 10% aq. NaOH (2×5 volumes) followed by water (10 volumes). The MTBE layer was distilled under vacuum below 45° C. up to 1 volume and n-hexane (5 volumes) was added and evaporated to 1 volume. The same procedure was repeated one more time with n-hexane (5 volumes) and completely distilled to dryness under vacuum below 45° C. to constant weight to yield 85.0 g of a crude product. To the crude product was added n-hexane (5 volumes) at room temperature and cooled to 0-5° C. in 30 minutes and stirred for 1 hour at 0-5° C. The solid was filtered and washed the solid with cold n-hexane (2 volumes) and sucked dry. The wet cake was dried under vacuum below 45° C. to constant weight to get 69.5 g of tert-butyl 4-(isoquinolin-6-yloxy) piperidine-1-carboxylate, a compound of formula (IV) in 77% yield.

Example 2 - Synthesis of Compound of Formula (V)

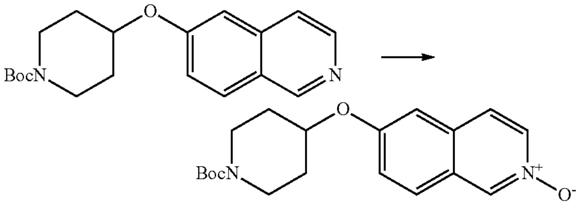

In a round-bottom flask was added tert-butyl 4-(isoquinolin-6-yloxy)piperidine-1-carboxylate, a compound of formula (IV) (90.0 g, 1.0 eq.) in DCM (15 volumes) and was cooled to 5-10° C. over a period of 30 minutes. mCPBA (1.8 eq.) was added at 5-10° C. lot-wise (4 equal lots). The reaction mixture was allowed to come to room temperature over a period of 2 hours and maintained at room temperature for 1 hour. The reaction was monitored by HPLC. The reaction mixture was diluted with DCM (10 volumes) and quenched with 40% aq. sodium metabisulfite solution (10 volumes) at room temperature. The resulting aqueous and DCM layers were separated, and the DCM layer was washed with 10% aq. NaOH (10 volumes) followed by water (10 volumes). The DCM layer was distilled up to 1 volume, MTBE (5 volumes) was added. The solvent was distilled off up to 1 volume and the same procedure was repeated one more time with MTBE (5 volumes). To the reaction mixture was added MTBE (5 volumes) and stirred for 1 hour at room temperature. The obtained solids were filtered and the solid was washed with MTBE (2 volumes). The wet cake was dried under vacuum below 45° C. to constant weight to get 75.0 g of 6-((1-(tert-butoxycarbonyl)piperidin-4-yl)oxy)isoquinoline 2-oxide, a compound of formula (V) in 80% yield.

Example 3 - Synthesis of Compound of Formula (I)

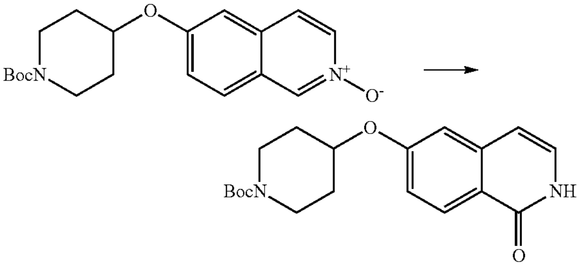

In a round-bottom flask was added 6-((1-(tert-butoxycarbonyl)piperidin-4-yl)oxy)isoquinoline 2-oxide, a compound of formula (V) (70.0 g, 1.0 eq.) and water:THF (10 volumes: 10 volumes) at room temperature to form a homogeneous reaction mixture. To the reaction mixture was added MsCl (2.0 eq.) at room temperature for 30 minutes. The reaction mixture was maintained at room temperature for 2 hours. MTBE (10 volumes) was added to the reaction mixture and the aqueous layer was extracted with MTBE (2×10 volumes). The combined MTBE layers were washed with 10% aq. $KHSO_4$ (2×10 volumes). The solvent was distilled under vacuum below 45° C. to constant weight to get crude in 52.0 g, with a purity of 95.35% (measured by HPLC). To the crude (52.0 g) added acetone (4 volumes) and was stirred at room temperature for 3 hours. The solids were filtered and washed with cold acetone (1 volume). The resulting solid was dried under vacuum below 45° C. to constant weight to get 33.0 g of tert-butyl 4-((1-oxo-1,2-dihydroisoquinolin-6-yl)oxy)piperidine-1-carboxylate, a compound of formula (I) as an off-white solid in 47% yield.

Example 4 - Deprotection of Compound of Formula (I)

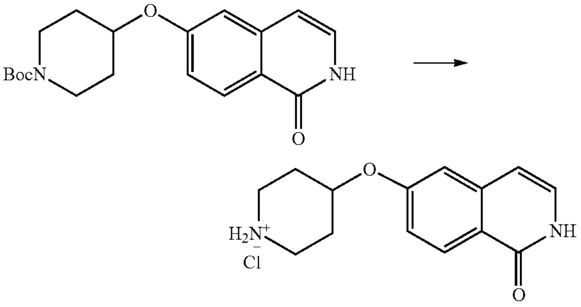

To a solution of acyl chloride (7.5 eq.) in isopropanol (10 volumes) at room temperature was added tert-butyl 4-((1-oxo-1,2-dihydroisoquinolin-6-yl)oxy)piperidine-1-carboxylate (5.5 g, 1.0 eq.). The reaction mixture was stirred at room temperature for 16 hours. Solids in the reaction mixture were filtered and washed with isopropanol (2 volumes) to get 4.2 g 6-(piperidin-4-yloxy)isoquinolin-1(2H)-one hydrochloride (93% yield, 98.4% purity by HPLC).

Example 5 - Synthesis of Compound of Formula (IV)

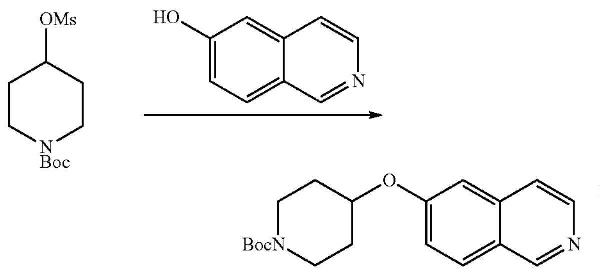

In a 500-mL three-neck flask with overhead agitation, thermometer, and condenser under nitrogen were added isoquinolin-6-ol (1.0 eq.), tert-butyl 4-((methylsulfonyl) oxy)piperidine-1-carboxylate (1.6 eq.), and cesium carbonate (2.0 eq.). Dimethyl formamide (DMF, 5 volumes) was added to form a slurry, then water (1 volume) was added slowly. The reaction mixture was heated to 90° C. for 16 hours. The reaction mixture was then cooled to room temperature, and water (5 volumes) and MTBE (5 volumes) were added. The resulting mixture was stirred, and the organic and aqueous layers were separated. The aqueous layer was extracted with MTBE (3 volumes), and the combined MTBE layers were washed with 10% aq. NaOH (2×5 volumes) followed by water (5 volumes) and then brine (5 volumes). The resulting MTBE layer was distilled under vacuum at 40-50° C. to 5 volumes, then heptanes (5 volume) was added, and then the organic layer was concentrated to 5 volumes. The process of distilling under vacuum, adding heptanes, and concentrating was repeated twice until the amount of residual MTBE was <2% w/w. The resulting slurry was cooled to 5° C. and stirred overnight. The slurry was then filtered and washed with heptanes that had been cooled to 5° C. The resulting solids were dried overnight on the filter with suction and nitrogen counterbalance to obtain tert-butyl 4-(isoquinolin-6-yloxy)piperidine-1-carboxylate as an off-white solid in 85% yield, >98% purity by HPLC.

Example 6 - Synthesis of Compound of Formula (V)

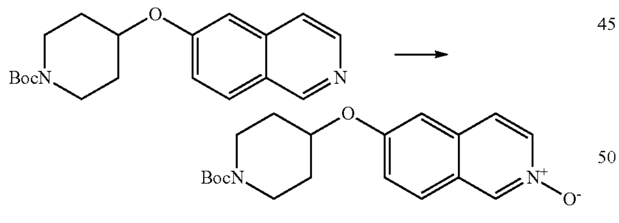

In a 500-mL three-neck flask with thermometer, condenser, and overhead agitator purged with nitrogen were added tert-butyl 4-(isoquinolin-6-yloxy)piperidine-1-carboxylate, urea-hydrogen peroxide (2.2 eq), and PMA (0.2 mol %) in MeCN (10 volumes). The reaction mixture was heated to 50° C. for 16 hours. The reaction mixture was then cooled to room temperature, and dimethylsulfoxide (DMSO, 1.5 eq.) was added to the reaction mixture to quench excess peroxides. Subsequently, DCM (10 volumes) and water (5 volumes) were added. The resulting mixture was stirred, and the organic and aqueous layers were separated. The organic layer was washed with 5% aq. NaOH (5 volumes), then 10% aq. citric acid (5 volumes), then water (5 volumes), and then brine (2 volumes). The organic layer was concentrated to 5 volumes under vacuum at 40° C., then MTBE (5 volumes) was added to the organic layer at 50° C., and then the organic layer was again concentrated to 5 volumes by vacuum distillation. The process of concentrating under vacuum, adding MTBE, and concentrating again was repeated three more times until the amount of residual DCM was <0.5% w/w, the amount of residual MeCN was <10% w/w, and the amount of residual water was <0.5% w/w. The resulting slurry was cooled to room temperature and stirred overnight. The slurry was then filtered and washed with MTBE (2 volumes). The resulting solids were dried overnight on the filter with suction and nitrogen counterbalance to obtain 6-((1-(tert-butoxycarbonyl)piperidin-4-yl)oxy)isoquinoline 2-oxide as an off-white solid in 85% yield, >98% purity by HPLC.

Example 7 - Synthesis of Compound of Formula (I)

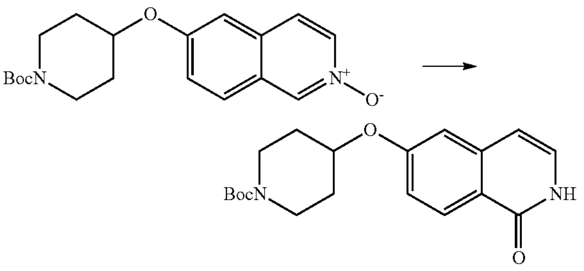

In a 500-mL three-neck flask with overhead stirrer, thermometer, addition funnel, and cooling batch purged with nitrogen were added 6-((1-(tert-butoxycarbonyl)piperidin-4-yl)oxy)isoquinoline 2-oxide (1 eq.) and $NaHCO_3$ (4.0 eq.) in THF (10 volumes) and water (10 volumes). The resulting solution was then cooled to 5° C., and methanesulfonyl chloride (MsCl, 2.0 eq.) was added dropwise over 15 minutes. The reaction mixture was stirred for 2-3 hours at 5° C. The pH of the reaction mixture was monitored and kept above pH 4 by charging additional $NaHCO_3$ to the reaction mixture as required. The reaction mixture was then warmed to room temperature. The organic and aqueous layers were separated, and the aqueous layer was back-extracted with 2×2.5 volumes of THF. The combined organic layers were then washed with 25% w/w aq. $K_3PO_4$ (3.5 volumes) for 1 hour while monitoring for a stable pH reading above pH 4. The organic layer was then concentrated to 4 volumes by vacuum distillation at 40° C., MeCN (4 volumes) was added to the organic layer, and then the organic layer was again concentrated to 4 volumes by vacuum distillation at 40° C. The process of concentrating under vacuum, adding MeCN, and concentrating again was repeated twice more until the amount of residual THF was <1% w/w. The resulting slurry was then warmed to 45° C., and water (8.3 volumes) was added over 1 hour. The slurry was then cooled to room temperature and stirred for 3 hours, then the slurry was filtered and washed with water (2 volumes). The resulting solids were dried overnight on the filter with suction and nitrogen counterbalance to obtain tert-butyl 4-((1-oxo-1,2-dihydroisoquinolin-6-yl)oxy)piperidine-1-carboxylate as an off-white solid in 70% yield, >98% purity by HPLC.

Example 8 - Deprotection of Compound of Formula (I)

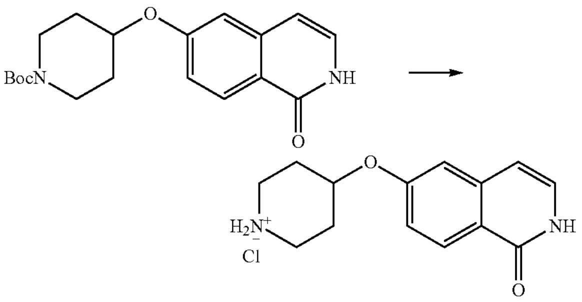

In a 250-mL three-neck flask with overhead stirrer, thermometer, and addition funnel purged with nitrogen was added isopropanol (5 volumes). The isopropanol was cooled to 0-5° C., and acetyl chloride (7.5 eq.) was added over 30 minutes to the isopropanol while maintaining the temperature at no more than 25° C. A slurry of tert-butyl 4-((1-oxo-1,2-dihydroisoquinolin-6-yl)oxy)piperidine-1-carboxylate (1 eq.) in isopropanol (5 volumes) was added over 10 minutes to the mixture of acetyl chloride in isopropanol. The reaction mixture was then stirred at room temperature for 24 hours. The resulting slurry was filtered and washed with isopropanol (2×2 volumes). The resulting solids were dried on the filter overnight with suction and nitrogen counterbalance to obtain 6-(piperidin-4-yloxy)isoquinolin-1(2H)-one hydrochloride as an off-white solid in 88% yield, >98% purity by HPLC.

Example 9 - Hydrate Formation of Salt of Compound of Formula (I)

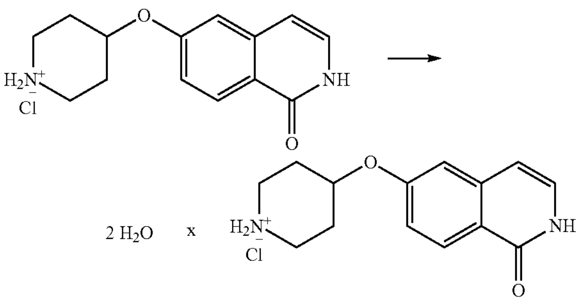

In a 100-mL reactor purged with nitrogen, 6-(piperidin-4-yloxy)isoquinolin-1(2H)-one hydrochloride was added. Acetone (2 volumes) was then added to the 6-(piperidin-4-yloxy)isoquinolin-1(2H)-one hydrochloride in the reactor, then water (2 volumes) was added. The resulting slurry was heated to 65° C. to obtain a solution. The resulting solution was polish filtered to a pre-heated vessel and rinsed with a 2:1 mixture of acetone:water (1 volume). The resulting slurry was then reheated to 65° C. to obtain a solution, then cooled to 50° C. over 30 minutes. Acetone (2 volumes) was added over 1 hour to the solution, then the solution was cooled to 5° C. over 7.5 hours and stirred overnight. The resulting slurry was filtered and washed with a 2:1 mixture of acetone:water (1 volume) that had been cooled to 5° C. The resulting solids were dried, then further dried in a vacuum oven at 30° C. containing a solution of brine to obtain a dihydrate of 6-(piperidin-4-yloxy)isoquinolin-1(2H)-one hydrochloride as an off-white solid in 83% yield, 99.9% purity by HPLC.

Although preferred embodiments of the invention have been described herein in detail, it will be understood by those skilled in the art that variations may be made thereto without departing from the spirit of the invention or the scope of the appended claims.

The subject-matter of the disclosure may also relate, among others, to the following aspects:

A first aspect relates to a process for preparing a compound of formula (V) or a pharmaceutically acceptable salt thereof (V)

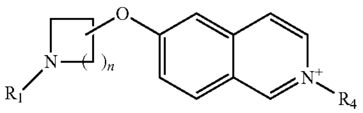

comprising: i) a step A, reacting a compound of formula (II) or a pharmaceutically acceptable salt thereof (II)

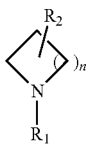

with a compound of formula (III) or a pharmaceutically acceptable salt thereof (III)

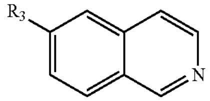

to produce a compound of formula (IV) or a pharmaceutically acceptable salt thereof (IV)

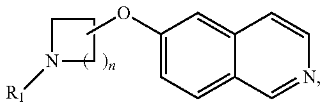

and ii) a step B, reacting the compound of formula (IV) or the pharmaceutically acceptable salt thereof (IV)

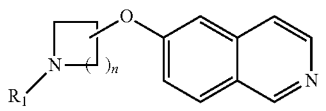

to produce the compound of formula (V) or the pharmaceutically acceptable salt thereof

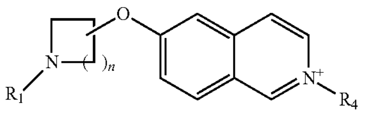

(V)

wherein $R_1$ is H, a $C_1$-$C_6$ alkyl group, or a protecting group that prevents the nitrogen atom to which it is attached from reacting with other molecules during a chemical reaction and is selected from the group consisting of a trityl (triphenylmethyl, Tr) group, a (4-methoxyphenyl)diphenylmethylene (methoxytrityl, MMT) group, a tert-butyloxycarbonyl (BOC) group, and a p-toluenesulfonyl (tosyl, Ts) group; n is 1, 2, 3, or 4; $R_2$ is —OH or $L_1$, a leaving group that is capable of being substituted by a nucleophile and is selected from the group consisting of fluoride (—F), chloride (—Cl), bromide (—Br), iodide (—I), p-toluenesulfonate (-TsO), methanesulfonate (-MsO), and trifluoromethanesulfonate (—$CF_3SO_3$); $R_3$ is —OH or $L_2$, a leaving group that is capable of being substituted by a nucleophile; and is selected from the group consisting of fluoride (—F), chloride (—Cl), bromide (—Br), iodide (—I), p-toluenesulfonate (-TsO), methanesulfonate (-MsO), and trifluoromethanesulfonate (—$CF_3SO_3$); $R_4$ is selected from the group consisting of —OH, —O—, p-toluenesulfonate (-TsO), methanesulfonate (-MsO), and trifluoromethanesulfonate (—$CF_3SO_3$).

A second aspect relates to the process of aspect 1, wherein the $C_1$-$C_6$ alkyl group is selected from the group consisting of methyl, ethyl, n-propyl, isopropyl, n-butyl, sec-butyl, and tert-butyl; wherein $L_1$ is selected from the group consisting of chloride (—Cl), bromide (—Br), iodide (—I), p-toluenesulfonate (-TsO), methanesulfonate (-MsO), and trifluoromethanesulfonate (—$CF_3SO_3$); and wherein $L_2$ is selected from the group consisting of chloride (—Cl), bromide (—Br), iodide (—I), p-toluenesulfonate (-TsO), methanesulfonate (-MsO), and trifluoromethanesuflonate (—$CF_3SO_3$).

A third aspect relates to the process of aspect 1 or 2, wherein $R_1$ is a protecting group selected from the group consisting of a trityl (triphenylmethyl, Tr) group, a (4-methoxyphenyl)diphenylmethylene (methoxytrityl, MMT) group, a tert-butyloxycarbonyl (BOC) group, and a p-toluenesulfonyl (tosyl, Ts) group; wherein n is 2 or 3; wherein $R_2$ is $L_1$ and $R_3$ is —OH or $R_2$ is —OH and $R_3$ is $L_2$; wherein $L_1$ is selected from the group consisting of chloride (—Cl), bromide (—Br), iodide (—I), p-toluenesulfonate (-TsO), methanesulfonate (-MsO), and trifluoromethanesulfonate (—$CF_3SO_3$); and wherein $L_2$ is selected from the group consisting of chloride (—Cl), bromide (—Br), iodide (—I), p-toluenesulfonate (-TsO), methanesulfonate (-MsO), and trifluoromethanesulfonate (—$CF_3SO_3$).

A fourth aspect relates to the process of aspects 1 to 3, wherein $R_1$ is a tert-butyloxycarbonyl (BOC) group; n is 3; $R_2$ is $L_1$; and $L_1$ is methanesulfonate (-MsO); or wherein $R_2$ is —OH; and wherein $L_2$ is chloride (—Cl), bromide (—Br), or iodide (—I).

A fifth aspect relates to the process of any preceding aspect, wherein step A is carried out from about 0° C. to about 150° C.; and wherein step B is carried out from about −10° C. to about 50° C. or from about 25° C. to about 150° C.

A sixth aspect relates to the process of any preceding aspect, wherein A is carried out from about 50° C. to about 110° C.; and wherein step B is carried out from about 0° C. to about 25° C. or from about 45° C. to about 100° C.

A seventh aspect relates to the process of any preceding aspect, wherein 1 to 5 molar equivalents of the compound of formula (II) or a pharmaceutically acceptable salt thereof relative to the compound of formula (III) or a pharmaceutically acceptable salt thereof are used in step A.

An eighth aspect relates to the process of any preceding aspect, wherein step A is carried out in the presence of a base and a solvent; and wherein step B is carried out in the presence of an oxidizing agent and a solvent.

A ninth aspect relates to the process of aspect 8, wherein 1 to 5 molar equivalents of the compound of formula (II) or a pharmaceutically acceptable salt thereof relative to the compound of formula (III) or a pharmaceutically acceptable salt thereof are used in step A, and wherein 1 to 7 molar equivalents of base relative to the compound of formula (III) or a pharmaceutically acceptable salt thereof are used in step A.

A tenth aspect relates to the process of aspect 8 or 9, wherein 1 to 10 molar equivalents of oxidizing agent relative to the compound of formula (IV) or a pharmaceutically acceptable salt thereof are used in step B.

An eleventh aspect relates to the process any one of aspects 8 to 10, wherein the base in step A is selected from the group consisting of ammonia, methyl amine, dimethyl amine, trimethyl amine, ethyl amine, diethyl amine, triethyl amine, propyl amine, dipropyl amine, tripropyl amine, isopropyl amine, diisopropyl amine, triisopropyl amine, N,N-diisopropylethylamine, lithium methoxide, sodium methoxide, potassium methoxide, lithium ethoxide, sodium ethoxide, potassium ethoxide, lithium tert-butoxide, sodium tert-butoxide, potassium tert-butoxide, lithium hydroxide, sodium hydroxide, potassium hydroxide, lithium carbonate, sodium carbonate, potassium carbonate, cesium carbonate, lithium bicarbonate, sodium bicarbonate, potassium bicarbonate, and mixtures thereof; wherein the solvent in step A is selected from the group consisting of water, diethyl ether, tetrahydrofuran (THF), 2-methyltetrahydrofuran (2-MeTHF), dimethoxyethane (DME), methyl tert-butyl ether (MTBE), 1,4-dioxane, dimethylformamide (DMF), dimethylacetamide (DMA), 2-pyrrolidone, acetonitrile (MeCN), propionitrile, benzonitrile, and mixtures thereof; wherein the oxidizing agent in step B is selected from the group consisting of hydrogen peroxide, urea hydrogen peroxide, sodium percarbonate, acetone peroxide, acetyl benzoyl peroxide, benzoyl peroxide, tert-butyl hydroperoxide, diacetyl peroxide, ethyl hydroperoxide, methyl ethyl ketone peroxide, peracetic acid, performic acid, peroxybenzoic acid, meta-chloroperoxybenzoic acid (mCPBA), dimethyldioxirane, oxone (potassium peroxymonosulfate), peroxymonosulfuric acid, peroxynitric acid, peroxymonophosphoric acid, potassium permanganate, lithium perborate, sodium perborate, potassium perborate, and mixtures thereof; and wherein the solvent in step B is selected from the group consisting of dichloromethane (DCM), chloroform, carbon tetrachloride, 1,2-dichloroethane, MeCN, propionitrile, benzonitrile, acetic acid, formic acid, trifluoroacetic acid, and mixtures thereof.

A twelfth aspect relates to the process of any one of aspects 8 to 11, wherein the base in step A is selected from the group consisting of potassium hydroxide, potassium carbonate, cesium carbonate, potassium tert-butoxide, and mixtures thereof; wherein the solvent in step A is selected from the group consisting of DMF, MeCN, water, diethyl ether, MTBE, and mixtures thereof; wherein the oxidizing agent in step B is selected from the group consisting of hydrogen peroxide, urea hydrogen peroxide, sodium percarbonate, peracetic acid, performic acid, peroxybenzoic acid, mCPBA, peroxymonosulfuric acid, peroxynitric acid, peroxymonophosphoric acid, sodium perborate, and mixtures thereof; and wherein the solvent in step B is selected from the group consisting of DCM, chloroform, MeCN, ethanol, acetic acid, and mixtures thereof.

A thirteenth aspect relates to the process of any one of the preceding aspects, wherein step A is carried out in the presence of a base and a solvent; and wherein step B is carried out in the presence of an oxidizing agent, a catalyst, and a solvent.

A fourteenth aspect relates to the process of aspect 13, wherein 1 to 10 molar equivalents of oxidizing agent relative to the compound of formula (IV) or a pharmaceutically acceptable salt thereof are used in step B, and wherein 0.001 to 1 molar equivalents of catalyst relative to the compound of formula (IV) or a pharmaceutically acceptable salt thereof are used in step B.

A fifteenth aspect relates to the process of aspect 13 or 14, wherein the base in step A is selected from the group consisting of ammonia, methyl amine, dimethyl amine, trimethyl amine, ethyl amine, diethyl amine, triethyl amine, propyl amine, dipropyl amine, tripropyl amine, isopropyl amine, diisopropyl amine, triisopropyl amine, N,N-diisopropylethylamine, lithium methoxide, sodium methoxide, potassium methoxide, lithium ethoxide, sodium ethoxide, potassium ethoxide, lithium tert-butoxide, sodium tert-butoxide, potassium tert-butoxide, lithium hydroxide, sodium hydroxide, potassium hydroxide, lithium carbonate, sodium carbonate, potassium carbonate, cesium carbonate, lithium bicarbonate, sodium bicarbonate, potassium bicarbonate, and mixtures thereof; wherein the solvent in step A is selected from the group consisting of water, diethyl ether, THF, 2-MeTHF, DME, MTBE, 1,4-dioxane, DMF, DMA, 2-pyrrolidone, MeCN, propionitrile, benzonitrile, and mixtures thereof; wherein the oxidizing agent in step B is selected from the group consisting of hydrogen peroxide, urea hydrogen peroxide, sodium percarbonate, acetyl benzoyl peroxide, benzoyl peroxide, tert-butyl hydroperoxide, diacetyl peroxide, ethyl hydroperoxide, methyl ethyl ketone peroxide, peracetic acid, performic acid, peroxybenzoic acid, mCPBA, peroxymonosulfuric acid, peroxynitric acid, peroxymonophosphoric acid, potassium permanganate, lithium perborate, sodium perborate, potassium perborate, and mixtures thereof; wherein the solvent in step B is selected from the group consisting of DCM, chloroform, carbon tetrachloride, 1,2-dichloroethane, MeCN, propionitrile, benzonitrile, acetic acid, formic acid, trifluoroacetic acid, and mixtures thereof; and wherein the catalyst in step B is selected from the group consisting of acetic acid, trifluoroacetic acid, formic acid, methyltrioxorhenium (VII) ($MeReO_3$, MTO), phosphomolybdic acid (PMA), and mixtures thereof.

A sixteenth aspect relates to the process any one of aspects 13 to 15, wherein the base in step A is selected from the group consisting of potassium hydroxide, potassium carbonate, cesium carbonate, potassium tert-butoxide, and mixtures thereof; wherein the solvent in step A is selected from the group consisting of DMF, MeCN, water, diethyl ether, MTBE, and mixtures thereof; wherein the oxidizing agent in step B is selected from the group consisting of hydrogen peroxide, urea hydrogen peroxide, sodium percarbonate, peracetic acid, performic acid, peroxybenzoic acid, mCPBA, peroxymonosulfuric acid, peroxynitric acid, peroxymonophosphoric acid, sodium perborate, and mixtures thereof; wherein the solvent in step B is selected from the group consisting of DCM, chloroform, MeCN, ethanol, acetic acid, and mixtures thereof; and wherein the catalyst in step B is selected from the group consisting of acetic acid, MTO, PMA, and mixtures thereof.

A seventeenth aspect relates to the process of any one of the preceding aspects, wherein step A is carried out in the presence of a base and a solvent; and wherein step B is carried out in the presence of an oxidizing agent, a catalyst, a base, and a solvent.

An eighteenth aspect relates to the process of aspect 17, wherein 1 to 10 molar equivalents of oxidizing agent relative to the compound of formula (IV) or a pharmaceutically acceptable salt thereof are used in step B, wherein 0.001 to 1 molar equivalents of catalyst relative to the compound of formula (IV) or a pharmaceutically acceptable salt thereof are used in step B, and wherein 1 to 10 molar equivalents of base relative to the compound of formula (IV) or a pharmaceutically acceptable salt thereof are used in step B.

A nineteenth aspect relates to the process of aspect 17 or 18, wherein the base in step A is selected from the group consisting of potassium hydroxide, potassium carbonate, cesium carbonate, potassium tert-butoxide, and mixtures thereof; wherein the solvent in step A is selected from the group consisting of DMF, MeCN, water, diethyl ether, MTBE, and mixtures thereof; wherein the oxidizing agent in step B is selected from the group consisting of hydrogen peroxide, urea hydrogen peroxide, sodium percarbonate, peracetic acid, performic acid, sodium perborate, mCPBA, and mixtures thereof; wherein the solvent in step B is selected from the group consisting of MeCN, ethanol, acetic acid, DCM, chloroform, and mixtures thereof; wherein the base in step B is selected from the group consisting of lithium bicarbonate, sodium bicarbonate, potassium bicarbonate, lithium carbonate, sodium carbonate, potassium carbonate, cesium carbonate, and mixtures thereof; and wherein the catalyst in step B is selected from the group consisting of acetic acid, formic acid, trifluoroacetic acid, MTO, PMA, and mixtures thereof.

A twentieth aspect relates to a process for preparing a compound of formula (I) or a pharmaceutically acceptable salt thereof comprising a step C, reacting a compound of formula (V) or a pharmaceutically acceptable salt thereof (V)

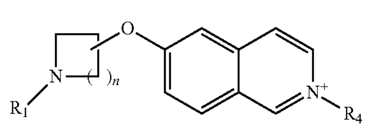

to produce a compound of formula (I) or a pharmaceutically acceptable salt thereof (I)

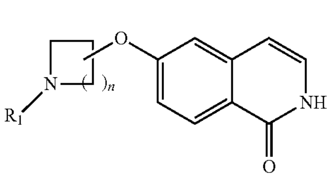

wherein $R_1$ is H, a $C_1$-$C_6$ alkyl group, or a protecting group selected from the group consisting of a trityl (triphenylmethyl, Tr) group, a (4-methoxyphenyl)diphenylmethylene (methoxytrityl, MMT) group, a tert-butyloxycarbonyl (BOC) group, and a p-toluenesulfonyl (tosyl, Ts) group; n is 1, 2, 3, or 4; and $R_4$ is selected from the group consisting of —OH, —O—, p-toluenesulfonate (-TsO), methanesulfonate (-MsO), and trifluoromethanesulfonate (—$CF_3SO_3$).

A twenty-first aspect relates to the process of aspect 20, wherein the compound of formula (I) or a pharmaceutically acceptable salt thereof is in its lactam form and/or in its lactim form.

A twenty-second aspect relates to the process of aspect 20 or 21, wherein $R_1$ is H; a $C_1$-$C_6$ alkyl group selected from the group consisting of methyl, ethyl, n-propyl, isopropyl, n-butyl, sec-butyl, and tert-butyl; or a protecting group selected from the group consisting of a trityl (triphenylmethyl, Tr) group, a (4-methoxyphenyl)diphenylmethylene (methoxytrityl, MMT) group, a tert-butyloxycarbonyl (BOC) group, and a p-toluenesulfonyl (tosyl, Ts) group; wherein n is 1, 2, or 3; $R_4$ is selected from the group consisting of —OH, —O—, p-toluenesulfonate (-TsO), methanesulfonate (-MsO), and trifluoromethanesulfonate (—$CF_3SO_3$).

A twenty-third aspect relates to the process of aspect 22, wherein $R_1$ is a protecting group selected from the group consisting of a trityl (triphenylmethyl, Tr) group, a (4-methoxyphenyl)diphenylmethylene (methoxytrityl, MMT) group, a tert-butyloxycarbonyl (BOC) group, and a p-toluenesulfonyl (tosyl, Ts) group; wherein n is 2 or 3; $R_4$ is selected from the group consisting of —OH, —O—, p-toluenesulfonate (-TsO), methanesulfonate (-MsO), and trifluoromethanesulfonate (—$CF_3SO_3$).

A twenty-fourth aspect relates to the process of any one of aspects 20 to 23, wherein $R_1$ is a tert-butyloxycarbonyl (BOC) group; wherein n is 3; and wherein $R_4$ is selected from the group consisting of —OH, —O—, and methanesulfonate (-MsO).

A twenty-fifth aspect relates to the process of any one of aspects 20 to 24, wherein step C is carried out at a temperature of from about −10° C. to about 100° C.

A twenty-sixth aspect relates to the process of aspect 25, wherein step C is carried out at a temperature of from about 5° C. to about 50° C.

A twenty-seventh aspect relates to the process of any one of aspects 20 to 26, wherein step C is carried out in the presence of an electrophilic reagent, a solvent, and a base.

A twenty-eighth aspect relates to the process of aspect 27, wherein 0.05 to 10 molar equivalents of electrophilic reagent relative to the compound of formula (V) or a pharmaceutically acceptable salt thereof are used in step C, and wherein 0.1 to 10 molar equivalents of base relative to the compound of formula (V) or a pharmaceutically acceptable salt thereof are used in step C.

A twenty-ninth aspect relates to the process of any one of aspects 20 to 26, wherein step C is carried out in the presence of an electrophilic reagent, a solvent, and a buffer.

A thirtieth aspect relates to the process of aspect 29, wherein 0.05 to 10 molar equivalents of electrophilic reagent relative to the compound of formula (V) or a pharmaceutically acceptable salt thereof are used in step C, and wherein 0.1 to 10 molar equivalents of buffer relative to the compound of formula (V) or a pharmaceutically acceptable salt thereof are used in step C.

A thirty-first aspect relates to the process of any one of aspects 27 to 30, wherein the electrophilic reagent in step C is selected from the group consisting of acyl chloride, acyl bromide, acyl iodide, acetic anhydride, formic anhydride, acetic formic anhydride, trifluoroacetic anhydride, trimethylacetic anhydride, hexanoic anhydride, benzoic anhydride, benzensulfonyl chloride, benzensulfonyl bromide, benzensulfonyl iodide, methanesulfonyl chloride (mesyl chloride, MsCl), methanesulfonyl bromide, methanesulfonyl iodide, p-toluenesulfonyl chloride (tosyl chloride, TsCl), p-toluenesulfonyl bromide, p-toluenesulfonyl iodide, and mixtures thereof; wherein the solvent in step C is selected from the group consisting of water, DMF, DMA, 2-pyrrolidone, diethyl ether, THF, 2-MeTHF, DME, MTBE, 1,4-dioxane, acetone, methyl ethyl ketone, cyclohexanone, DCM, chloroform, carbon tetrachloride, 1,2-dichloroethane, MeCN, propionitrile, benzonitrile, and mixtures thereof; and wherein the base in step C is selected from the group consisting of ammonia, methyl amine, dimethyl amine, trimethyl amine, ethyl amine, diethyl amine, triethyl amine, propyl amine, dipropyl amine, tripropyl amine, isopropyl amine, diisopropyl amine, triisopropyl amine, N,N-diisopropylethylamine, lithium methoxide, sodium methoxide, potassium methoxide, lithium ethoxide, sodium ethoxide, potassium ethoxide, lithium tert-butoxide, sodium tert-butoxide, potassium tert-butoxide, hydroxide salts, carbonate salts, bicarbonate salts, phosphate salts, hydrogen phosphate salts, dihydrogen phosphate salts, lithium hydroxide, sodium hydroxide, potassium hydroxide, lithium carbonate, sodium carbonate, potassium carbonate, cesium carbonate, lithium bicarbonate, sodium bicarbonate, potassium bicarbonate, lithium phosphate, sodium phosphate, potassium phosphate, dilithium hydrogen phosphate, disodium hydrogen phosphate, dipotassium hydrogen phosphate, lithium dihydrogen phosphate, sodium dihydrogen phosphate, potassium dihydrogen phosphate, and mixtures thereof.

A thirty-second aspect relates to the process of any one of aspects 27 to 31, wherein the electrophilic reagent is selected from the group consisting of methanesulfonyl chloride (mesyl chloride, MsCl), p-toluenesulfonyl chloride (tosyl chloride, TsCl), acyl chloride, and mixtures thereof; the solvent is a mixture of water and at least one organic solvent selected from the group consisting of THF, 2-MeTHF, acetone, DCM, and MeCN; and the base is selected from the group consisting of triethyl amine, triisopropyl amine, N,N-diisopropylethylamine, sodium carbonate, potassium carbonate, sodium bicarbonate, potassium bicarbonate, sodium phosphate, potassium phosphate, disodium hydrogen phosphate, dipotassium hydrogen phosphate, sodium dihydrogen phosphate, potassium dihydrogen phosphate, and mixtures thereof.

A thirty-third aspect relates to the process of aspect 32 or 33, wherein the electrophilic reagent in step C is selected from the group consisting of methanesulfonyl chloride (mesyl chloride, MsCl), p-toluenesulfonyl chloride (tosyl chloride, TsCl), acyl chloride, acyl bromide, acetic anhydride, trifluoroacetic anhydride, trimethylacetic anhydride, and mixtures thereof; wherein the solvent in step C is selected from the group consisting of water, DMF, diethyl ether, THF, 2-MeTHF, DME, MTBE, 1,4-dioxane, acetone, methyl ethyl ketone, cyclohexanone, DCM, chloroform, MeCN, and mixtures thereof; and wherein the buffer in step C is a buffer that maintains the pH of the reaction mixture of step C in a pH range between pH 4 and pH 10.

A thirty-fourth aspect relates to the process of aspect 33, wherein the buffer is selected from the group consisting of sodium acetate-acetic acid buffer, $H_3PO_4$— $Na_2HPO_4$ buffer, $Na_2HPO_4$— $NaH_2PO_4$ buffer, imidazole-HCl buffer, $H_3PO_4$-triethylamine (TEA) buffer, citric acid-triethylamine (TEA) buffer, citric acid-tris(hydroxymethyl)aminomethane (TRIS) buffer, and 3-(N-morpholino)-propanesulfonic acid (MOPS)-triethylamine (TEA) buffer.

A thirty-fifth aspect relates to the process of any one of aspects 20 to 34, further comprising a deprotection step D, reacting a compound of formula (I) or a pharmaceutically acceptable salt thereof (I)

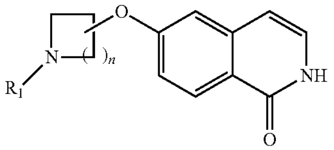

wherein $R_1$ is a protecting group selected from the group consisting of a trityl (triphenylmethyl, Tr) group, a (4-methoxyphenyl)diphenylmethylene (methoxytrityl, MMT) group, a tert-butyloxycarbonyl (BOC) group, and a p-toluenesulfonyl (tosyl, Ts) group; and n is 1, 2, 3, or 4 with a deprotection agent to produce a compound of formula (I) or a pharmaceutically acceptable salt thereof wherein $R_1$ is H and n is 1, 2, 3, or 4; and wherein the compound of formula (I) or a pharmaceutically acceptable salt thereof is in its lactam form and/or in its lactim form.

A thirty-sixth aspect relates to the process of aspect 35, wherein the protecting group is a tert-butyloxycarbonyl (BOC) group.

A thirty-seventh aspect relates to the process of aspect 35 or 36, wherein the deprotection reagent is selected from the group consisting of acyl chloride, acyl bromide, acyl iodide, acetic anhydride, formic anhydride, acetic formic anhydride, trifluoroacetic anhydride, trimethylacetic anhydride, hexanoic anhydride, benzoic anhydride, formic acid, acetic acid, trifluoroacetic acid, hydrochloric acid, hydrobromic acid, hydroiodic acid, and mixtures thereof.

A thirty-eighth aspect relates to the process of any one of aspects 35 to 37, wherein the protecting group is a tert-butyloxycarbonyl (BOC) group and the deprotection reagent is selected from the group consisting of acyl chloride, acyl bromide, acetic anhydride, formic acid, acetic acid, trifluoroacetic acid, and hydrochloric acid.

A thirty-ninth aspect relates to the process of any one of aspects 35 to 38, wherein the protecting group is a tert-butyloxycarbonyl (BOC) group and the deprotection agent is selected from the group consisting of acyl chloride, trifluoroacetic acid, and hydrochloric acid.

A fortieth aspect relates to the process of any one of aspects 35 to 39, wherein step D produces a monohydrochloride salt or a dihydrochloride salt of the compound of formula (I), and wherein the monohydrochloride salt or dihydrochloride salt of the compound of formula (I) is in its lactam form and/or in its lactim form.

A forty-first aspect relates to the process of any one of aspects 20 to 40, wherein step C produces a monohydrochloride salt or a dihydrochloride salt of the compound of formula (I), and wherein the monohydrochloride salt or dihydrochloride salt of the compound of formula (I) is in its lactam form and/or in its lactim form.

A forty-second aspect relates to the process of any one of aspects 35 to 41, wherein 1 to 20 molar equivalents of deprotection reagent relative to the compound of formula (I) or a pharmaceutically acceptable salt thereof are used in step D.

A forty-third aspect relates to a compound of formula (V) or a pharmaceutically acceptable salt thereof (V)

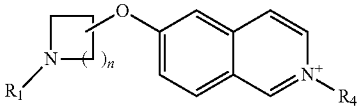

wherein n is 1, 2, 3, or 4; $R_1$ is H, a $C_1$-$C_6$ alkyl group, or a protecting group that prevents the nitrogen atom to which it is attached from reacting with other molecules during a chemical reaction and is selected from the group consisting of a trityl (triphenymethyl, Tr) group, a (4-methoxyphenyl)diphenylmethylene (methoxytrityl, MMT) group, a tert-butyloxycarbonyl (BOC) group, and a p-toluenesulfonyl (tosyl, Ts) group; and $R_4$ is selected from the group consisting of —OH, —O—, p-toluenesulfonate (-TsO), methanesulfonate (-MsO), and trifluoromethanesulfonate (—$CF_3SO_3$).

A forty-fourth aspect relates to the compound of aspect 43, wherein n is 1, 2, or 3; the $C_1$-$C_6$alkyl group is selected from the group consisting of methyl, ethyl, n-propyl, isopropyl, n-butyl, sec-butyl, and tert-butyl.

A forty-fifth aspect relates to the compound of aspect 43 or 44, wherein n is 2 or 3.

A forty-sixth aspect relates to the compound of any one of aspects 43 to 45, wherein n is 3; $R_1$ is a tert-butyloxycarbonyl (BOC) group; and $R_4$ is selected from the group consisting of —OH, —O—, and methanesulfonate (-MsO).

A forty-seventh aspect relates to the compound of aspects 43 to 45, wherein n is 3; $R_1$ is H; and $R_4$ is selected from the group consisting of —OH, —O—, and methanesulfonate (-MsO).

In addition to the features mentioned in each of the independent aspects enumerated above, some examples ma show, alone or in combination, the optional features mentioned in the dependent aspects and/or as disclosed in the description above and shown in the figures.

The invention claimed is:

1. A process for preparing a compound of formula (I) or a pharmaceutically acceptable salt thereof (V)

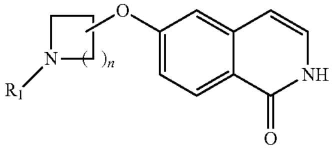

comprising:

i) a step A, reacting a compound of formula (II) or a pharmaceutically acceptable salt thereof (II)

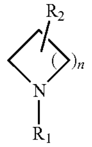

with a compound of formula (III) or a pharmaceutically acceptable salt thereof (III)

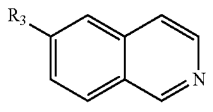

to produce a compound of formula (IV) or a pharmaceutically acceptable salt thereof (IV)

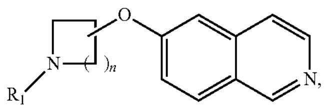

ii) a step B, reacting a compound of formula (IV) or a pharmaceutically acceptable salt thereof (IV)

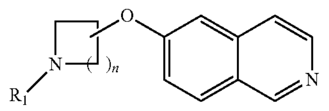

to produce a compound of formula (V) or a pharmaceutically acceptable salt thereof (V)

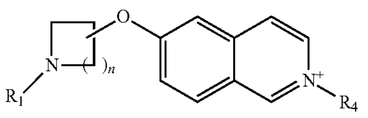

iii) a step C, reacting the compound of formula (V) or the pharmaceutically acceptable salt thereof (V)

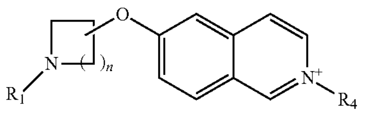

in the presence of an electrophilic reagent, a solvent, and a buffer to produce the compound of formula (I) or the pharmaceutically acceptable salt thereof (I)

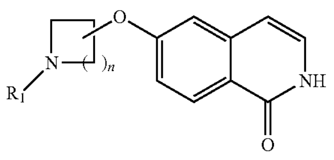

wherein $R_1$ is H, a $C_1$-$C_6$ alkyl group, or a protecting group that inhibits a nitrogen atom to which the protecting group is attached from reacting with other molecules during a chemical reaction and is selected from the group consisting of a trityl (triphenylmethyl, Tr) group, a (4-methoxyphenyl)diphenylmethylene (methoxytrityl, MMT) group, a tert-butyloxycarbonyl (BOC) group, and a p-toluenesulfonyl (tosyl, Ts) group;

n is 1, 2, 3, or 4;

$R_2$ is —OH or $L_1$, a leaving group that is capable of being substituted by a nucleophile and is selected from the group consisting of fluoride (—F), chloride (—Cl), bromide (—Br), iodide (—I), p-toluenesulfonate (-OTs), methanesulfonate (-OMs), and trifluoromethanesulfonate ($CF_3SO_3$—);

$R_3$ is —OH or $L_2$, a leaving group that is capable of being substituted by a nucleophile; and is selected form the group consisting of fluoride (—F), chloride (—Cl), bromide (—Br), iodide (—I), p-toluenesulfonate (-OTs), methanesulfonate (-OMs), and trifluoromethanesulfonate ($CF_3SO_3$—); and $R_4$ is selected from the group consisting of —OH, —O—, p-toluenesulfonate (-OTs), methanesulfonate (-OMs), and trifluoromethanesulfonate (—$SO_3CF_3$).

2. The process of claim 1, wherein the $C_1$-$C_6$ alkyl group is selected from the group consisting of methyl, ethyl, n-propyl, isopropyl, n-butyl, sec-butyl, and tert-butyl;

wherein n is 1, 2, or 3;

wherein $L_1$ is selected from the group consisting of chloride (—Cl), bromide (—Br), iodide (—I), p-toluenesulfonate (-OTs), methanesulfonate (-OMs), and trifluoromethanesulfonate ($CF_3SO_3$—); and wherein $L_2$ is selected from the group consisting of chloride (—Cl), bromide (—Br), iodide (—I), p-toluenesulfonate (-OTs), methanesulfonate (-OMs), and trifluoromethanesulfonate ($CF_3SO_3$—).

3. The process of claim 1, wherein $R_1$ is a protecting group selected from the group consisting of a trityl (triphenylmethyl, Tr) group, a (4-methoxyphenyl)diphenylmethylene (methoxytrityl, MMT) group, a tert-butyloxycarbonyl (BOC) group, and a p-toluenesulfonyl (tosyl, Ts) group;

wherein n is 2 or 3;

wherein $R_2$ is $L_1$ and $R_3$ is —OH, or $R_2$ is —OH and $R_3$ is $L_2$;

wherein $L_1$ is selected from the group consisting of chloride (—Cl), bromide (—Br), iodide (—I), p-toluenesulfonate (-OTs), methanesulfonate (-OMs), and trifluoromethanesulfonate ($CF_3SO_3$—); and wherein $L_2$ is selected from the group consisting of chloride (—Cl), bromide (—Br), iodide (—I), p-toluenesulfonate (-OTs), methanesulfonate (-OMs), and trifluoromethanesulfonate ($CF_3SO_3$—).

4. The process of claim 1, wherein $R_1$ is a tert-butyloxycarbonyl (BOC) group; n is 3; and wherein $R_2$ is methanesulfonate (-OMs); or wherein $R_2$ is —OH; and wherein $L_2$ is chloride (—Cl), bromide (—Br), or iodide (—I).

5. The process of claim 1, wherein step A is carried out from about 0° C. to about 150° C.; and wherein step B is carried out from about −10° C. to about 50° C. or from about 25° C. to about 150° C.

6. The process of claim 1, wherein 1 to 5 molar equivalents of the compound of formula (II) or a pharmaceutically acceptable salt thereof relative to the compound of formula (III) or a pharmaceutically acceptable salt thereof are used in step A.

7. The process of claim 1, wherein step A is carried out in the presence of a base and a first solvent; and wherein step B is carried out in the presence of an oxidizing agent and a second solvent.

8. The process of claim 7, wherein 1 to 5 molar equivalents of the compound of formula (II) or a pharmaceutically acceptable salt thereof relative to the compound of formula (III) or a pharmaceutically acceptable salt thereof are used in step A, and wherein 1 to 7 molar equivalents of base relative to the compound of formula (III) or a pharmaceutically acceptable salt thereof are used in step A.

9. The process of claim 7, wherein 1 to 10 molar b equivalents of oxidizing agent relative to the compound of formula (IV) or a pharmaceutically acceptable salt thereof are used in step B.

10. The process of claim 1, wherein step A is carried out in the presence of a base and a first solvent; and wherein step B is carried out in the presence of an oxidizing agent, a catalyst, and a second solvent.

11. The process of claim 10, wherein 1 to 10 molar equivalents of oxidizing agent relative to the compound of formula (IV) or a pharmaceutically acceptable salt thereof are used in step B, and wherein 0.001 to 1 molar equivalents of catalyst relative to the compound of formula (IV) or a pharmaceutically acceptable salt thereof are used in step B.

12. The process of claim 1, wherein step A is carried out in the presence of a base and a first solvent; and wherein step B is carried out in the presence of an oxidizing agent, a catalyst, a base, and a second solvent.

13. The process of claim 12, wherein 1 to 10 molar equivalents of oxidizing agent relative to the compound of formula (IV) or a pharmaceutically acceptable salt thereof are used in step B, wherein 0.001 to 1 molar equivalents of catalyst relative to the compound of formula (IV) or a pharmaceutically acceptable salt thereof are used in step B, and wherein 1 to 10 molar equivalents of base relative to the compound of formula (IV) or a pharmaceutically acceptable salt thereof are used in step B.

14. A process for preparing a compound of formula (I) or a pharmaceutically acceptable salt thereof comprising reacting a compound of formula (V) or a pharmaceutically acceptable salt thereof (V)

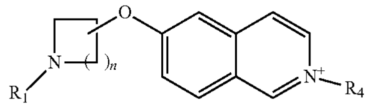

in the presence of an electrophilic reagent to produce the compound of formula (I) or the pharmaceutically acceptable salt thereof (I)

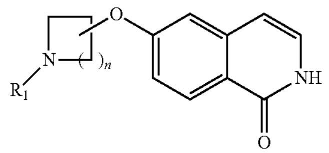

wherein $R_1$ is H, a C1-C6 alkyl group, or a protecting group selected from the group consisting of a trityl (triphenylmethyl, Tr) group, a (4-methoxyphenyl) diphenylmethylene (methoxytrityl, MMT) group, a tert-butyloxycarbonyl (BOC) group, and a p-toluenesulfonyl (tosyl, Ts) group;

nis 1, 2, 3, or 4; and $R_4$ is selected from the group consisting of-OH,-O, p-toluenesulfonate (-OTs), methanesulfonate (-OMs), and trifluoromethanesulfonate ($CF_3SO_3$-).

15. The process of claim 14, wherein the compound of formula (I) or a pharmaceutically acceptable salt thereof is in a lactam form and/or in a lactim form.

16. The process of claim 14, wherein $R_1$ is H; a C1-C6 alkyl group selected from the group consisting of methyl, ethyl, n-propyl, isopropyl, n-butyl, sec-butyl, and tert-butyl; or a protecting group selected from the group consisting of a trityl (triphenylmethyl, Tr) group, a (4-methoxyphenyl) diphenylmethylene (methoxytrityl, MMT) group, a tert-buyloxycarbonyl (BOC) group, and a p-toluenesulfonyl (tosyl, Ts) group;

wherein n is 1, 2, or 3; and $R_4$ is selected from the group consisting of-OH,-O, p-toluenesulfonate (-OTs), methanesulfonate (-OMs), and trifluoromethanesulfonate ($CF_3SO_3$-).

17. The process of claim 14, wherein reacting the compound of formula (V) or the pharmaceutically acceptable salt thereof to produce the compound of formula (I) or the pharmaceutically acceptable salt thereof is carried out at a temperature of from about-10° C. to about 100° C.

18. The process of claim 14, wherein reacting the compound of formula (V) or the pharmaceutically acceptable salt thereof to produce the compound of formula (I) or the pharmaceutically acceptable salt thereof is carried out in the presence of an electrophilic reagent, a solvent, and a base.

19. The process of claim 18, wherein 0.05 to 10 molar equivalents of electrophilic reagent relative to the compound of formula (V) or the pharmaceutically acceptable salt thereof are used, and wherein 0.1 to 10 molar equivalents of base relative to the compound of formula (V) or the pharmaceutically acceptable salt thereof are used.

20. The process of claim 14, wherein reacting the compound of formula (V) or the pharmaceutically acceptable salt thereof to produce the compound of formula (I) or the pharmaceutically acceptable salt thereof is carried out in the presence of an electrophilic reagent, a solvent, and a buffer.

21. The process of claim 20, wherein 0.05 to 10 molar equivalents of electrophilic reagent relative to the compound of formula (V) or the pharmaceutically acceptable salt thereof are used, and wherein 0.1 to 10 molar equivalents of buffer relative to the compound of formula (V) or the pharmaceutically acceptable salt thereof are used.

22. The process of claim 20, wherein the buffer is selected form the group consisting of sodium acetate-acetic acid buffer, $H_3PO_4$-$Na_2HPO_4$ buffer, $Na_2HPO_4$-$NaH_2PO_4$ buffer, imidazole-HCl buffer, $H_3PO_4$-triethylamine (TEA) buffer, citric acid-triethylamine (TEA) buffer, citric acid-tris (hydroxymethyl) aminomethane (TRIS) buffer, and 3-(N-morpholino)-propanesulfonic acid (MOPS)-triethylamine (TEA) buffer.

23. The process of claim 14, further comprising a deprotection step D of reacting a compound of formula (I) or a pharmaceutically acceptable salt thereof (I)

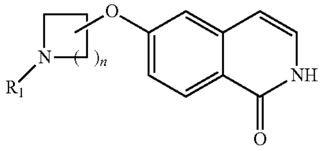

wherein $R_1$ is a protecting agent selected from the group consisting of a trityl (triphenylmethyl, Tr) group, a (4-methoxyphenyl) diphenylmethylene (methoxytrityl, MMT) group, a tert-buyloxycarbonyl (BOC) group, and a *p*-toluenesulfonyl (tosyl, Ts) group; and n is 1, 2, 3, or 4;

with a deprotection reagent to produce a compound of formula (I) or a pharmaceutically acceptable salt thereof wherein $R_1$ is H and n is 1, 2, 3, or 4; and wherein the compound of formula (I) or the pharmaceutically acceptable salt thereof wherein $R_1$ is H is in a lactam form and/or in a lactim form.

24. The process of claim 23, wherein the deprotection reagent is selected from the group consisting of acyl chloride, acyl bromide, acyl iodide, acetic anhydride, formic anhydride, acetic formic anhydride, trifluoroacetic anhydride, trimethylacetic anhydride, hexanoic anhydride, benzoic anhydride, formic acid, acetic acid, trifluoroacetic acid, hydrochloric acid, hydrobromic acid, hydroiodic acid, and mixtures thereof.

25. The process of claim 23, wherein step D produces a monohydrochloride salt or a dihydrochloride salt of the compound of formula (I), and wherein the monohydrochoride salt or the dihydrochloride salt of the compound of formula (I) is in a lactam form and/or in a lactim form.

26. The process of claim 14, wherein the process produces a monohydrochloride salt or a dihydrochloride salt of the compound of formula (I), and wherein the monohydrochloride salt or the dihydrochloride salt of the compound of formula (I) is in a lactam form and/or in a lactim form.

27. The process of claim 23, wherein 1 to 20 molar equivalents of deprotection reagent relative to the compound of formula (I) or the pharmaceutically acceptable salt thereof wherein $R_1$ is a protecting group are used in step D.

* * * * *